US008666674B2

(12) United States Patent
Kruse

(10) Patent No.: US 8,666,674 B2
(45) Date of Patent: *Mar. 4, 2014

(54) PAIRING PROCESSES FOR PREPARING REACTIVE CYTOTOXIC T CELLS

(75) Inventor: Carol A. Kruse, San Diego, CA (US)

(73) Assignee: Promising Future, LLC, Hagatna, GU (US)

(*) Notice: Subject to any disclaimer, the term of this patent is extended or adjusted under 35 U.S.C. 154(b) by 137 days.

This patent is subject to a terminal disclaimer.

(21) Appl. No.: 13/005,851

(22) Filed: Jan. 13, 2011

(65) Prior Publication Data

US 2011/0135617 A1 Jun. 9, 2011

Related U.S. Application Data

(63) Continuation-in-part of application No. 12/844,668, filed on Jul. 27, 2010.

(60) Provisional application No. 61/229,229, filed on Jul. 28, 2009, provisional application No. 61/229,233, filed on Jul. 28, 2009, provisional application No. 61/372,067, filed on Aug. 9, 2010.

(51) Int. Cl.
*G06F 7/00* (2006.01)

(52) U.S. Cl.
USPC .................................. 702/19; 702/20; 703/11

(58) Field of Classification Search
None
See application file for complete search history.

(56) References Cited

U.S. PATENT DOCUMENTS

| 5,976,546 A | 11/1999 | Laus et al. |
| 2004/0029554 A1 | 2/2004 | Hack |
| 2005/0048646 A1 | 3/2005 | Nieda |
| 2009/0162389 A1 | 6/2009 | Sheikh |
| 2011/0027245 A1* | 2/2011 | Kruse ........................ 424/93.71 |

FOREIGN PATENT DOCUMENTS

WO 2008081035 7/2008

OTHER PUBLICATIONS

Eric J. Small, Paige Fratesi, David M. Reese, George Strang, Reiner Laus, Madhusudan V. Peshwa,and Frank H. Valone, Immunotherapy of Hormone-Refractory Prostate Cancer With Antigen-Loaded Dendritic Cells Journal of Clinical Oncology 18(23): 3894-3903, Dec. 2000.
Dendreon's Provenge FDA Approval Lifts Cancer Immunotherapy Stocks, Favstocks: Biotech (Mike Havrilla), Apr. 29, 2010 at www.fool.com.
FDA Approves PROVENGE(R) for the Treatment of Men with Advanced Prostate Cancer—First FDA-Approved Autologous Cellular Immunotherapy Prolongs Survival, Dendreon Corporation, Apr. 29, 2010.
Stronen et. al., Dendritic Cells Engineered to Express Defined Allo-HLA Peptide Complexes Induce Antigen-Specific Cytotoxic T Cells Efficiently Killing Tumor Cells, Scand. J. Immunol. 69:319-328 (2009).
Active Immunotherapy, from web site: www.immatics.com, Downloaded on Jan. 13, 2011.
Press Release: Immatics Enters Collaboration with the NCI to Advance the Development of IMA950 for Glioblastoma, Feb. 6, 2010.
Tomonori Kato, Yasuji Urea, Hiroaki Kinoh, Yasuo Yoneyama, Akinao Matsunaga, Atsushi Komaru, Yui Harada, Hiroyoshi Suzuki, Akira Komiya, Satoko Shibata, Mamoru Hasegawa, Hideki Hayashi, Tomohiko Ichikawa and Yoshikazu Yonemeitsu, RIG-I Helicase-Independent Pathway in Sendai Virus-Activated Dendritic Cells is Critical for Preventing Lung Metastasis of AT6.3 Prostate Cancer, Neoplasia 12(11) pp. 906-914, Nov. 2010.
Immunology of the Nervous System, Robert W. Keane & William F. Hickey, editors, Oxford University Press, New York NY: Chapter 3: "Immunologic Principles Related to the Nervous System and the Eye: Concerning the Existence of a Neural-Ocular Immune System," J. Wayne Streilein & Andrew W. Taylor, pp. 99-133 (1997).
Immunology of the Nervous System, Robert W. Keane & William F. Hickey, editors, Oxford University Press, New York NY 1997: Chapter 21: "Tumors of the Central Nervous System," Carol J. Wikstrand & Darell D. Bigner, pp. 760-784.
Charles A. Janeway, Jr. Paul Travers with Simon Hunt & Mark Walport, Immunobiology: The Immune System in Health and Disease, Current Biology Ltd./Garland Publishing Inc. 1997. Distributed by Garland Publishing Inc., New York, NY: Chapter 12, pp. 32 & 33. Figure 12.29, "Immunologically Privileged Sites".
Hofman, F., Stathopoulos, A., Kruse, C.A., Chen, T., Schijns, V.E.J. C. (2010), Immunotherapy of malignant gliomas using autologous and allogeneic tissue cells, In Anti-Cancer Agents in Medicinal Chemistry Series: Emerging Therapeutic Targets and Agents for Glioblastoma Therapy, vol. 10. (2010).
Erwin G. Van Meir, Costas G. Hadjipanayis, Andrew D. Norton, Hui-Kuo Shu, Patrick Y. Wen and Jeffery J. Olson Exciting New Advances in Neuro-Oncology: The Avenue to a Cure for Malignant Glioma, CA: A Cancer Journal for Clinicians (2010) 60 (3) 166-193.
Kazunori Haga, Atsushi Tomioka, Chun-Peng Liao, Takahiro Kimura, Hiroshi Matsumoto, Izumi Ohno, Kip Hermann, Christopher R. Logg, Jing Jiao, Motoyoshi Tanaka, Yoshihiko Hirao, Hong Wu, Carol A. Kruse, Pradip Roy-Burman and Noriyuki Kasahara, PTEN Knowckout Prostate Cancer as a Model for Experimental Immunotherapy, Journal of Urology, vol. 181, 354-362, 2009.

(Continued)

Primary Examiner — Michail Belyavskyi
(74) Attorney, Agent, or Firm — Themis Law; Franco A. Serafini; David M. Fortner

(57) ABSTRACT

Provided in certain embodiments are methods for pairing patient cells and donor cells to prepare cytotoxic T cells, either in vitro or, when their formation is induced in a subject, in vivo. Such cytotoxic T cells could be administered to the patient for treating certain disorders, such as a cancer (for example, brain cancer).

30 Claims, 11 Drawing Sheets

(56) References Cited

OTHER PUBLICATIONS

Jian Gang Zhang, Carol A. Kruse, Laura Diggers, Heil Hoa, Jeffery Wisoff, Jeffery C. Allen, Daivd Zagzag, Elizabeth W. Newcomb & Martin R. Jadus, Tumor Antigen Precurson Protein Profiles of Adult and Pediatric Brain Tumors Identify Potential Targets for Immunotherapy, J. of Neurooncology (2008) 88:65-76.

Jian Gang Zhang, Junichi Eguchi, Carol A. Kruse, German G. Gomez, Habib Fakhrai, Stephanie Schroter, Wenzue Ma, Neil Hoa, Boris Minev, Christina Delgato, H. Terry Wepsic, Hideho Okada, and Martin R. Jadus, Antigenic Profiling of Glioma Cells to Generate Allogeneic Vaccines or Denedritic Cell-Based Therapeutics, Clin. Cancer Research (2007) 13(2): 566-575.

Clawson C, Huang CT, Futalan D, Martin Seible D, Saenz R, Larsson M, Ma W, Minev B, Zhang F, Ozkan M, Ozkan C, Esener S, Messmer D., Delivery of a Peptide via Poly (D,L-lactic-co-glycolic) Acid Nanoparticles Enhances its Dendritic Cell-Stimulatory Capacity, Nanomedicine. Oct. 2010: 6(5):651-61. Epub Mar. 27, 2010.

Yucheng Tang, Hakan Akbulut, Jonathan Maynard, Line Petersen, Xiangming Fang, Wei-Wei Zhang, Xiaoqin Xia, James Koziol, Phyllis-Jean Linton, and Albert Deisseroth, Vector Prime/Protein Boost Vaccine That Overcomes Defects Acquired during Aging and Cancer, The Journal of Immunology, 2006, 177: 5697-5707.

Hickey, M.J., Malone, C., Erickson, K., Jadus, M.R., Prins, R.M., Liau, L.M., Kruse, C.A., Cellular and Vaccine Therapies for Gliomas, J. Transl. Med. (2010), 8:100.

Company Fact Sheet, Immatics Biotechnologies, Sep. 2010.

Zhang et al., Antigenic profiling of glioma cells to generate allogeneic vaccines or dendritic cell-based therapeutics, Clinical Cancer Research, vol. 13, pp. 566-575, Jan. 25, 2007 See: Abstract; p. 567, left column, second paragraph; p. 572; Figs. 1, 2 and Tables 1-3.

Slavcev et al., Estimates of cytotoxic T-lymphocyte precursor frequencies against HLA Class I antigens in responder-stimulator pairs with a negative mixed lymphocyte culture reaction, Human Immunology 44, 97-102, Oct. 1995 The whole document.

Fujiwara et al., Tissue-restricted T cell alloresponses across HLA barriers: selection and identification of leukemia-restricted CTL in HLA-mismatched stimulator-responder pairs, Bone Marrow Transplantation (2003) 32, 371-378, Aug. 2003 The whole document.

Patent Cooperation Treaty, International Search Report, Sep. 16, 2011.

Duquesnoy R, HLAMatchmaker: a molecularly based algorithm for histocompatibility determination. I. Description of the algorithm, Human Immunology, vol. 63(1), pp. 339-352 (2002).

Dankers MK et al., HLAMatchmaker is not a suitable tool to predict the alloreactive cytotoxic T-lymphocite response in vitro, Transplantation, vol. 78(1), pp. 165-167 (2004).

Duquesnoy R et al, HLAMatchmaker-defined triplet matching is not associated with better survival rates of patients with class I HLA allele mismatched hematopoietic cell trasnplanats from unrelated donors, Biology of blood and bone marrow transplantation, vol. 14(9), pp. 1064-1071 (2008).

Marijt et al, Phase I/II feasibility study evaluating the generation of leukemia-reactive cytotoxic T lymphocyte lines for treatment of patients with relapsed leukemia after allogeneic stem cell transplantation, Haematologica, vol. 92, pp. 72-80.

Falkenberg J H F et al, Falkenburg J H F et al, Complete Remission of Accelerated Phase Chronic Myeloid Leukemia by Treatment With Leukemia-Reactive Cytotoxic T Lymphocytes, Blood, American Society of Hematology, US, vol. 94, No. 4, Aug. 15, 1999, pp. 1201-1208, XP002908496, * p. 1202-p. 1203 *.

Jedema Inge et al, Early detection and rapid isolation of leukemia-reactive donor T cells for adoptive transfer using the IFN-gamma secretion assay, Clinical Cancer Research : An Official Journal of the American Association for Cancer Research Jan. 15, 2007, vol. 13, No. 2 Pt 1, Jan. 15, 2007, pp. 636-643, * p. 637 *.

Montagna Daniela et al: Generation and ex vivo expansion of cytotoxic T lymphocytes directed toward different types of leukemia or myelodysplastic cells using both HLA-matched and partially matched donors, Experimental Hematology (New York), vol. 31, No. 11, Nov. 2003, pp. 1031-1038, * p. 1033 *.

Lee J J et al: "Monocyte-derived dendritic cells from HLA-matched allogeneic donors showed a greater ability to induce leukemic cell-specific T cells in comparison to leukemic cell-derived dendritic cells or monocyte-derived dendritic cells from AML patients", Leukemia Research, New York,NY, US, vol. 32, No. 11, Nov. 1, 2008, pp. 1653-1660, p. 1655-p. 1656 *.

Tinckam et al, Histocompatibility methods, Transplanatation Reviews, Grune & Stratton, Orlando, FL, vol. 23, No. 2, (2009), pp. 80-93.

* cited by examiner

FIG. 1

HLA types of responding brain tumor patients (BTP) and alloCTL donors: eplet number/type mismatch assessed by HLAMn

| Brain Tumor Patient | Brain Tumor Patient HLA | | | Donor | HLA Type of Donor | | | | No. Eplet Mismatches between Responder Patients & AlloDonors | No. Eplet Mismatches between Responder Patients & Donors | Mismatched Eplets common to responders or found frequently patient:donor pairs | | | | | | | | | | |
|---|---|---|---|---|---|---|---|---|---|---|---|---|---|---|---|---|---|---|---|---|---|
| BTP3 | A*2402 | A*3101 | B*0702 | B*1516 | D1 | A*0101 | A*0201 | B*0801 | B*1801 | 19 | | 9T | 56R | | 73ID | 76ERI | 113YQ | | | | 166DG |
| | | | | | D2 | A*0201 | X* | B*0702 | B*1501 | 18 | 99 | 9T | 56R | 62QE | 73ID | 76ERI | 113YQ | 116D | 142MI | 144TKR | 151RV | 166DG |
| | | | | | D3 | A*0201 | A*0301 | B*4402 | B*5101 | 20 | | 9T | 56R | | 73ID | | 113YQ | | | | | 166DG |
| | | | | | D4 | A*1101 | A*2601 | B*0702 | B*4001 | 19 | | 9T | 56R | | 73ID | 76ERI | | | | | | 166DG |
| | | | | | D5 | A*0301 | X | B*0801 | B*1302 | 23 | | 9T | 56R | | 73ID | 76ERI | 113YQ | | | | | |
| BTP4 | A*3101 | A*3201 | B*4901 | B*4001 | D1 | A*0101 | A*0301 | B*0702 | B*5701 | 19 | 42 | 9T | 56R | | 73ID | | 113YQ | | | | | |
| | | | | | D2 | A*0201 | X | B*1501 | X | 23 | | 9T | 56R | 62QE | 73ID | 76ERI | 113YQ | 16D | 142MI | 144TKR | 151RV | 166DG |
| BTP5 | A*0101 | A*0201 | B*0801 | B*4402 | D1 | A*0201 | A*0301 | B*0702 | X | 26 | 117 | | | | | | | | | | | 166DG |
| | | | | | D2 | A*0301 | A*3101 | B*3601 | B*5101 | 28 | | | | | | | | | | | | 166DG |
| | | | | | D3 | A*2601 | A*2902 | B*2705 | B*4101 | 23 | | | | 62QE | | | | | | 144TKR | | 166DG |
| | | | | | D4 | A*0101 | A*2601 | B*1302 | B*2705 | 22 | | | | | | | | | | | | |
| | | | | | D5 | A*0101 | A*6801 | B*0702 | B*1402 | 18 | | | | | | | | | | | 151RV | | a. X indicates that the person was homozygous at the HLA locus.

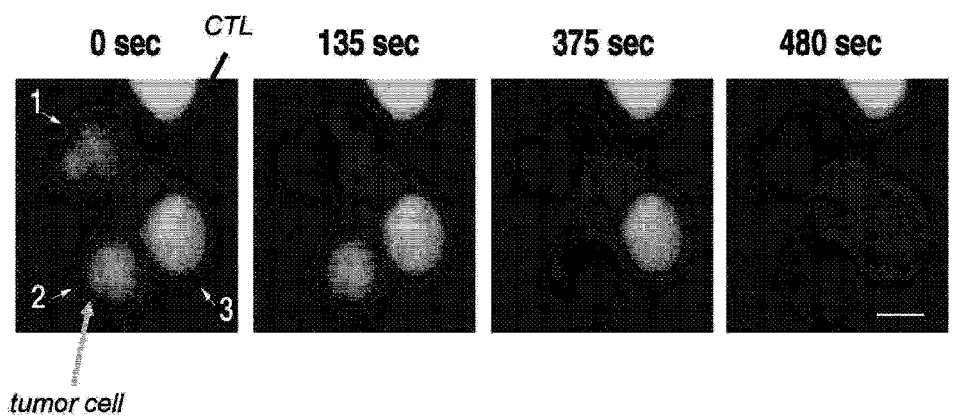
FIG. 10A
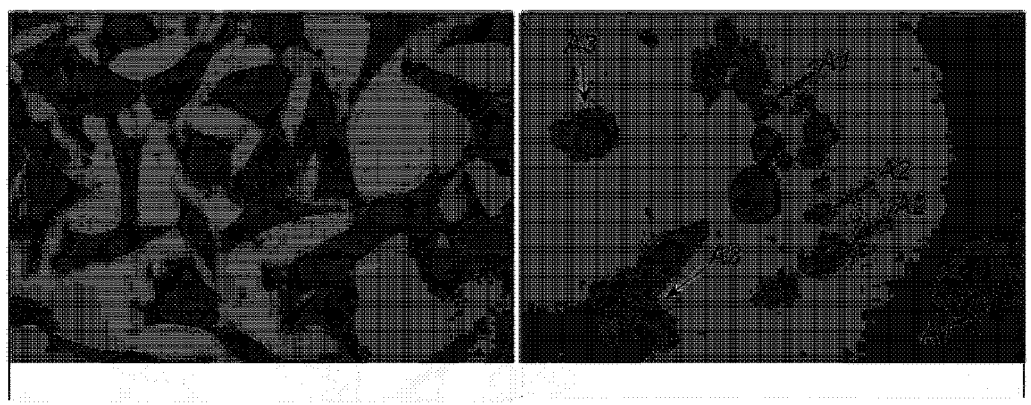
FIG. 10B
FIG. 10C

The lytic acctivity by gp100-specific TIL effectors to target cells: non-loaded T2 target cells or gp100 peptide-loaded T2 cells, HLA-A2-positive human glioma cell lines (T98G, LN-18, U251, U373) or HLA-A2-negative human glioma cell line LN-229

| Symbol | Target Cell | CTL Induction |
|---|---|---|
| □ | T2, no peptide | Peptide alone |
| ■ | T2, no peptide | NP-peptide |
| ○ | T2 + peptide | Peptide alone |
| ● | T2 + peptide | NP-peptide |
| △ | 624 | Peptide alone |
| ▲ | 624 | NP-peptide |
| ▽ | 1351 | Peptide alone |
| ▼ | 1351 | NP-peptide |

PAIRING PROCESSES FOR PREPARING REACTIVE CYTOTOXIC T CELLS

CROSS-REFERENCE TO RELATED APPLICATIONS

The present application is a continuation-in-part of patent application Ser. No. 12/844,668 filed on Jul. 27, 2010, which claims priority to provisional patent applications Ser. No. 61/229,229 filed on Jul. 28, 2009 and Ser. No. 61/229,233 filed on Jul. 28, 2009. The present application also claims priority to provisional patent application Ser. No. 61/372,067 filed on Aug. 9, 2010. Each of these patent applications is incorporated herein in its entirety.

FIELD OF THE INVENTION

The present invention relates, in one aspect, to a method of pairing patient cells and donor cells to prepare reactive cytotoxic T cells, which can be administered to a patient for treating certain disorders, such as cancer (for example, brain cancer).

BACKGROUND OF THE INVENTION

T cells can be activated by an antigen presenting cell. An activated T cell can bind to a cell that presents an antigen to which the T cell was activated via an interaction between a T cell receptor and major histocompatibility complex (MHC), and the activated T cell can kill the cell to which it is bound.

It is possible to activate T cells from a donor against cells from a patient and generate cytotoxic T cells that kill patient cells. Such T cells are referred to as "alloreactive" T cells as they are activated from donor cells and are active against the MHC antigens (sometimes identified as human leukocyte antigens or HLA) present on patient cells.

Alloreactive cytotoxic T cells can be prepared by isolating blood from a patient, separating white blood cells, and inactivating them. These inactivated patient cells can be mixed with white blood cells from a donor in a one-way mixed lymphocyte reaction.

In the lymphocyte reaction, T cells among the donor cell population are activated against antigens presented by cells in the patient population, and activated cytotoxic T cells are generated against the patient cells. The activated cytotoxic T cells can be collected and administered to the patient. Cells in the patient, such as cancer cells, that display antigens recognized by the cytotoxic T cells will be killed.

Although alloreactive T cells can effectively kill targeted cells, they may be targeted themselves by the patient's immune system.

Alloantibody response can be predicted in transplantation settlings by using the HLAMatchmaker (HLAMm) algorithm. HLAMm operates by finding permissible mismatches between molecularly HLA-type donors and recipients such to minimize rejection. When HLAMm is applied to the diverse HLA repertoire, it is able to predict B cell driven alloantibody generation following organ transplantation.

Unfortunately, the current algorithm does not predict reliably the T cell induced graft-versus host (GVH) disease.

SUMMARY OF THE INVENTION

In one aspect, the present invention relates to a method of pairing a patient with one or more donors and of inducing reactive cytotoxic T cells, which can then be administered to the patient to treat certain disorders such as a cancer. The reactive T cells may be induced by using the patient's own immune cells.

One advantage of the present invention is to provide improved compositions and methods to prevent GVH disease.

Another advantage of the present invention is to provide improved compositions and methods to treat cancer, regardless of whether the cancers is situated in an immune-privileged site or not.

Methods described herein involve the identification of the presence or absence of a partial mismatch between antigen information, or information determined from antigen information, from patient and donor cell pairs. According to the invention, such partial mismatch is predictive on an enhanced immune response in the patient. Once a pairing is identified based on such a partial mismatch, reactive cytotoxic T cells can be induced, which, among other things, have a stronger immunogenic activity than those produced from a pairing for which the partial mismatch is not present. Thus, a method according to the invention enables the identification of optimal patient/donor matches for pairing cells from each and for preparing reactive cytotoxic T cells. These types of methods or processes are referred to herein as "pairing processes."

In an exemplary method according to the invention, patient cell and donor cell pairs that are suitable for inducing reactive cytotoxic T cells are identified by first providing patient cell information, which includes patient cell antigen information determined at least partly through serotyping or a high or intermediate resolution molecular sequencing method of MHC information. In other steps of this method, stimulator information from the patient cell antigen information is generated and compared to responder information generated from donor cell antigen information, also determined at least partly through serotyping or a high or intermediate resolution molecular sequencing method of MHC information.

The presence or absence of a partial mismatch between the stimulator information and the responder information is identified among patient cell and donor cell pairs, and a patient cell and donor cell match is selected for the preparation of reactive cytotoxic T cells based on the presence of the partial mismatch.

In another step of this exemplary method, reactive cytotoxic T cells are induced. This occurs because immune cells endogenous to the patient (which includes cells from the patients or derived from patient cells) respond to stimulator antigen derived from the donor and induce the reactive cytotoxic T cell reaction based on the patient cell and donor cell pair.

In different embodiments of this method, antigen information includes HLA class I antigen information and/or HLA class II antigen information.

In one embodiment, the T cells are derived from the donor and the stimulator cells are derived from the patient. In another embodiment, the T-cells are derived from the patient and the stimulator cells are derived from the donor.

In one embodiment, patient or donor cell antigen information is determined at least partly through a high or intermediate resolution molecular DNA sequencing method. In another embodiment, patient or donor cell antigen information is determined at least partly through a high or intermediate resolution molecular RNA sequencing method. In still another embodiment, patient or donor cell antigen information is determined at least partly through a high or intermediate resolution molecular protein sequencing method.

In different embodiments of the invention, the high or intermediate resolution molecular sequencing method includes one or more of a sequence based typing (SBT) method, a sequence specific primer (SSP) method, a restriction fragment length polymorphism (RFLP) method, or sequence specific oligonucleotide (SSO) or restriction fragment length polymorphism (RFLP) method.

In certain embodiments, T cell receptor interaction information includes eplet information. For example, partial mismatches may be determined by the number or types of mismatched eplets.

In other exemplary methods according to the invention, the patient or donor cell antigen information may be derived from one or more cell types, for example, from monocytes, antigen presenting cells, dendritic cells, lymphocytes, lymphoblasts, T cells, or the patient's tumor cells.

In still other exemplary methods according to the invention, the stimulator is a tumor associated antigen (TAA) such as whole tumor cells, DNA/RNA either conjugated or not to liposomal membrane proteins, tumor cell lysates or homogenates, established tumor cell lines, or synthetic peptides or fragments therein.

The presence or absence of a partial mismatch between the stimulator information and the responder information may be identified with a computer algorithm. Such algorithm may be configured to provide structurally based HLA matching, such as a version of the HLAMm, and may include a string matching algorithm. This computer algorithm may be trained using a training set and may perform a statistical analysis on the training set, for example, a log-rank test.

An exemplary method according to the invention may also include the step of exposing the cells of the patient to conditions that generate inactivated patient cells. Those conditions may include radiation and mitomycin C. The step of detecting the presence or absence of cytotoxic T cell activation may also be included in such exemplary method, for example, by identifying the presence or absence of an activated T cell marker or of interferon gamma.

Certain embodiments of the invention may include also the step of determining the ratio of T helper 1 to T helper 2 cytokines.

In another aspect, the invention provides a method of treating a patient that has a cancer, for example, a brain tumor such as a glioma. The tumor can be primary or metastatic.

In an exemplary method according to the invention, cells that have been subjected to an activation reaction may be administered to an immuno-privileged site of the patient such as the brain. In certain embodiments, the cytotoxic T cells are purified prior to being administered to the patient. It should be understood, however, that the invention includes methods and compositions for treating different types of cancers and in different parts of a human or animal body, as well as other types of conditions that may not ordinarily be treatable due to rejection by the patients of cells administered thereto.

An exemplary method according to the invention may include the additional step of detecting the presence or absence of cytotoxic T cell activity in the patient. For example, the presence or absence of cancer reduction in the patient may be evaluated. In some embodiments of the invention, cytotoxic T cell activation and/or cytotoxic T cell activity may be compiled in a training set for the algorithm.

Additional aspects and embodiments of the invention can be found in the following description, examples, claims and drawings.

BRIEF DESCRIPTION OF THE DRAWINGS

The drawings illustrate embodiments of the invention and are not limiting. For clarity and ease of illustration, the drawings are not made to scale and, in some instances, various aspects may be shown exaggerated or enlarged to facilitate an understanding of particular embodiments.

FIG. 1 shows Human Leukocyte Antigen (HLA) types of responding brain tumor patients (BTP) and alloreactive cytotoxic T lymphocytes (alloCTL) donors:eplet number/type mismatch assessed by an algorithm.

FIG. 10A shows that, in some embodiments, cytotoxic T lymphocytes (CTL) can rapidly lyse tumor cells, while FIGS. 10B-10C show a 13-06-MG glioma cell monolayer treated with anti-13-06 aCTL and the control, and the resulting apoptosis of the glioma cells.

DETAILED DESCRIPTION OF EMBODIMENTS OF THE INVENTION

Figure 2:
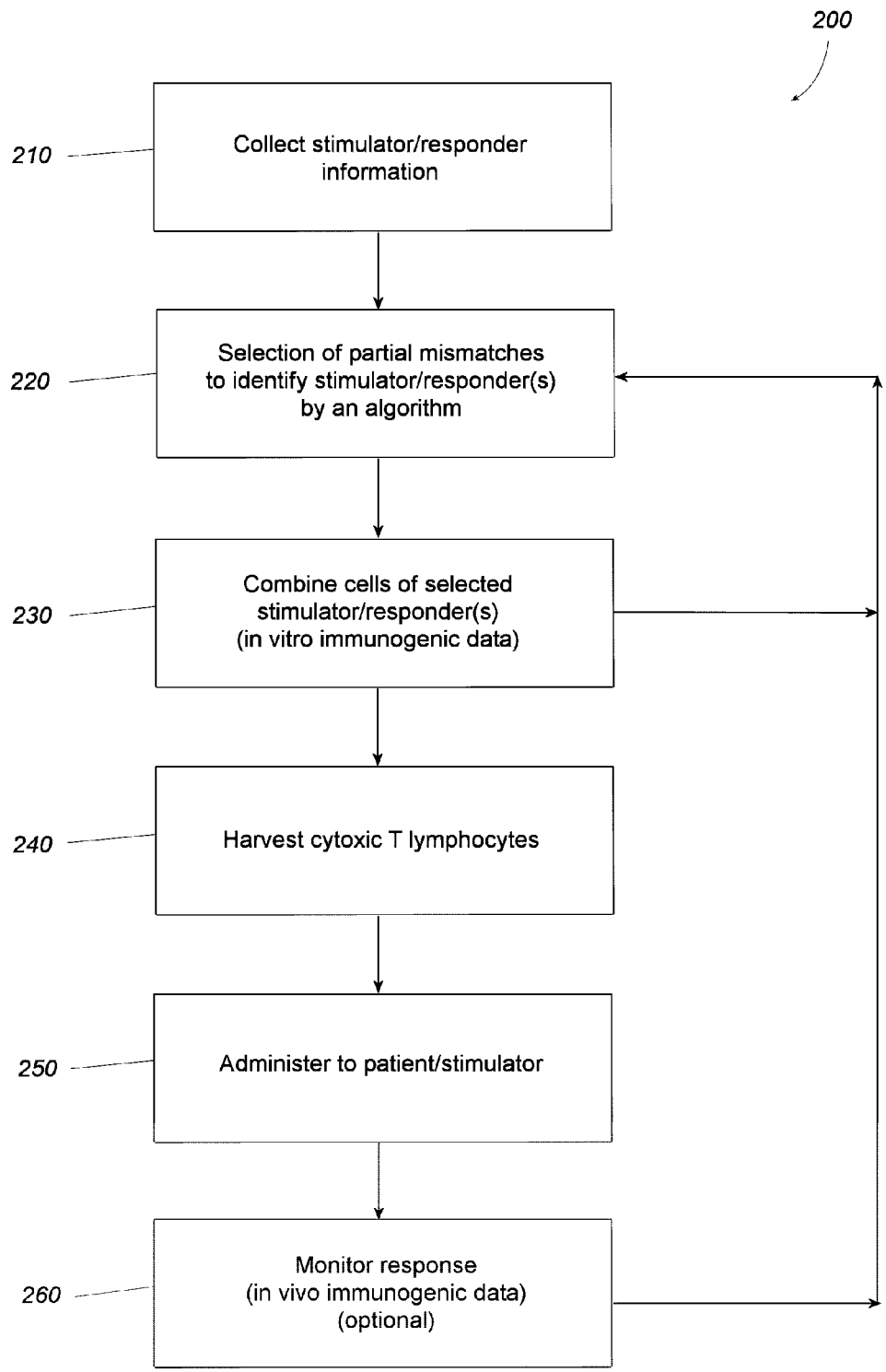
FIG. 2 shows a flowchart of an exemplary method described herein.

The following detailed description relates to representative embodiments of the invention. It is to be understood, however, that the present invention may be embodied in various forms. Therefore, the specific details disclosed herein are not to be interpreted as limiting, but rather as a representative basis for teaching one skilled in the art how to employ the present invention in virtually any detailed system, structure, or manner.

Brain tumor cells, such as glioma cells, express human leukocyte antigens (HLA, major histocompatibility complex antigens or MHC), whereas HLA are generally not expressed on normal, mitotically quiescent neuroglia. Therefore, the HLA expressed by the glioma cells can act as therapeutically useful tumor directed antigens. The lack of expression of HLA antigens on normal brain tissues may limit the immune reaction only to tumor cells. In addition, the relative immune privilege of the brain can extend the useful life-span of therapeutic alloCTL.

Alloreactive cytotoxic T lymphocytes (alloCTL) are T cells activated against allogeneic HLA. The immune responses to major alloantigen are stronger than those engendered to minor tumor associated antigens (TAA), and the CTL precursor frequencies generally are higher to major alloantigens than to TAA.

In one aspect, the present invention teaches methods and treatments, by which alloCTL adoptively transferred into an organ of a patient can induce destruction of tumor cells, such as tumor cells (for example, brain tumor cells).

For generating robust alloCTLs, a responder:stimulator pairing is predicted by methods and compositions described herein. Any responder:stimulator (i.e., a healthy donor providing precursor CTL:patient) pairing prediction can be performed. In one embodiment, a patient's irradiated white blood cells displaying HLA are used as stimulator while the donor's white blood cells are used as responders. Any prediction method can be used on any type of data from the patient and/or donor. For example, a prediction method can incorporate use of an algorithm, statistics, modeling, a simulation in vitro or in silico or any combination thereof.

Patient and Donor Antigen Information

Patient cell antigen information (also referred to herein as "patient antigen information") and donor cell antigen information (also referred to herein as "donor antigen information") can be any suitable antigen information useful for determining immunologic pairing for the preparation of cytotoxic T cells.

In certain embodiments, major histocompatibility complex (MHC) information, which also is referred to as human leukocyte antigen (HLA) information, is provided. HLAs are encoded by the HLA loci on human chromosome 6p. HLA information includes, without limitation, HLA class I information, HLA class II information, a combination of both, and any other suitable antigen information. HLA class I molecules often present peptides about 9 amino acids in length, and HLA class II molecules often present peptides about 15-24 amino acids in length. HLA class I molecules often present peptides from within the cell, and HLA class II molecules often present peptides from a source outside the cell that is brought into the cell for presentation. An HLA molecule can interact with a CD8+ activated T cell that recognizes the peptide presented by the HLA molecule, and the T cell can kill the cell bearing the HLA molecule with which the T cell interacts.

There are different groups of HLA class I molecules that include, without limitation, HLA-A, HLA-B, HLA-C, HLA-DR, DP, DQ; HLA-E, HLA-F, HLA-G, and HLA-K groups. Each group of HLA class I molecules includes multiple alleles (one paternal and one fraternal). For example, HLA-A*0101, *0102, *0103, . . . *0130 are assigned to the serotype A1. The "A*01" prefix signifies that the gene products (expressed proteins) of the alleles are primarily identified by the A1 serotype or most similar to alleles recognized by the serotype. There are different groups of HLA class II molecules that include, without limitation, HLA-DM, HLA-DQ, HLA-DP, HLA-DO and HLA-DR groups. Each group of class II molecules encodes alpha-beta heterodimer proteins, and includes multiple alleles. For example, the HLA-DR group of HLA class II molecules includes DRB1*0101, DRB1*0102, DRB1*0103 and other alleles. For mammalian patients and donors (e.g., humans), each patient and donor cell bears two alleles in each group. Thus, patient and donor cells each have two HLA-A alleles, two HLA-B alleles and so on.

Patient and donor antigen information sometimes are referred to herein as "antigen units," and each antigen unit sometimes is an allele. Antigen information is one or more alleles in certain embodiments, and in some embodiments is between about 2 to about 38 alleles. Antigen information sometimes includes one allele for each HLA group provided, or both alleles of each HLA group provided. In some embodiments, antigen information includes one or two alleles from HLA groups (e.g., about 1 to about 19 HLA).

Methods for determining an HLA allele are known in the art. For example, an HLA allele can be determined by methods that include, but are not limited to, molecular typing, haplotyping, gene sequencing, cellular typing and serotyping. In molecular typing methods, for example, an amplification reaction (e.g., polymerase chain reaction, or PCR), can be utilized with sequence specific primers (SSPs), where the size of an amplification product, and/or a sequence in or of an amplification product, can be assessed to determine an HLA type (e.g., HLA allele). The latter method sometimes is referred to as SSP-PCR when PCR is utilized as the amplification process. A molecular typing method, in some embodiments, can involve identification of a sequence in or of a product of an amplification reaction (e.g., sequence base typing (SBT)). In SBT an amplification product sometimes is immobilized and contacted with sequence specific primers to determine a sequence of the product. Molecular typing also can be accomplished in some embodiments by a restriction fragment length polymorphism (RFLP) method in which one or more amplification products are digested with one or more enzymes, and the resulting fragments are analyzed. In molecular typing methods that utilize an amplification reaction, nested amplification reactions can be utilized in some embodiments. Haplotyping often involves determining multiple HLAs on one nucleic acid strand of a subject. Gene sequencing methods generally involve sequencing all or a part of an HLA from a patient or donor using known sequencing methodology (e.g., SBT-PCR). Serotyping often involves reacting cells from a patient or donor with blood, antiserum and/or an antibody and determining which HLA antigens are present in the cell. In serotyping procedures, a cross-reacting HLA antigen can be recognized by monospecific antibodies (e.g., monoclonal or polyclonal) in certain embodiments. A cellular typing method, such as a mixed lymphocyte culture (MLC or MLR) method, can be used to determine presence of an HLA allele by selective activation of a particular T cell type. In some embodiments, a molecular typing method (e.g., SSP-PCR, SBT and/or RFLP methods) is utilized to generate antigen information for a donor and/or patient, and in certain embodiments, antigen information from a donor and/or a patient is obtained, or is complemented, with a cellular typing and/or cellular typing method.

In some embodiments, antigen information is from a donor who is unrelated by family relationship to the patient. The donor may be related by family relationship to the patient in certain embodiments, and may be, for example, a sibling, parent, grandparent, uncle, aunt, child, grandchild, niece or nephew of the patient. In some embodiments, the donor is not a sibling of the patient.

Stimulator and Responder Information

Stimulator information is related to patient cell antigen information and responder information is related to donor cell antigen information. Stimulator information and responder information are related to antigen information, and often are derived or calculated from antigen information. Stimulator information and responder information includes amino acid differences, i.e., mismatch information derived from comparison of individual HLA alleles.

Stimulator information and responder information sometimes are T cell receptor interaction information, which can be a peptide subsequence that interacts, or is calculated to interact, with a T cell, in certain embodiments. Such information in the latter embodiments sometimes is referred to as "eplet" information. Stimulator and responder information sometimes is referred to herein as "stimulator/responder units," and each unit can be an eplet in certain embodiments.

Epitopes are antigenic determinants that elicit an immune response. Some epitopes are hidden (cryptotopes) that become immunologically available after fragmentation or denaturation of an antigen, for example. A paratope involves a large group of surface residues that are involved in binding to an antigen. There are two groups of protein epitopes, (1) continuous (or linear) epitopes involving a single continuous amino acid sequence and (2) discontinuous epitopes that comprise amino acids separated in the primary sequence but clustered together on the molecular surface by folding the native protein. Mapping studies of antibody reactivity patterns with natural variants and mutated protein antigens have generated information about the location of epitopes and have also suggested that epitopes can generally be defined by small numbers of amino acid residues. A public epitope is an antigenic region of amino acids that is antibody accessible. A private epitope is not accessible by antibody, but may be accessible via HLA; cell receptors (TCR) interactions.

Eplets often are configurations of polymorphic amino acid surface residues (triplets or patches) or small structural epitopes that play a dominant role in determining recognition by a specific antibody. These residues/triplets/patches often are within a 3 to 3.5 Angstrom radius from each other. Stimulator and responder eplet information can provide a more rigorous standard than serological HLA typing alone. Eplet information along with other serological, protein and/or molecular information can also be used in combination.

Direct alloreactivity can be observed when T cells restricted to one HLA molecule are exposed to antigen presenting cells bearing a peptide sequence from a different, but related HLA molecule. Many of the contacts involved in T-cell receptor antigen recognition involve binding of T-cell receptor elements to the HLA antigen-presenting face (for example HLA alpha helices 1 and 2), and because of allelic structural differences, the binding of the stimulator alloHLA to a T-cell receptor on a responder may be with greater affinity than to recognize self-HLA. Additionally, amino acid substitutions in the antigen (or peptide) binding groove of HLA can contribute to alloreactivity. In certain embodiments, methods described herein investigate HLA residues on the T-cell receptor "docking" face that are exposed and capable of taking part in direct T-cell receptor binding, and HLA residues lining the HLA antigen-binding groove, that are capable of participating in antigen binding. Since the enhanced affinity of the T-cell receptor for alloHLA+peptide may result from (a) changes in T-cell receptor/HLA interactions (i.e., HLA helices 1 and 2), (b) changes in T-cell receptor/peptide interactions (i.e., peptide binding groove), or (c) a combination of these, an algorithm is used to look at these two classes of allelic changes first separately, then in combination, seeking predictive correlations between structural differences and allostimulation potential. In some embodiments, methods described herein are able to develop "partial mismatch scoring" procedures for related HLA alleles that will be predictive of alloresponses associated with the mismatch. Understanding of the structural and functional basis of T cell alloreactivity is useful in choosing responders that will provide functionally robust alloCTLs based on HLA partial mismatch information from stimulator and responders.

The assignment of antibody-accessible (B cell alloresponse occurs because of three-dimensional or conformational differences), or T-cell receptor accessible, positions is based on a detailed description of the crystalline structure of various HLA class I and II molecules, likely on the alpha helices and beta sheet of HLA. In certain embodiments, polymorphic triplets in the antibody-accessible positions of amino acid sequences are serologically defined as those that are recognized by alloantibody. Each triplet or patch is designated by its amino acid composition around a given position in the amino acid sequence.

Certain triplets/patches exhibit high immunogenicity whereas others have intermediate or low immunogenicity. The total number of mismatches on the face of the HLA and/or the type of amino acid (aa) differences is important for determining immunogenicity.

Comparison of stimulator and responder information can be based on linear sequences of amino acids or patches of residues in linear and discontinuous sequences as motifs for potentially immunogenic epitopes. An HLA mismatch between the responder and stimulator is assessed by determining the number of amino acids not shared between the responder and stimulator's HLA antigens, in some embodiments.

The HLA molecules can be categorized into groups according to the potential of being recognized as non-self or self when the patient is exposed to an HLA mismatch. For example, one group can consist of triplets/patches that are present in one or two HLA antigens. Another group can consist of polymorphic triplets/patches that are shared between three or more HLA antigens encoded by the same class I or class II locus, for example. Another group can consist of triplets/patches that are polymorphic for one class I locus but monomorphic for another class I locus, for example. Such triplets/patches may not represent immunogenic epitopes because they are always present on the patient's own HLA antigens. Another group can consist of triplets/patches that are polymorphic for one, two or all three HLA, A, B, and C loci for class I antigens, for example. The translation of HLA with and expression by cells can also vary and influence immune response.

Stimulator and responder information also can be gained from in vitro experimentation. Some molecules are produced at higher levels or lower levels in patients with rejected transplants or grafts. Some molecules are produced at higher levels or lower levels in patients with stable transplants or grafts. Assaying for these types of molecules in an in vitro experiment can also generate stimulator and responder information. For example, a higher number of donor-specific interferon (IFN)-γ producing cells (proinflammatory, T-helper 1 cytokine) can be found in patients with rejected transplants or grafts. Also a higher number of interleukin (IL)-10 producing cells (anti-inflammatory, T-helper 2 cytokine) are found in patients with stable transplants or grafts. By way of example, use of the number of IFN-γ producing cells and/or interleukin IL-10 and/or a ratio of both can be used to identify appropriate stimulators and/or responders.

Selection of a mismatch can depend on the antibody specificity repertoire of the sensitized patient. HLA mismatch acceptability may also be assessed with information about the immunogencity of certain polymorphisms. For example, highly sensitized patients can produce a limited repertoire of alloantibodies specific for the more common HLA epitopes. Although most highly sensitized patients have been exposed to many mismatched alloantigens, their antibody reactivity patterns reveal specificity to a relatively small number of immunogenic triplets/patches, whereas other triplets/patches do not induce an antibody response and, therefore, must be non-immunogenic for the patient. The generation and application of information about immunogenicity of mismatched HLA can be used as stimulator/responder information.

Other stimulator/responder immunogenicity information which can be considered is the structural basis of antibody-antigen interactions such as contact areas and binding energy. The binding energy of an antigen-antibody complex is primarily mediated by a small subset of contact residues in the epitope-paratope interface. Substitutions of such "energetic" residues as seen in naturally occurring antigenic variants or induced by site-directed or alanine scanning mutagenesis lead often to dramatic decreases in the binding of antigen to antibody. Mapping studies have located energetic residues in "hot spots" of epitopes and paratopes, i.e. regions made up of small numbers of residues that contribute most of the binding energy. Energetic residues often are located in the center of the epitope-paratope interface.

Other stimulator/responder immunogenicity information can include, without limitation, conventional serological cross-reactive group (CREG) mismatching (mm) (e.g., HLA-A, HLA-B, and any other suitable allele), any applicable/related HLA mismatching, HistoCheck, HLA-DR or DQ mismatching, pretransplantation percent-reactive antibody (PRA), recipient and donor race and donor age, and cold ischemia time. Such information can be used instead of eplet information or supplement eplet information, in some embodiments.

The acronym HLA CREG refers to serological cross-reactive group to any applicable HLA molecule and describes how a monospecific HLA antisera can react with two or more HLA antigens. The serologic cross-reactivity is assigned to determinants (public epitopes) that are differentially shared among HLA class I (or class II) gene products. For example, HLA-A and HLA-B gene products can be grouped into eight or more families of CREG based upon serologic cross-reactivity patterns, associative analyses, or shared amino acid sequence polymorphisms. Potential responders and stimulator pairs may be matched for public epitopes even though they are mismatched for the private epitopes that confer unique differences between class I HLA molecules. Thus, there are levels of immunologic matching of HLA gene products ranging from the allele level, in which all public and private epitopes are matched, to the CREG level, in which public epitopes are matched but private epitopes are mismatched, in some embodiments.

The HistoCheck webtool similarly is a way of visualizing and understanding the structural differences among related major histocompatibility complex molecules. Because exact HLA matching often is not possible for organ transplant pairings, HistoCheck allows for the identification of which alleles present the same structures (HLA-peptide complexes) to certain T-cell receptors despite having different amino acid sequences. HistoCheck is a tool that provides a summary of amino acid mismatches, positions, and functions as well as 3-dimensional visualizations.

The HistoCheck tool applies a distance index referred to as a Risler index. Similarity between single pairs of exchanged amino acids is measured by this distance matrix, as proposed by Risler J L, Delorme M O, Delacroix H, Henaut A, Amino acid substitutions in structurally related proteins: A pattern recognition approach. Determination of a new and efficient scoring matrix, J Mol Biol 1988; 204: 1019-1029. A basic idea behind a Risler index score is that two distinct amino acids are less dissimilar the more often they are substituted for each other in functionally related proteins. Accordingly, the fewer a pair of amino acid substitutes each other, thus representing functional dissimilarity, the higher the score yielded, with the maximum value of 100.

Partial Mismatch and Methods for Identification

The presence or absence of a partial mismatch (e.g., one or more mismatches) between (i) patient antigen information and/or stimulator information, and (ii) donor antigen information and/or responder information, often is identified in methods described herein. A partial mismatch is not a full match and often is a lower degree of matching than for an organ donor-patient pairing. A partial mismatch is a greater degree of matching than a total mismatch.

In embodiments where antigen units are compared, a partial mismatch sometimes is 1, 2, 3, 4, 5 or 6 patient/donor antigen units mismatched short of a full match in some embodiments, and in certain embodiments, a partial mismatch sometimes is 1, 2, 3, 4, 5 or 6 patient/donor antigen units matched short of a full mismatch. In embodiments where stimulator/responder units are compared, a partial mismatch sometimes is 1, 2, 3, 4, 5 or 6 stimulator/responder units mismatched short of a full match in some embodiments, and in certain embodiments, a partial mismatch sometimes is 1, 2, 3, 4, 5 or 6 stimulator/responder units matched short of a full mismatch.

In certain embodiments, a partial mismatch is one or more amino acid differences between corresponding HLA molecules of a donor and patient (e.g., 1, 2, 3, 4, 5, 6, 7, 8, 9, 10 amino acids that differ between an HLA allele of a donor and patient). A partial mismatch may be amino acid differences between one or more corresponding HLA types of a donor and patient (e.g., one or more of HLA-A, HLA-B, HLA-C, HLA-DQ, HLA-DR, HLA-DP), where a corresponding HLA type is HLA-A allele of donor to HLA-A allele of patient, for example.

Identifying the presence or absence of a partial mismatch may be conducted by hand or by an algorithm, or a combination of the foregoing. In certain embodiments, provided are algorithms designed to identify partial mismatches between stimulators and responders. Algorithms can make use of the following information, in some embodiments: (1) each HLA antigen representing a distinct string of polymorphic triplets or patches of residues in linear and discontinuous regions as potential immunogens that can induce specific alloantibodies, and (2) sensitized patients do not have alloantibodies against triplets/patches present on their own HLA molecules. The algorithm can assess stimulator and responder compatibility through intralocus and interlocus comparisons and determine which amino acid mismatched HLA between donor and patient. This analysis can consider each responder (donor) HLA antigen mismatch toward one or more particular HLAs in some embodiments, and in certain embodiments, a mismatch towards an entire class I (e.g., HLA-A, HLA-B, HLA-C) and/or class II (e.g., HLA-DR, HLA-DP, HLA-DQ) phenotype of the stimulator (patient), or subset thereof, in some embodiments. It should be noted that, in general, gliomas express class I but little class II antigen, so it may be inferred that the efficacy seen in patients in the small pilot study indicates class I CTL involvement.

The term "intralocus" as used herein refers to triplet/patch sharing between different HLA antigens encoded by the same locus, for example comparing loci on HLA-A from stimulator and responder. The term "interlocus" as used herein refers to triplet/patch sharing between HLA antigens encoded by different loci, for example comparison can be from a HLA-A locus from the stimulator and a HLA-B locus from the responder, for example. The latter includes triplets/patches that are polymorphic at one locus but monomorphic at another locus.

An algorithm can factor the structural basis of an HLA antigen partial mismatch utilizing intralocus and interlocus comparison of strings of amino acid triplets/patches on antibody-accessible sties of HLA class I and/or II molecules. The triplets/patches are elements of epitopes that can induce the formation of specific antibodies. This algorithm is developed from stereochemical modeling of crystallized complexes of antibodies with different protein antigens and published data about the contributions of critical amino acid residues to antigen-antibody binding energy. Three-dimensional structures of different antigen-antibody complexes have revealed that up to six hypervariable loops (or complementarity determining regions) of the antibody binding site make contact with a protein antigen. Antigenic proteins have structural epitopes consisting of 15-22 residues that constitute the binding face with antibody. The surface of a structural epitope varies between 700 and 850 square Angstroms and is about the same as the surface around the bound peptide-binding groove of an HLA molecule. Most structural epitopes have a patch of about 2-5 so-called highly energetic residues (sometimes referred to as 'hot spots') that dominate the strength and specificity of binding with antibodies. The residues of such functional epitopes are about 3 to 3.5 Angstroms apart from each other and at least one of them is non-self. The remaining residues of a structural epitope contribute supplementary interactions that increase the stability of the antigen-antibody complex.

In some embodiments, an algorithm applies the concept that each HLA antigen has multiple epitopes that can elicit specific alloantibodies. An algorithm also can address the total spectrum of antibody-accessible amino acid sequence polymorphisms as critical components of potentially immunogenic epitopes. An algorithm can consider a linear sequence of three amino acids as a minimal requirement for assessing HLA compatibility at the molecular level. Partial mismatches are assessed by determining whether or not a triplet/patch in a given position of a mismatched HLA antigen is also found in the same position in any of the patient's own HLA alleles (e.g., HLA-A, HLA-B, HLA-C, HLA-DR, HLA-DP, HLA-DQ molecules, or subset thereof, or individual allele thereof). A shared triplet/patch in the same position on a mismatched HLA antigen often cannot elicit a specific antibody response in the patient.

The selection or assignment of triplets for matching purposes does not imply that the structural basis of an epitope always involves exactly three amino acids. Many eplets or epitopes have only one or two polymorphic residues, and some epitopes can be defined by four or five polymorphic residues in adjacent or distant positions.

In some embodiments, an algorithm can identify mismatched HLA antigens that are fully compatible at the triplet/patch level. Many antigens cross react with the HLA antigens of the patient. In certain embodiments, a program can identify other cross-reacting antigens that are incompatible at the triplet/patch level and can be used for partial mismatching.

The assignment of triplets/patches to HLA antigens may lack precision if the HLA typing information is based solely on serologic methods. Other methods may reinforce HLA-typing information and be used with serologic methods. For example, DNA-based typing can permit the definition of HLA subtypes and, therefore, more accurate assignments of polymorphic triplets or patches. Many molecular subtypes of serologically defined HLA antigens have different triplets/patches in antibody-accessible positions. In such cases some serologically matched HLA antigens may have incompatible triplets/patches recognized by the patient's antibodies. In certain embodiments, stimulator information and/or responder information can include serologic determinations of HLA antigen information, nucleic acid determinations of antigen information, or combinations of the forgoing.

An algorithm can be of any suitable type, including, without limitation, search algorithms, sorting algorithms, merge algorithms, numerical algorithms, graph algorithms, string algorithms, modeling algorithms, computational genometric algorithms, combinatorial algorithms, machine learning, cryptography, data compression algorithms and parsing techniques and the like. An algorithm can comprise one or more algorithms working in combination. An algorithm can be of any suitable complexity class and/or parameterized complexity. An algorithm can be used for calculation or data processing, or used in a deterministic or probabilistic/predictive approach to a method in some embodiments.

Data Processing

The term "outcome" as used herein refers to the presence or absence of a partial mismatch (e.g., one or more mismatches) between (i) patient antigen information and/or stimulator information, and/or (ii) donor antigen information and/or responder information. Presence or absence of an outcome can be expressed in any suitable form, including, without limitation, ratio, deviation in ratio, frequency, distribution, probability (e.g., odds ratio, p-value), likelihood, percentage, value over a threshold, or risk factor, associated with the presence of a outcome for a subject or sample. Presence or absence of an outcome may be identified based on one or more calculated variables, including, but not limited to, ratio, distribution, frequency, sensitivity, specificity, standard deviation, coefficient of variation (CV), a threshold, confidence level, score, probability and/or a combination thereof.

In certain embodiments, one or more of ratio, sensitivity, specificity and/or confidence level are expressed as a percentage. In some embodiments, the percentage, independently for each variable, is greater than about 90% (e.g., about 90, 91, 92, 93, 94, 95, 96, 97, 98 or 99%, or greater than 99% (e.g., about 99.5%, or greater, about 99.9% or greater, about 99.95% or greater, about 99.99% or greater). Coefficient of variation (CV) in some embodiments is expressed as a percentage, and sometimes the percentage is about 10% or less (e.g., about 10, 9, 8, 7, 6, 5, 4, 3, 2 or 1%, or less than 1% (e.g., about 0.5% or less, about 0.1% or less, about 0.05% or less, about 0.01% or less)). A probability (e.g., that a particular outcome determined by an algorithm is not due to chance) in certain embodiments is expressed as a p-value, and sometimes the p-value is about 0.05 or less (e.g., about 0.05, 0.04, 0.03, 0.02 or 0.01, or less than 0.01 (e.g., about 0.001 or less, about 0.0001 or less, about 0.00001 or less, about 0.000001 or less)).

For example, scoring or a score may refer to calculating the probability that a particular outcome is actually present or absent in a stimulator/responder unit or pair. The value of a score may be used to determine for example the variation, difference, or ratio of amplified nucleic detectable product that may correspond to the actual outcome. For example, calculating a positive score from detectable eplets can lead to an identification of an outcome, which is particularly relevant to analysis of single patient or donor.

In certain embodiments, an algorithm can assign a confidence value to the true positives, true negatives, false positives and false negatives calculated. The assignment of a likelihood of the occurrence of an outcome can also be based on a certain probability model.

In certain embodiments, simulated (or simulation) data can aid data processing, for example, by training an algorithm or testing an algorithm. Simulated data may for instance involve hypothetical various sampling of different groupings of eplets intralocus or interlocus and the like. Simulated data may be based on what might be expected from a real population or may be skewed to test an algorithm and/or to assign a correct classification based on a simulated data set. Simulated data also is referred to herein as "virtual" data. Mismatch correlations within a stimulator/responder unit or pair can be simulated as a table or array of numbers (for example, as a list of reactive eplets found intralocus and interlocus between stimulator and responders), as a graph, as labeled intensity on a protein model, or as a representation of any technique that measures HLA partial mismatch distribution. Simulations can be performed in most instances by a computer program. One possible step in using a simulated data set is to evaluate the confidence of the identified results, i.e. how well the selected positives/negatives match the sample and whether there are additional variations. A common approach is to calculate the probability value (p-value) which estimates the probability of a random sample having better score than the selected one. As p-value calculations can be prohibitive in certain circumstances, an empirical model may be assessed, in which it is assumed that at least one sample matches a reference sample (with or without resolved variations). Alternatively, other distributions such as Poisson distribution can be used to describe the probability distribution.

Simulated data often is generated in an in silico process. As used herein, the term "in silico" refers to research and experiments performed using a computer. In silico methods include, but are not limited to, molecular modeling studies, karyotyping, genetic calculations, biomolecular docking experiments, and virtual representations of molecular structures and/or processes, such as molecular interactions.

As used herein, a "data processing routine" refers to a process that can be embodied in software that determines the biological significance of acquired data (i.e., the ultimate results of an assay). For example, a data processing routine can determine the amount of each nucleotide sequence species based upon the data collected. A data processing routine also may control an instrument and/or a data collection routine based upon results determined A data processing routine and a data collection routine often are integrated and provide feedback to operate data acquisition by the instrument, and hence provide assay-based judging methods provided herein.

As used herein, software refers to computer readable program instructions that, when executed by a computer, perform computer operations. Typically, software is provided on a program product containing program instructions recorded on a computer readable medium, including, but not limited to, magnetic media including floppy disks, hard disks, and magnetic tape; and optical media including CD-ROM discs, DVD discs, magneto-optical discs, and other such media on which the program instructions can be recorded.

Different methods of predicting abnormality or normality can produce different types of results. For any given prediction, there are four possible types of outcomes: true positive, true negative, false positive, or false negative. The term "true positive" as used herein refers to a subject correctly diagnosed as having an outcome. The term "false positive" as used herein refers to a subject wrongly identified as having an outcome. The term "true negative" as used herein refers to a subject correctly identified as not having an outcome. The term "false negative" as used herein refers to a subject wrongly identified as not having an outcome. Two measures of performance for any given method can be calculated based on the ratios of these occurrences: (i) a sensitivity value, the fraction of predicted positives that are correctly identified as being positives (e.g., the fraction of matched sets correctly identified by level comparison detection/determination as indicative of an outcome, relative to all matched sets identified as such, correctly or incorrectly), thereby reflecting the accuracy of the results in detecting the outcome; and (ii) a specificity value, the fraction of predicted negatives correctly identified as being negative (the fraction of matched sets correctly identified by level comparison detection/determination as indicative of mismatching normality, relative to all matched sets identified as such, correctly or incorrectly), thereby reflecting accuracy of the results in detecting the outcome.

The term "sensitivity" as used herein refers to the number of true positives divided by the number of true positives plus the number of false negatives, where sensitivity (sens) may be within the range of $0 \leq sens \leq 1$. Ideally, method embodiments herein have the number of false negatives equaling zero or close to equaling zero, so that no subject is wrongly identified as not having at least one outcome when they indeed have at least one outcome. Conversely, an assessment often is made of the ability of a prediction algorithm to classify negatives correctly, a complementary measurement to sensitivity. The term "specificity" as used herein refers to the number of true negatives divided by the number of true negatives plus the number of false positives, where sensitivity (spec) may be within the range of $0 \leq spec \leq 1$. Ideally, methods embodiments herein have the number of false positives equaling zero or close to equaling zero, so that no subject wrongly identified as having at least one outcome when they do not have the outcome being assessed. Hence, a method that has sensitivity and specificity equaling one, or 100%, sometimes is selected.

One or more prediction algorithms may be used to determine significance or give meaning to the detection data collected under variable conditions that may be weighed independently of or dependently on each other. The term "variable" as used herein refers to a factor, quantity, or function of an algorithm that has a value or set of values. For example, a variable may be the age of the donor, age of the patient, sex of the patient, sex of the donor, ethnicity of the donor, ethnicity of the patient, number of eplets assessed, intralocus eplets assessed, interlocus eplets assessed and the like. The term "independent" as used herein refers to not being influenced or not being controlled by another. The term "dependent" as used herein refers to being influenced or controlled by another. For example, a particular eplet set being assessed per each HLA types (A, B, or C) are variables that are dependent upon each other.

Any suitable type of method or prediction algorithm may be utilized to give significance to the data of the present invention within an acceptable sensitivity and/or specificity. For example, prediction algorithms such as Mann-Whitney U Test, binomial test, log odds ratio, log-rank test, Chi-squared test, z-test, t-test, ANOVA (analysis of variance), regression analysis, neural nets, fuzzy logic, Hidden Markov Models, multiple model state estimation, and the like may be used. One or more methods or prediction algorithms may be determined to give significance to the data having different independent and/or dependent variables of the present invention. And one or more methods or prediction algorithms may be determined not to give significance to the data having different independent and/or dependent variables of the present invention. One may design or change parameters of the different variables of methods described herein based on results of one or more prediction algorithms (e.g., number of sets analyzed, types of eplets in each set). For example, applying the Chi-square test to detection data may suggest that specific HLA types are correlated to a higher likelihood of having a particular brain tumor with a specific outcome, hence the variable of HLA types may be weighed differently versus being weighed the same as other variables.

In certain embodiments, several algorithms may be chosen to be tested. These algorithms then can be trained with raw data. For each new raw data sample, the trained algorithms will assign a classification to that sample (i.e. partial mismatch). Based on the classifications of the new raw data samples, the trained algorithms' performance may be assessed based on sensitivity and specificity. Finally, an algorithm with the highest sensitivity and/or specificity or combination thereof may be identified.

A sample is one or more cells from a donor or patient in some embodiments. Presence or absence of an outcome may be determined for all samples tested, and in some embodiments, presence or absence of an outcome is determined in a subset of the samples (e.g., samples from Grade III tumor patients). In certain embodiments, an outcome is determined for about 60-99%, or even greater than 99%, of samples analyzed in a set. A set of samples can include any suitable number of samples, and in some embodiments, a set has about 10-1000 samples, or even more than 1000 samples. The set may be considered with respect to samples tested in a particular period of time, and/or at a particular location. The set may be partly defined by other criteria, for example, age and/or ethnicity. The set may be comprised of a sample which is subdivided into subsamples or replicates all or some of which may be tested. The set may comprise a sample from the same subject collected at two different times. In certain embodiments, an outcome is determined about 60% or more of the time for a given sample analyzed, up to more than 99% of the time for a given sample). In certain embodiments, analyzing a higher number of characteristics (e.g., HLA antigens and/or DNA) that discriminate alleles can increase the percentage of outcomes determined for the samples (e.g., discriminated in a multiplex analysis). In some embodiments, one or more tissue or fluid samples (e.g., one or more blood samples) are provided by a subject (e.g., Grade III tumor patient). In certain embodiments, one or more RNA or DNA samples, or two or more replicate RNA or DNA samples, are isolated from a single tissue or fluid sample, and analyzed by methods described herein.

As noted above, algorithms, software, processors and/or machines, for example, can be utilized to (i) process detection data pertaining to partial mismatches, and/or (ii) identify the presence or absence of a outcome. In certain embodiments, provided are methods for identifying the presence or absence of an outcome that comprise: (a) providing a system, wherein the system comprises distinct software modules, and wherein the distinct software modules comprise a input module, a logic processing module, and a data display organization module; (b) detecting input information indicating the presence or absence of a partial mismatch; (c) receiving, by the logic processing module, the input information; (d) calling the presence or absence of an outcome by the logic processing module; and (e) organizing, by the data display organization model in response to being called by the logic processing module, a data display indicating the presence or absence of the outcome.

Provided also are methods for identifying the presence or absence of an outcome, which comprise providing input information indicating the presence or absence of a partial mismatch; providing a system, wherein the system comprises distinct software modules, and wherein the distinct software modules comprise an input detection module, a logic processing module, and a data display organization module; receiving, by the logic processing module, the input information; calling the presence or absence of an outcome by the logic processing module; and, organizing, by the data display organization model in response to being called by the logic processing module, a data display indicating the presence or absence of the outcome.

Provided also are methods for identifying the presence or absence of an outcome, which comprise providing a system, wherein the system comprises distinct software modules, and wherein the distinct software modules comprise an input detection module, a logic processing module, and a data display organization module; receiving, by the logic processing module, input information indicating the presence or absence of a partial mismatch; calling the presence or absence of an outcome by the logic processing module; and, organizing, by the data display organization model in response to being called by the logic processing module, a data display indicating the presence or absence of the outcome.

By "providing input information" is meant any manner of providing the information, including, for example, computer communication means from a local, or remote site, human data entry, or any other method of transmitting input information. The signal information may be generated in one location and provided to another location.

By "obtaining" or "receiving" input information is meant receiving the signal information by computer communication means from a local, or remote site, human data entry, or any other method of receiving signal information. The input information may be generated in the same location at which it is received, or it may be generated in a different location and transmitted to the receiving location.

By "indicating" or "representing" the amount is meant that the input information is related to, or correlates with, for example, the percent mismatch or presence or absence of partial mismatch. The information may be, for example, the calculated data associated with the presence or absence of partial mismatch as obtained, for example, after converting raw data obtained by HLA typing.

Also provided are computer program products, such as, for example, a computer program product comprising a computer usable medium having a computer readable program code embodied therein, the computer readable program code adapted to be executed to implement a method for identifying the presence or absence of an outcome, which comprises (a) providing a system, wherein the system comprises distinct software modules, and wherein the distinct software modules comprise a signal detection module, a logic processing module, and a data display organization module; (b) detecting input information indicating the presence or absence of a partial mismatch; (c) receiving, by the logic processing module, the input information; (d) calling the presence or absence of an outcome by the logic processing module; and, organizing, by the data display organization model in response to being called by the logic processing module, a data display indicating the presence or absence of the outcome.

Also provided are computer program product, such as, for example, computer program products comprising a computer usable medium having a computer readable program code embodied therein, the computer readable program code adapted to be executed to implement a method for identifying the presence or absence of an outcome, which comprises providing a system, wherein the system comprises distinct software modules, and wherein the distinct software modules comprise a signal detection module, a logic processing module, and a data display organization module; receiving signal information indicating the presence or absence of a partial mismatch; calling the presence or absence of an outcome by the logic processing module; and, organizing, by the data display organization model in response to being called by the logic processing module, a data display indicating the presence or absence of the outcome.

Input information may be, for example, total number of mismatches, specific types of mismatches, or both must be factored into development, i.e., training and validation of the program along with in vitro functional and phenotypic data obtained from an algorithm, or statistical likelihood given other parameters. The mismatch data may be raw data, such as, for example, a set of numbers, or, for example, a range of mismatch dependent upon HLA type. The input information may be converted or transformed to any form of data that may be provided to, or received by, a computer system. The input information may also, for example, be converted, or transformed to identification data or information representing an outcome. An outcome may be, for example, a specific HLA type, a HLA type ratio, or a particular percentage mismatch, for example.

Also provided is a machine for identifying the presence or absence of an outcome wherein the machine comprises a computer system having distinct software modules, and wherein the distinct software modules comprise a signal detection module, a logic processing module, and a data display organization module, wherein the software modules are adapted to be executed to implement a method for identifying the presence or absence of an outcome, which comprises (a) detecting input information indicating the presence or absence of a partial mismatch; (b) receiving, by the logic processing module, the signal information; (c) calling the presence or absence of an outcome by the logic processing module, wherein a percent partial mismatch different than a normal matching or mismatching ratio is indicative of a good stimulator/responder unit; and (d) organizing, by the data display organization model in response to being called by the logic processing module, a data display indicating the presence or absence of the outcome. The machine may further comprise a memory module for storing signal information or data indicating the presence or absence of a partial mismatch. Also provided are methods for identifying the presence or absence of an outcome, wherein the methods comprise the use of a machine for identifying the presence or absence of an outcome.

Also provided are methods for identifying the presence or absence of an outcome that comprises: (a) detecting input information, wherein the input information indicates presence or absence of a partial mismatch; (b) transforming the input information into identification data, wherein the identification data represents the presence or absence of the outcome, whereby the presence or absence of the outcome is identified based on the signal information; and (c) displaying the identification data.

Also provided are methods for identifying the presence or absence of an outcome that comprises: (a) providing signal information indicating the presence or absence of a partial mismatch; (b) transforming the signal information representing into identification data, wherein the identification data represents the presence or absence of the outcome, whereby the presence or absence of the outcome is identified based on the signal information; and (c) displaying the identification data.

Also provided are methods for identifying the presence or absence of an outcome that comprises: (a) receiving signal information indicating the presence or absence of a partial mismatch; (b) transforming the signal information into identification data, wherein the identification data represents the presence or absence of the outcome, whereby the presence or absence of the outcome is identified based on the signal information; and (c) displaying the identification data.

For purposes of these, and similar embodiments, the term "input information" indicates information readable by any electronic media, including, for example, computers that represent data derived using the present methods. For example, "input information" can represent the amount of a partial mismatch or percentage. Input information, such as in these examples, that represents physical substances may be transformed into identification data, such as a visual display, that represents other physical substances, such as, for example, a HLA disorder, or a HLA type. Identification data may be displayed in any appropriate manner, including, but not limited to, in a computer visual display, by encoding the identification data into computer readable media that may, for example, be transferred to another electronic device (e.g., electronic record), or by creating a hard copy of the display, such as a print out or physical record of information. The information may also be displayed by auditory signal or any other means of information communication. In some embodiments, the input information may be detection data obtained using methods to detect a partial mismatch.

Once the input information is detected, it may be forwarded to the logic-processing module. The logic-processing module may "call" or "identify" the presence or absence of an outcome.

Provided also are methods for transmitting genetic information to a subject, which comprise identifying the presence or absence of an outcome wherein the presence or absence of the outcome has been determined from determining the presence or absence of a partial mismatch from a sample from the subject; and transmitting the presence or absence of the outcome to the subject. A method may include transmitting HLA type information of a brain tumor subject and donor, and the outcome may be presence or absence of a partial mismatch between the two, in certain embodiments.

The term "identifying the presence or absence of an outcome" or "an increased risk of an outcome," as used herein refers to any method for obtaining such information, including, without limitation, obtaining the information from a laboratory file. A laboratory file can be generated by a laboratory that carried out an assay to determine the presence or absence of an outcome. The laboratory may be in the same location or different location (e.g., in another country) as the personnel identifying the presence or absence of the outcome from the laboratory file. For example, the laboratory file can be generated in one location and transmitted to another location in which the information therein will be transmitted to the subject. The laboratory file may be in tangible form or electronic form (e.g., computer readable form), in certain embodiments.

The term "transmitting the presence or absence of the outcome to the subject" or any other information transmitted as used herein refers to communicating the information to the subject, or family member, guardian or designee thereof, in a suitable medium, including, without limitation, in verbal, document, or file form.

Also provided are methods for providing to a subject a medical prescription based on genetic information, which comprise identifying the presence or absence of an outcome, wherein the presence or absence of the outcome has been determined from the presence or absence of a partial mismatch from a stimulator/responder unit; and providing a medical prescription based on the presence or absence of the outcome to the patient. The medical prescription is administration of reactive cytotoxic T cells prepared from responder/stimulator pair identified by a partial mismatch, in some embodiments.

Also provided are files, such as, for example, a file comprising the presence or absence of outcome for a subject, wherein the presence or absence of the outcome has been determined from the presence or absence of a partial mismatch from a stimulator/responder unit. The file may be, for example, but not limited to, a computer readable file, a paper file, or a medical record file.

Computer program products include, for example, any electronic storage medium that may be used to provide instructions to a computer, such as, for example, a removable storage device, CD-ROMS, a hard disk installed in hard disk drive, signals, magnetic tape, DVDs, optical disks, flash drives, RAM or floppy disk, and the like.

Systems discussed herein may further comprise general components of computer systems, such as, for example, network servers, laptop systems, desktop systems, handheld systems, personal digital assistants, computing kiosks, and the like. The computer system may comprise one or more input means such as a keyboard, touch screen, mouse, voice recognition or other means to allow the user to enter data into the system. The system may further comprise one or more output means such as a CRT or LCD display screen, speaker, FAX machine, impact printer, inkjet printer, black and white or color laser printer or other means of providing visual, auditory or hardcopy output of information.

Input and output devices may be connected to a central processing unit which may comprise among other components, a microprocessor for executing program instructions and memory for storing program code and data. In some embodiments the methods may be implemented as a single user system located in a single geographical site. In other embodiments methods may be implemented as a multi-user system. In the case of a multi-user implementation, multiple central processing units may be connected by means of a network. The network may be local, encompassing a single department in one portion of a building, an entire building, span multiple buildings, span a region, span an entire country or be worldwide. The network may be private, being owned and controlled by the provider or it may be implemented as an Internet based service where the user accesses a web page to enter and retrieve information.

The various software modules associated with the implementation of the present products and methods can be suitably loaded into the a computer system as desired, or the software code can be stored on a computer-readable medium such as a floppy disk, magnetic tape, or an optical disk, or the like. In an online implementation, a server and web site maintained by an organization can be configured to provide software downloads to remote users. As used herein, "module," including grammatical variations thereof, means, a self-contained functional unit which is used with a larger system. For example, a software module is a part of a program that performs a particular task. Thus, provided herein is a machine comprising one or more software modules described herein, where the machine can be, but is not limited to, a computer (e.g., server) having a storage device such as floppy disk, magnetic tape, optical disk, random access memory and/or hard disk drive, for example.

The present methods may be implemented using hardware, software or a combination thereof and may be implemented in a computer system or other processing system. An example computer system may include one or more processors. A processor can be connected to a communication bus. The computer system may include a main memory, sometimes random access memory (RAM), and can also include a secondary memory. The secondary memory can include, for example, a hard disk drive and/or a removable storage drive, representing a floppy disk drive, a magnetic tape drive, an optical disk drive, memory card etc. The removable storage drive reads from and/or writes to a removable storage unit in a well-known manner. A removable storage unit includes, but is not limited to, a floppy disk, magnetic tape, optical disk, etc. which is read by and written to by, for example, a removable storage drive. As will be appreciated, the removable storage unit includes a computer usable storage medium having stored therein computer software and/or data.

In certain embodiments, secondary memory may include other similar means for allowing computer programs or other instructions to be loaded into a computer system. Such means can include, for example, a removable storage unit and an interface device. Examples of such can include a program cartridge and cartridge interface (such as that found in video game devices), a removable memory chip (such as an EPROM, or PROM) and associated socket, and other removable storage units and interfaces which allow software and data to be transferred from the removable storage unit to a computer system.

A computer system may also include a communications interface. A communications interface allows software and data to be transferred between the computer system and external devices. Examples of communications interface can include a modem, a network interface (such as an Ethernet card), a communications port, a PCMCIA slot and card, etc. Software and data transferred via communications interface are in the form of signals, which can be electronic, electromagnetic, optical or other signals capable of being received by communications interface. These signals are provided to communications interface via a channel. This channel carries signals and can be implemented using wire or cable, fiber optics, a phone line, a cellular phone link, an RF link and other communications channels. Thus, in one example, a communications interface may be used to receive signal information to be detected by the signal detection module.

In a related aspect, the signal information may be input by a variety of means, including but not limited to, manual input devices or direct data entry devices (DDEs). For example, manual devices may include, keyboards, concept keyboards, touch sensitive screens, light pens, mouse, tracker balls, joysticks, graphic tablets, scanners, digital cameras, video digitizers and voice recognition devices. DDEs may include, for example, bar code readers, magnetic strip codes, smart cards, magnetic ink character recognition, optical character recognition, optical mark recognition, and turnaround documents. In one embodiment, an output from a gene or chip reader my serve as an input signal.

FIG. 2 shows a flowchart 200 generally outlining an embodiment of a method described herein. In FIG. 2, collection of stimulator and/or responder information (210) contributes to identification (220) of the presence or absence of a partial mismatch for stimulator and responder(s) pairs. Identification (220) can be performed by an algorithm, statistics, modeling, a simulation in vitro or in silico or any combination thereof. Identification (220) of the presence of a partial mismatch leads to combining cells of a selected stimulator and responder(s). After combining stimulator and responder cells (230), in vitro immunogenic data optionally may be collected and used to alter the method for performing identification (220) (e.g., the method comprises an algorithm) and/or to improve identification of partial mismatches, shown by arrow 270. After combining stimulator and responder cells (230), cytotoxic T lymphocytes are harvested (240) and administered to the patient/stimulator (250). Optionally, the patient/stimulator's response to the treatment is monitored (260) and in vivo data optionally is collected (e.g., in vivo immunogenic data, anti-tumor response). Optionally, in vivo immunogenic data is used to alter the method for performing identification (220) (e.g., the method comprises an algorithm) and/or to improve identification of partial mismatches, shown by arrow 280.

Figure 3:
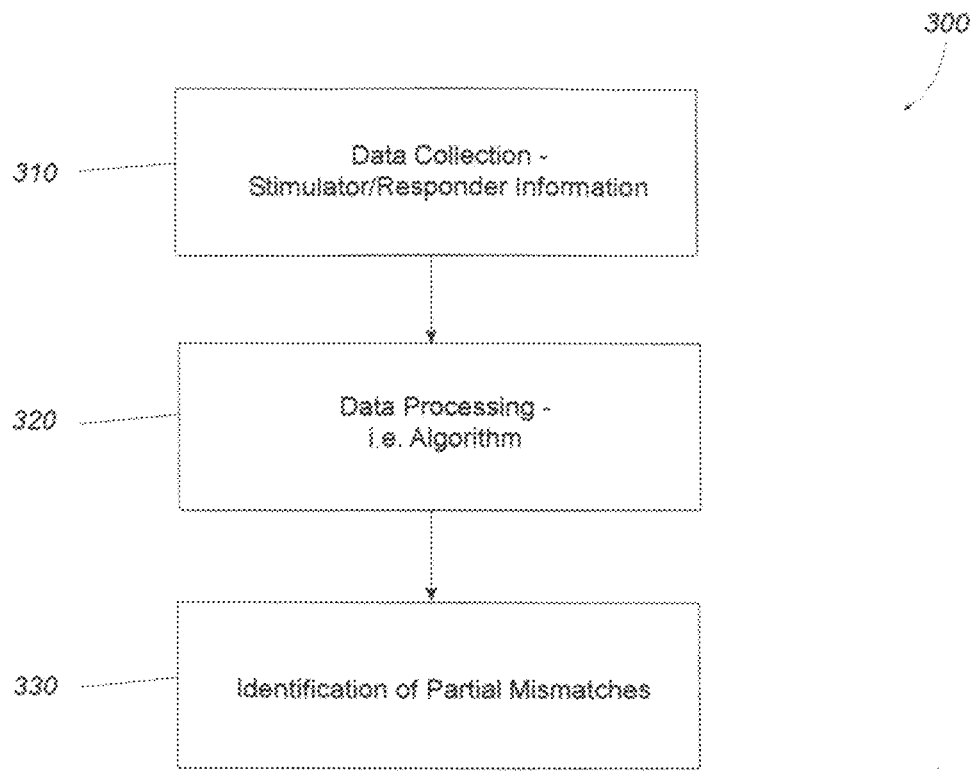
FIG. 3 shows a flowchart of an exemplary application of an algorithm to the method of FIG. 2.

FIG. 3 shows a flowchart 300 generally outlining a method described herein, where stimulator and responder information or data collected 310 is used by any known data processing method 320, such as for example an algorithm, statistics, modeling, a simulation in vitro or in silico or any combination thereof. Data 320 is used to identify a partial mismatch 330 of stimulator and/or responder information.

Figure 4:
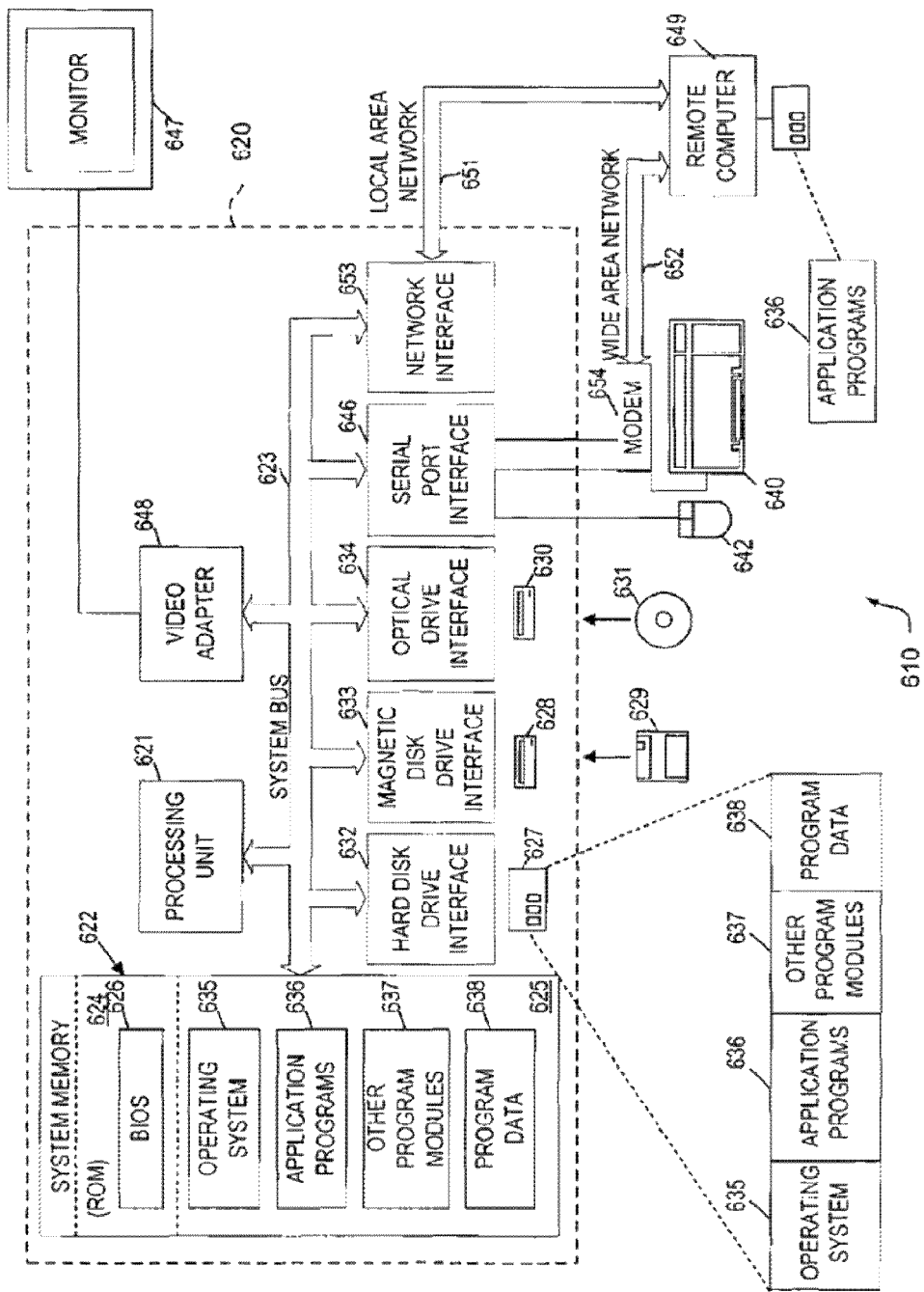
FIG. 4 shows an exemplary computing environment where data processing and the algorithm of FIG. 3 may be utilized.

A non-limiting example of how a process in FIG. 3 can occur is with DNA, RNA, or protein structure information on HLA molecules from stimulator and responders. After HLA typing each stimulator and responder, mismatch information between each HLA molecule can be assessed. Identification of mismatched amino acids can be determined from HLA antigen information, such as, molecularly and/or serologically determined HLA-A, —B, —C, -DR, -DP, -DQ molecules (e.g., individual alleles or antigens, groups of alleles or antigens of all alleles or antigens), for example. Further HLA analysis, such as location, surface expression, and/or amino acid composition, of each mismatched aa also can be generated. Identification of highly immunogenic mismatches can increase activation of cytotoxic T cells. Once the 3D structural HLA protein information is processed into 2D amino acid composition, then any data processing 320 can occur to produce identification of partial mismatches 330. For example, amino acid composition of HLA molecules for stimulator and responders can be processed through a string matching algorithm where the amino acid pattern for a particular HLA molecule (e.g., per mismatch, group of mismatches, HLA class, HLA molecule type, or the like) is used and searched for other identical or similar occurrences or locations within the same molecule, different molecule and/or different sample. The algorithm can process data in any known way, for example by hand or by using a computing environment as depicted in FIG. 4. Any processing of data 320, such as using an algorithm, can be utilized in a computing environment, such as FIG. 4, by use of a programming language such as C, C++, Java, Perl, Python, Fortran and the like. The algorithm can be modified to include margin of errors, statistic analysis, in vivo data 280 and in vitro data 270 as well as comparison to other stimulator/responder information (for example in using a neural net or clustering algorithm). The algorithm can then assign matching, mismatching and/or partial mismatching of aa per HLA molecule for stimulator and responder(s) pairs.

FIG. 4 illustrates a non-limiting example of a computing environment 610 in which various systems, methods, algorithms, and data structures described herein may be implemented. The computing environment 610 is only one example of a suitable computing environment and is not intended to suggest any limitation as to the scope of use or functionality of the systems, methods, and data structures described herein. Neither should computing environment 610 be interpreted as having any dependency or requirement relating to any one or combination of components illustrated in computing environment 610. A subset of systems, methods, and data structures shown in FIG. 4 can be utilized in certain embodiments.

Systems, methods, and data structures described herein are operational with numerous other general purpose or special purpose computing system environments or configurations. Examples of known computing systems, environments, and/or configurations that may be suitable include, but are not limited to, personal computers, server computers, thin clients, thick clients, hand-held or laptop devices, multiprocessor systems, microprocessor-based systems, set top boxes, programmable consumer electronics, network PCs, minicomputers, mainframe computers, distributed computing environments that include any of the above systems or devices, and the like.

The operating environment 610 of FIG. 4 includes a general purpose computing device in the form of a computer 620, including a processing unit 621, a system memory 622, and a system bus 623 that operatively couples various system components include the system memory to the processing unit 621. There may be only one or there may be more than one processing unit 621, such that the processor of computer 620 comprises a single central-processing unit (CPU), or a plurality of processing units, commonly referred to as a parallel processing environment. The computer 620 may be a conventional computer, a distributed computer, or any other type of computer.

The system bus 623 may be any of several types of bus structures including a memory bus or memory controller, a peripheral bus, and a local bus using any of a variety of bus architectures. The system memory may also be referred to as simply the memory, and includes read only memory (ROM) 624 and random access memory (RAM) 625. A basic input/output system (BIOS) 626, containing the basic routines that help to transfer information between elements within the computer 620, such as during start-up, is stored in ROM 624. The computer 620 may further include a hard disk drive interface 627 for reading from and writing to a hard disk, not shown, a magnetic disk drive 628 for reading from or writing to a removable magnetic disk 629, and an optical disk drive 630 for reading from or writing to a removable optical disk 631 such as a CD ROM or other optical media.

The hard disk drive 627, magnetic disk drive 628, and optical disk drive 630 are connected to the system bus 623 by a hard disk drive interface 632, a magnetic disk drive interface 633, and an optical disk drive interface 634, respectively. The drives and their associated computer-readable media provide nonvolatile storage of computer-readable instructions, data structures, program modules and other data for the computer 620. Any type of computer-readable media that can store data that is accessible by a computer, such as magnetic cassettes, flash memory cards, digital video disks, Bernoulli cartridges, random access memories (RAMs), read only memories (ROMs), and the like, may be used in the operating environment.

A number of program modules may be stored on the hard disk, magnetic disk 629, optical disk 631, ROM 624, or RAM 625, including an operating system 635, one or more application programs 636, other program modules 637, and program data 638. A user may enter commands and information into the personal computer 620 through input devices such as a keyboard 40 and pointing device 642. Other input devices (not shown) may include a microphone, joystick, game pad, satellite dish, scanner, or the like. These and other input devices are often connected to the processing unit 621 through a serial port interface 646 that is coupled to the system bus, but may be connected by other interfaces, such as a parallel port, game port, or a universal serial bus (USB). A monitor 647 or other type of display device is also connected to the system bus 623 via an interface, such as a video adapter 648. In addition to the monitor, computers typically include other peripheral output devices (not shown), such as speakers and printers.

The computer 620 may operate in a networked environment using logical connections to one or more remote computers, such as remote computer 649. These logical connections may be achieved by a communication device coupled to or a part of the computer 620, or in other manners. The remote computer 649 may be another computer, a server, a router, a network PC, a client, a peer device or other common network node, and typically includes many or all of the elements described above relative to the computer 620, although only a memory storage device 650 has been illustrated in FIG. 4. The logical connections depicted in FIG. 4 include a local-area network (LAN) 651 and a wide-area network (WAN) 652. Such networking environments are commonplace in office networks, enterprise-wide computer networks, intranets and the Internet, which all are types of networks.

When used in a LAN-networking environment, the computer 620 is connected to the local network 651 through a network interface or adapter 653, which is one type of communications device. When used in a WAN-networking environment, the computer 620 often includes a modem 654, a type of communications device, or any other type of communications device for establishing communications over the wide area network 652. The modem 654, which may be internal or external, is connected to the system bus 623 via the serial port interface 646. In a networked environment, program modules depicted relative to the personal computer 620, or portions thereof, may be stored in the remote memory storage device. It is appreciated that the network connections shown are non-limiting examples and other communications devices for establishing a communications link between computers may be used.

Stimulator Cell and Donor Cell Preparation

After identifying the presence of a partial mismatch for a donor/patient pair, cytotoxic T cells may be prepared by mixing cells of the donor with inactivated cells of the patient for donor/patient pairs exhibiting a partial mismatch. Stimulator cells and responder cells are prepared before such an activation reaction is conducted.

Stimulator cells, which are derived from a patient, and responder cells, which are derived from a donor, independently can be from any suitable source. A source of cells includes, without limitation, blood, blood fraction (e.g., plasma, serum, buffy coat, red blood cell layer), bone marrow, biological fluid (e.g., urine, blood, saliva, amniotic fluid, exudate from a region of infection or inflammation, mouth wash, cerebral spinal fluid, synovial fluid), or organ, tissue, cell, cell pellet, cell extract or biopsy (e.g., brain, neck, spine, throat, heart, lung, breast, kidney, liver, intestine, colon, pancreas, bladder, cervix, testes, skin and the like). The source can be directly from the patient or donor, sometimes is frozen, and at times is provided as a cell suspension. A source of cells includes, without limitation, a human or an animal (e.g., canine, feline, ungulate (e.g., equine, bovine, caprine, ovine, porcine, buffalo, camel and the like), rodent (e.g., murine, mouse, rat), avian, amphibian, reptile, fish).

Cells from a patient sometimes are from patient blood, and in certain embodiments are immune cells, such as simulator white blood cells or lymphocytes or dendritic cells from the blood. Cells from a donor sometimes are from donor blood, and in certain embodiments are white blood cells or lymphocytes from the blood. Stimulator donor blood and or buffy coat sometimes is from a blood bank. Blood sometimes is peripheral blood, sometimes is a blood fraction (e.g., buffy coat), sometimes is zero to seven days old, and at times is frozen blood or frozen blood fraction (e.g., blood cells are vitally cryopreserved).

A patient from whom stimulator cells are derived often is afflicted with a medical condition. A medical condition can be a cell proliferation condition, an autoimmune condition and/or inflammation condition, in some embodiments (non-limiting examples are provided herein).

Donor cells or patient cells, or stimulator cells or responder cells, sometimes include a substantial amount of a particular type of cell. The term "substantial amount" as used in the foregoing sentence refers to 25% or more of cells in a container (e.g., flask, tube, plate; about 30%, 35%, 40%, 45%, 50%, 55%, 60%, 65%, 70%, 75%, 80%, 85%, 90% or 95% or more). Particular cell types include, without limitation, white blood cell, granulocyte, agranulocyte, monocyte, lymphocyte, B cell, T cell, CD4+ T cell, CD8+ T cell, natural killer cell, stem cell (e.g., CD34+ cell), lymphoblast, antigen presenting cell, dendritic cell, macrophage, neutrophil, eosinophil, basophil. An antigen presenting cell sometimes is a professional antigen presenting cell, which can include, without limitation, a dendritic cell, macrophage, B cell and activated epithelial cell.

Donor cells and/or patient cells sometimes are subjected to a treatment process before they are combined for activation of T cells into cytotoxic T cells. A treatment process can increase the relative amount of a particular cell type in a composition, or can generate a new cell type in a population. For example, a treatment process can be utilized to differentiate patient cells into dendritic cells or activate patient cells into lymphoblasts, in certain embodiments. Certain treatments of donor cells into stimulator cells can improve the immunogenic action of responder cells when the stimulator cells are combined with the responder cells.

In some embodiments, however, donor cells and/or patient cells are not subjected to a treatment process prior to combining them with one another for production of cytotoxic T cells (e.g., white blood cells from the donor are mixed with stimulator cells). In the latter embodiments, the donor cells and patient cells are responder cells and stimulator cells, respectively.

In certain treatment methods, white blood cells from a patient or donor are provided and certain cell types are separated. White blood cells sometimes are collected by isolating peripheral blood mononuclear cells (PBMC) by a suitable method (e.g., ficoll gradient centrifugation). In some embodiments, monocytes are separated (e.g., for differentiation into dendritic cells), and sometimes are separated from other non-adherent cells because they adhere to a solid support in a particular medium (e.g., AIM-V medium) in certain embodiments. Lymphocytes are separated (e.g., for activation of lymphoblasts) in some embodiments, and sometimes are separated by collecting cells that do not adhere to a solid support in a particular medium (e.g., commercially available AIM-V medium).

In some embodiments, a treatment method prepares dendritic cells (DCs). Dendritic cells can be prepared by any suitable method known in the art, and non-limiting examples of DC differentiation methods are described herein (e.g., Examples section). In some embodiments, DCs are separated from other cells in a population and then expanded. In such methods, DCs may be contacted with one or more antibodies that bind to DC cell markers, and the DCs are separated by flow cytometry, in certain embodiments.

In some embodiments, DCs are differentiated from precursor cells. In some DC differentiation methods, monocytes from PBMC are differentiated into immature DCs and then to mature DCs. Immature DCs sometimes are differentiated from monocytes by contacting the latter with one or more suitable stimulants. Any suitable medium can be utilized for differentiation of dendritic cells (e.g., AIM-V medium). In certain embodiments, DCs are differentiated from stem cells. DCs derived from a patient and selected for combination with donor cells are of any suitable maturation or activation state and can express Toll-like receptors of various types. Cultures having mature DCs are selected for combination with donor cells in certain embodiments.

Examples of stimulants include, without limitation, cytokines, which include, for example, interleukins (e.g., IL-1, IL-2, IL-3, IL-4, IL-5, IL-6, IL-7, IL-8, IL-9, IL-10, IL-11, IL-12, IL-13, IL-14, IL-15, IL-16, IL-17, IL-18 and the like), interferons (e.g., IFN-α, IFN-β, IFN-γ and the like), cytokins (e.g., TNF-α, TNF-β and the like), lymphokines, monokines and chemokines; growth factors (e.g., transforming growth factors (e.g., TGF-alpha, TGF-beta and the like)); colony-stimulating factors (e.g., granulocyte macrophage colony-simulating factor (GM-CSF), granulocyte colony-simulating factor (G-CSF) etc.); and the like. In some embodiments, monocytes are contacted with one or more interleukins (e.g., IL-4), and/or one or more colony-stimulating factors (e.g., GM-CSF). In certain embodiments, monocytes and/or immature DCs are contacted with one or more interleukins (e.g., IL-6, IL-1beta) and/or one or more tumor necrosis factors (e.g., TNF alpha). A suitable amount of stimulant is selected as known in the art, and the amount of a stimulant can range from about 5 units to about 5000 units. In some embodiments, about 0.2 ng/ml to about 1000 ng/ml of a stimulant is utilized. A stimulant can be native polypeptide purified from a cell and often is recombinant polypeptide. A stimulant often is a human polypeptide, and often is produced by recombinant methods (e.g., recombinant human IL-2 (rhIL-2)).

Other stimulants include pattern recognition receptors (PRRs), which are proteins expressed by cells of the innate immune system to identify pathogen-associated molecular patterns (PAMPs) that are associated with microbial pathogens or cellular stress (such as heat shock proteins).

Examples of PRRs include, without limitation, molecules such as toll-like receptors (TLRs) comprising members TLR-3, TLR-7, TLR-8, and TLR-9 and C-type lectin receptors (CLRs). These in turn include members DC-SIGN, dectin-1, langerin and the mannose receptor, which recognize glycan epitopes present on a range of pathogens, including viruses, bacteria, and fungi.

Examples of PAMPs include, without limitation, molecules such as TLR-agonists, imiquimod, monophosphoryl lipid A (MPL), fibroblast-stimulating lipopeptide-1 (FSL-1), Pam3CSK4, lipolysaccharide (also known as LPS or endotoxin), peptidoglycan (cell walls), lipoproteins (bacterial capsules), hypomethylated DNA (such as CpG found in bacteria and other parasites), double-stranded DNA as found in viruses, and flagellin (bacterial flagella).

Activation through different PRRs can lead to varying patterns of cytokine release by DCs. In particular, signaling through PRRs is known to influence T cell responses, and can have variable consequences, such as enhancing effector T cell activity or alternatively inducing autoimmunity.

Direct peptide delivery to DCs may be performed using particulate delivery systems, such as nanoparticles (NPs). In addition to having a depot effect on the peptide antigens, certain inherent properties of the NPs themselves engender immunogenicity of the peptides, and allow uptake of an immunogenic package of peptides and other molecules. Because of their size and particulate nature, NPs are readily phagocytosed by scavenger cells such as macrophages or DCs, resulting in a targeted delivery of peptides to these cells.

Furthermore, many of these phagocytic cells—in particular, DCs—are excellent antigen presenting cells (APC). Thus, NPs can deliver peptide to the cells (and indeed, the subcellular compartments) where they will be most immunogenic. This approach is exemplified with a number of different NP formulations, including liposomes and immunostimulatory complexes (ISCs), as well as virosomes and exosomes. For example, see Kersten, G. F. and Crommelin, D. J. (2003). "Liposomes and ISCOMs." Vaccine 21 9-10: 915-20; Westerfeld, N. and Zurbriggen, R. (2005). "Peptides delivered by immunostimulating reconstituted influenza virosomes." J Pept Sci 11 11: 707-12; and Taieb, J., Chaput, N. and Zitvogel, L. (2005). "Dendritic cell-derived exosomes as cell-free peptide-based vaccines." Crit. Rev Immunol 25 3: 215-23.

Polymeric NPs offer significant advantages over other types of NPs due to their excellent safety profile, and their versatility in designing customized products for specific targeting applications. They are relatively simple to manufacture, and can be lyophilized for long-term storage.

One type among the possible NPs is based on polylactic-co-glycolic acid (PLGA). This biodegradable and biocompatible polymer is approved for in vivo use by the Food and Drug Administration (FDA). Spherical in shape with an average diameter of 200-300 nm, antigen-bearing PLGA-NPs efficiently deliver peptides to DCs, resulting in presentation of those peptides by DCs for several days. These biocompatible NPs serve as effective vehicles for the delivery of peptide antigen to DCs, both in vitro and in vivo, and these peptides are efficiently displayed by cell-surface HLA, leading to the induction of antigen-specific CTL. Importantly, these PLGA NP are acid-labile, maintaining their integrity at neutral pH, but break down when subjected to a lower pH in phagocytic vesicles.

NPs of varying compositions may be formulated using an emulsion-solvent evaporation technique as previously described in Vasir, J. K. and Labhasetwar, V., "Biodegradable nanoparticles for cytosolic delivery of therapeutics." Adv. Drug Deliv. Rev. 59 8: 718-28 (2007).

A DC can be differentiated from a stem cell in some embodiments. In certain non-limiting DC differentiation methods, a hematopoietic stem cell (e.g., a human CD34+ stem cell) can be differentiated into a dendritic cell. Stem cells can be isolated by methods known in the art. For example, bone marrow aspirations from iliac crests can be performed e.g., under general anesthesia in the operating room. The bone marrow aspiration sometimes is approximately 1,000 ml in quantity and often is collected from the posterior iliac bones and crests. If the total number of cells collected is less than about $2 \times 10^8$/kg, a second aspiration is optionally performed (e.g., using the sternum and/or anterior iliac crests in addition to posterior crests). During the operation, two units of irradiated packed red cells can be administered to replace the volume of marrow taken by the aspiration. Human hematopoietic progenitor cells and stem cells can be characterized by the presence of a CD34 surface membrane antigen. This antigen often is used for purification. After the bone marrow is harvested, the mononuclear cells can be separated from other components by ficol gradient centrifugation. This centrifugation can be performed by a semi-automated method using a cell separator (e.g., a Baxter Fenwal CS3000+ or Terumo machine). The light density cells, composed mostly of mononuclear cells, are collected and the cells are incubated in plastic flasks at 37° C. for 1.5 hours. The adherent cells (e.g., monocytes, macrophages and B-Cells) often are discarded. The non-adherent cells can be collected can be incubated with a monoclonal anti-CD34 antibody (e.g., the murine antibody 9C5) at 4° C. for 30 minutes with gentle rotation. The final concentration for the anti-CD34 antibody often is 10 micrograms/ml. After two washes, paramagnetic microspheres (Dyna Beads, supplied by Baxter Immunotherapy Group, Santa Ana, Calif.) coated with sheep anti-mouse IgG (Fc) antibody can be added to the cell suspension at a ratio of 2 cells/bead. After a further incubation period of 30 minutes at 4° C., the rosetted cells with magnetic beads are collected with a magnet. Chymopapain (supplied by Baxter Immunotherapy Group, Santa Ana, Calif.) at a final concentration of 200 U/ml can be added to release the beads from the CD34+ cells. Alternatively, an affinity column isolation procedure can be used which binds to CD34, or to antibodies bound to CD34.

Stem cells can be differentiated in vitro using appropriate cytokines (e.g., GM-CSF). The concentration of GM-CSF in culture can be about 0.2 ng/ml or more, sometimes about 1 ng/ml or more, and at times between about 20 ng/ml and about 200 ng/ml (e.g., about 100 ng/ml), in certain embodiments. In some embodiments, TNF-alpha also is added to facilitate differentiation, sometimes in about the same concentration range as for GM-CSF. Optionally, a proliferation ligand (e.g., stem cell factor (SCF), Flt 3 ligand) is added in similar concentration ranges to differentiate human DCs, and in some embodiments, IL-4 is added in similar ranges to promote DC differentiation. In certain embodiments, a DC or DC precursor cell is transduced with a nucleic acid. The nucleic acid may encode an interleukin and/or a colony-stimulating factor (e.g., IL-4 and/or GM-CSF; U.S. Pat. No. 7,378,277, Hwu et al.). A transduction-facilitating agent (e.g., lipofectamine) can be introduced to facilitate nucleic acid transfer to cultured cells. Optimized concentrations of stimulants described in this paragraph can be assessed by titrating stimulant and observing effects (e.g., U.S. Pat. No. 7,378,277, supra).

In certain non-limiting DC differentiation methods, peripheral blood mononuclear cells (PBMC) from healthy donors can be can be isolated by density centrifugation of heparinized blood on Lymphoprep (Nycomed, Oslo, Norway). PBMC can be washed with PBS, resuspended in CellGenix DC medium (Freiburg, Germany) and allowed to adhere in culture plates for 2 h at 37° C. and 5% $CO_2$. Non-adherent cells can be removed by extensive washings, and adherent monocytes can be cultured for 5 days in the presence of 500 U/ml hIL-4 and 800 U/ml hGM-CSF (R&D Systems, Minneapolis, Minn.). As assessed by morphology and FACS analysis, resulting immature DCs (imDCs) often are MHC-class I, IIhi, and often express CD401o, CD801o, CD831o, and/or CD8610 Immature DCs often are CD14 neg and contain less than 3% of contaminating CD3+ T, CD19+ B, and CD16+ NK cells. DCs can be stimulated with MPL, FSL-1, $Pam_3CSK_4$ (InvivoGen, San Diego, Calif.), LPS (Sigma-Aldrich, St. Loucan be, MO), AP20187 (ARIAD Pharmaceuticals, Cambridge, Mass.) or maturation cocktail (MC), containing 10 ng/ml TNF-alpha, 10 ng/ml IL-1beta, 150 ng/ml IL-6 (R&D Systems, Minneapolis, Minn.) and 1 micrograms/ml of PGE2 (Cayman Chemicals, Ann Arbor, Mich.). Other methods for differentiating DCs from PBMC of a patient are described herein (e.g., in the Examples section).

Lymphoblasts also may be prepared as stimulator cells by activating patient lymphocytes, in certain embodiments. Any suitable method may be used to treat lymphocytes and activate lymphoblasts, and an example is provided herein (e.g., Examples section). Lymphoblasts can be activated from lymphocytes by contacting the latter with one or more suitable stimulants. In certain embodiments, patient lymphocytes are contacted with one or more suitable interleukins (e.g., IL-2). An amount of an interleukin often is selected for specific expansion of sensitized cells, as known in the art (e.g., 60 International Units of recombinant human IL-2 can be utilized). Lymphocytes also can be contacted with an agent that interacts with T cells (e.g., binds to a T cell receptor), such as an antibody for example (e.g., OKT3 murine monoclonal IgG2a antibody that binds to CD3 T cell receptor complex). Any suitable medium can be utilized for activation of lymphoblasts (e.g., AIM-V medium).

Methods are known in the art for isolating and expanding T cells. In certain non-limiting T cell isolation and expansion methods, Ficoll-Hypaque density gradient centrifugation can be used to separate PBMC from red blood cells and neutrophils according to established procedures. Cells can be washed with modified AIM-V (i.e., AIM-V (Invitrogen Corporation) with 2 mM glutamine, 10 micrograms/ml gentamicin sulfate, 50 micrograms/ml streptomycin) supplemented with 1% fetal bovine serum (FBS). Enrichment for T cells can be performed by negative or positive selection with appropriate monoclonal antibodies coupled to columns or magnetic beads according to standard techniques. An aliquot of cells can be analyzed for cell surface phenotype including CD4, CD8, CD3 and CD14. Cells can be washed and resuspended at a concentration of $5 \times 10^5$ cells per ml of AIM-V modified as above and containing 5% FBS and 100 U/ml recombinant IL-2 (rIL-2) (in supplemented AIM-V). Where cells are isolated from a HIV+ patient, 25 nM CD4-PE40 (a recombinant protein consisting of the HIV-1-binding CD4 domain linked to the translocation and ADP-ribosylation domains of *Pseudomonas aeruginosa* exotoxin A), or other similar recombinant cytotoxic molecule which selectively hybridizes to HIV, can be added to the cell cultures for the remainder of the cell expansion to selectively remove HIV infected cells from the culture. CD4-PE40 has been shown to inhibit p24 production in HIV-1-infected cell cultures and to selectively kill HIV-1-infected cells. To stimulate proliferation, OKT3 monoclonal antibody (Ortho Diagnostics) can be added at a concentration of about 10 ng/ml and the cells can be plated in 24 well plates with 0.5 ml per well. The cells can be cultured at 37° C. in a humidified incubator with 5% $CO_2$ for 48 hours.

In some embodiments, stimulator cells are subjected to a process that yields inactivated stimulator cells. Inactivated stimulator cells often are not capable of dividing, and often are not capable of certain functions (e.g., killing other cells). Inactivated stimulator cells are capable of activating T cells present in the responder cell population against patient antigens. Inactivated stimulator cells often retain cell surface structure, and generally are capable of presenting antigen to responder cells (e.g., presentation of antigen by way of MHC to T cell receptor of a responder cell). Methods for inactivating stimulator cells are known in the art, which include, without limitation, irradiating stimulator cells or contacting stimulator cells with mitomycin C.

Combining Stimulator Cells and Responder Cells

Stimulator cells, from a patient or derived from patient cells, and responder cells, from a donor or derived from donor cells, may be combined with one another to generate activated cytotoxic T cells. Such activated cytotoxic T cells generally arise from the responder cell population, and often are "alloreactive," meaning that they are active against the stimulator cells, which have been inactivated with agents such as mitomycin C or by sources of radiation, such a 60-Cobalt or 127-Cesium. Without being bound by theory, responder cells include T cells that are activated by antigens presented by stimulator cells, and the resulting activated cytotoxic T cells are capable of killing the stimulator cells, and cells of the patient. In certain embodiments, stimulator cells include (i) inactivated dendritic cells differentiated from patient cell monocytes, (ii) inactivated lymphoblasts activated from patient cell lymphocytes, (iii) inactivated patient cell white blood cells (e.g., PBMC), and/or (iv) tumor cells, which may or may not be exposed to interferon to up-regulate HLA antigens. Responder cells are lymphocytes from a donor in some embodiments. Combining stimulator cells and responder cells with the expectation of generating alloreactive cytotoxic T cells sometimes is referred to herein as an "activation reaction" or a one way lymphocyte dendritic cell reaction (LDCR).

In certain embodiments, a donor is selected based on having a partial mismatch of patient antigen information with donor antigen information and/or a partial mismatch of stimulator information with responder information, as described herein. Stimulator cells and responder cells can be combined in any suitable ratio for generating activated cytotoxic T cells. In certain embodiments, the ratio of stimulator: responder cells can be from about 1:1 to about 1:20. The stimulator cells and responder cells are combined under conditions conducive to generating activated cytotoxic T cells. Such conditions can include one or more stimulants (e.g., low dose IL-2 (60 IU/ml for DC stimulator cells). Culture conditions can include a suitable medium (e.g., AIM-V medium) with or without serum (e.g., 5% autologous serum) or heat inactivated and clarified plasma. In embodiments where serum is utilized in culture medium, cells may be weaned from serum-containing medium over time. Stimulator cells and responder cells may be combined for any suitable period of time, including, without limitation, from 2 to 25 or more days. Responder cells may be re-stimulated one or more times (e.g., 1 to 10 or more times) with additional stimulator cells, which can be combined at a stimulator:responder cell ratio described above. Re-stimulation can be for any suitable period of time, such as a period of time described above for the initial stimulation.

Alloreactive cytotoxic T cells resulting from the combination of stimulator cells and responder cells can be identified, separated and/or purified by methods described herein. Cytotoxic T cells also may be administered to a patient, with or without identification, separation or purification, to treat a condition or disorder, as addressed in more detail hereafter.

Characterization of Cells and Activities

Methods for assessing stimulator cells, responder cells and activated cytotoxic T cells are known in the art. Such methods can be carried out at a suitable time point, and some are performed before patient cells are exposed to activation or differentiation conditions, before stimulator cells and responder cells are combined and/or after the latter cells are combined. For example, certain methods assess the ability of antigen presenting cells (e.g., patient cells, DCs, lymphoblasts) to activate responder cells (e.g., donor cells, T cells), and some methods assess the activity of activated responder cells (e.g., donor cells, T cells). Examples of such methods are described herein (e.g., Examples section).

Presence, absence or amount of cell surface markers and/or production of certain cytokines can be utilized to determine whether certain cells have reached a particular maturation state (e.g., mature dendritic cell, mature and/or activated T cell). Levels of a stimulant in the cytoplasm of cells, or secreted by cells, also can be assessed. For example, activated T cells produce interferon (IFN) γ, which can be assayed as described herein (e.g., using an antibody that binds IFN-γ; Examples section). Cytokines can be measured in culture supernatants using commercially available enzyme-linked immunosorbent assay kits (e.g., human IL-6 and IL-12p70 (BD Biosciences).

A cell having a certain feature (e.g., one or more cell surface markers) can be identified, separated and/or purified from cells not having that feature. Presence, absence of amount of a surface marker facilitates identification, separation and/or purification of immunologic cells known in the art. For example, cells in a population can be contacted with an antibody that binds to a particular cell marker on a subset of the cells. Cells that display the marker and bind the antibody can be separated from cells that do not display the marker and do not bind the antibody. A flow cytometer can be utilized to separate certain cell types from others, and the separated cells can be assessed and/or further manipulated.

Cell surface markers expressed, or not expressed, on the cell surface at a particular state of differentiation or activation are known. For example, markers are known for cytotoxic activated T cells (e.g., CD8+, CD3+, CD69+); helper T cells (e.g., CD3+, CD4+, and CD8−); T/NK cells (CD3+, CD16+ or CD56+); regulatory T cells (e.g., CD4+/CD25+; production of certain cytokines (e.g., IL-10 and/or TGF-beta)); helper T cells (e.g., CD4+); human stem cells (e.g., CD34+). DCs express MHC molecules (e.g., HLA class I molecules, HLA class II molecules), co-stimulatory molecules (e.g., CD80+ (B7.1), CD86+ (B7.2), and CD40+, which are co-receptors in T-cell activation that enhance the DC's ability to activate T-cells) and chemotactic receptor (e.g., CCR7+). Other markers that can be detected on DCs include, without limitation, CD11c, CD83 and CD86. DCs may lack markers specific for granulocytes, NK cells, B cells, and T cells. In some instances, DCs express 33D1 (DC from spleen and Peyer's patch, but not skin or thymic medulla), NLDC145 (DC in skin and T-dependent regions of several lymphoid organs and CD11c (CD11c also reacts with macrophage)). Agents that bind to markers are known in the art and are commercially available (e.g., antibodies bound to a detectable label) and methods for identifying, separating and purifying cells using such agents are known (e.g., described herein). Cell surface staining can be performed using fluorochrome-conjugated monoclonal antibodies (BD Biosciences, San Diego, Calif.). Cells also can analyzed using a flow cytometer (e.g., FACSCalibur cytometer (BD Biosciences, San Jose, Calif.)).

Cells can be identified, separated and/or purified before being treated (e.g., differentiation into DCs or activation into lymphoblasts), after being treated, after exposure to a condition that generates inactivated cells, after being combined with a stimulator or responder counterpart, or after administration to a patient. For example, separated cells may be exposed to conditions that produce differentiated cells (e.g., DCs), activated cells (e.g., lymphoblasts, activated T cells) and/or inactivated cells (e.g., inactivated DCs, inactivated lymphoblasts), in some embodiments. Separated cells also may be administered to a subject for cell therapy (e.g., activated T cells may be administered), in certain embodiments. Separated cells can be substantially free from other cell types (e.g., substantially isolated). A cell having a particular marker, or a particular cell type, may represent about 60% of more of the cells in a population of cells (e.g., about 65%, 70%, 75%, 80%, 85%, 90%, 95%, or 95% or more in a population of cells).

Methods for identification, separation and isolation of cells include, without limitation, flow cytometry (e.g., fluorescent-activated cell sorting (FACS)), column chromatography, panning with magnetic beads, western blots, radiography, electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like.

Labeling agents can be used to label cell antigens, and examples of labels include, without limitation, monoclonal antibodies, polyclonal antibodies, proteins, or other polymers (e.g., affinity matrices), carbohydrates or lipids, which often are attached, or are capable of being attached, to a detectable label. Detection can proceed by any known method, such as immunoblotting, western blot analysis, tracking of radioactive or bioluminescent markers, capillary electrophoresis, or another other methods that tracks a molecule based upon size, charge and/or affinity. The particular label or detectable group used and the particular assay are not critical aspects of the invention. A detectable moiety can be any material having a detectable physical or chemical property. Such detectable labels have been well-developed in the field of gels, columns, solid substrates cell cytometry and immunoassays and, in general, any label useful in such methods can be applied to the present invention. Thus, a label is any composition detectable by spectroscopic, photochemical, biochemical, immunochemical, electrical, optical or chemical methods. Useful labels include, without limitation, magnetic beads (e.g. Dynabeads™), fluorescent dyes (e.g., fluorescein isothiocyanate, Texas red, rhodamine, and the like), radiolabels (e.g., 3H, 125I, 35S, 14C, or 32P), enzymes (e.g., LacZ, CAT, horse radish peroxidase, alkaline phosphatase and others, commonly used as detectable enzymes, either as marker gene products or in an ELISA), nucleic acid intercalators (e.g., ethidium bromide) and calorimetric labels such as colloidal gold or colored glass or plastic (e.g. polystyrene, polypropylene, latex, and the like) beads.

A label can be coupled directly or indirectly to a desired component of an assay or separation method according to methods known in the art. As indicated above, a wide variety of labels can be used, with the choice of label depending on the sensitivity required, ease of conjugation of the compound, stability requirements, available instrumentation, and disposal provisions. Non-radioactive labels often are attached by indirect attachments. A ligand molecule (e.g., biotin) sometimes is covalently bound to a polymer, in certain embodiments. The ligand then binds to an anti-ligand (e.g., streptavidin) molecule which is either inherently detectable or covalently bound to a signal system, such as a detectable enzyme, a fluorescent compound, or a chemiluminescent compound. A number of ligand/anti-ligand pairs can be used. Where a ligand has a natural anti-ligand, for example, biotin, thyroxine, and cortisol, it can be used in conjunction with a labeled, anti-ligand, in some embodiments. A haptenic or antigenic compound can be used in combination with an antibody in certain embodiments.

A label can be conjugated directly to a signal generating molecule (e.g., by conjugation with an enzyme or fluorophore) in some embodiments. An enzymes of interest sometimes is utilized as a label, and can be a hydrolase (e.g., phosphatase, esterase, glycosidase), or oxidoreductases (e.g., peroxidases), in certain embodiments. Fluorescent compounds include fluorescein and its derivatives, rhodamine and its derivatives, dansyl, umbelliferone, and the like. Chemiluminescent compounds include luciferin, and 2,3-dihydrophthalazinediones, e.g., luminol. For a review of various labeling or signal producing systems which are used, see, U.S. Pat. No. 4,391,904.

Labels can be detected by methods known in the art. Where a label is a radioactive, for example, a scintillation counter or photographic film (i.e., autoradiography) can be utilized. Where a label is a fluorescent label, it is optionally detected by exciting a fluorochrome with the appropriate wavelength of light and detecting the resulting fluorescence (e.g., by microscopy, visual inspection, via photographic film, by the use of flow cytometers or such-like electronic detectors such as charge coupled devices (CCDs) or photomultipliers and the like), in some embodiments. Enzymatic labels can be detected by providing appropriate substrates for the enzyme and detecting the resulting reaction product, in certain embodiments. Calorimetric labels often are detected simply by observing the color associated with the label, in some embodiments. In various dipstick assays, conjugated gold often appears pink, while various conjugated beads appear the color of the bead, for example.

Some assay formats do not require the use of labeled components. For instance, agglutination assays can be used to detect the presence of antibodies. In this case, cells are agglutinated by samples comprising the antibodies bound to the cells. In this format, none of the components need be labeled and the presence of the target antibody is detected by simple visual inspection.

Depending upon the assay or separation technique utilized, various components, including an antibody, or anti-antibody, sometimes are bound to a solid surface. For instance, in certain embodiments, unwanted cells are panned out of bone marrow using appropriate antibodies bound to a substrate over which cells are passed. Methods for immobilizing biomolecules to a variety of solid surfaces or microbeads are known in the art. For instance, a solid surface sometimes is a membrane (e.g., nitrocellulose), a microtiter dish (e.g., PVC, polypropylene, or polystyrene), a test tube (glass or plastic), a dipstick (e.g. glass, PVC, polypropylene, polystyrene, latex, and the like), a microcentrifuge tube, a flask, or a glass, silica, plastic, metallic or polymer bead. The desired component sometimes is covalently bound, or non-covalently attached (e.g., through nonspecific bonding) in certain embodiments. Organic and inorganic polymers, natural and synthetic, are known and sometimes employed as a solid surface material. Illustrative polymers include polyethylene, polypropylene, poly(4-methylbutene), polystyrene, polymethacrylate, poly (ethylene terephthalate), rayon, nylon, poly(vinyl butyrate), polyvinylidene difluoride (PVDF), silicones, polyformaldehyde, cellulose, cellulose acetate, nitrocellulose, and the like. Other materials sometimes include paper, glasses, ceramics, metals, metalloids, semiconductive materials, cements and the like. Substances that form gels, such as proteins (e.g., gelatins), lipopolysaccharides, silicates, agarose and polyacrylamides can be used. Polymers which form several aqueous phases, such as dextrans, polyalkylene glycols or surfactants, such as phospholipids, long chain (12-24 carbon atoms) alkyl ammonium salts also can be selected and utilized.

Certain assays can detect cell proliferation. In certain embodiments, T cells in a responder cell population proliferate in response to stimulator cells, and progress or success (or lack thereof) of an activation reaction can be assessed. In certain non-limiting examples of a cell proliferation assay, cells can be pulsed with a radiolabeled nucleotide (e.g., tritiated thymidine), and the amount of radiolabeled nucleotide incorporated into cellular DNA can be assessed (e.g., the higher amount of incorporation the high level of proliferation). An example of such assay is described herein (e.g., Examples section).

In some embodiments, certain assays detect one or more ratios of stimulators (e.g., cytokines) produced during activation reactions. Such ratios can be indicative of the progress or success (or lack thereof) of an activation reaction. In some assay embodiments, a T helper 1 (Th1) to T helper 2 (Th2) cytokine ratio is assessed. A ratio of suitable stimulators can be assessed, and in some embodiments, a ratio between any two of the following stimulators can be determined: IFN-γ, TNF-α, IL-2, IL-4, IL-5 and IL-10. In certain embodiments, a ratio is determined for (i) IFN-γ to IL-10, and/or (ii) TNF-alpha to IL-4.

Certain assays can assess cytotoxic T cell activity by detecting one or more cytokines generated by activated T cells (e.g., granulocyte-macrophage colony-stimulating factor (GM-CSF), interferon (IFN) γ, tumor necrosis factor (TNF) α). In a non-limiting example of an IFN-γ assay, DCs from HLA-A2-positive healthy volunteers can be pulsed with MAGE-3 A2.1 peptide (residues 271-279; FLWGPRALV) on day 4 of culture, followed by transduction with Ad-iCD40 and stimulation with various stimuli on day 5. Autologous T cells can be purified from PBMC by negative selection (Miltenyi Biotec, Auburn, Calif.) and mixed with DCs at DC:T cell ratio 1:3. Cells can be incubated in complete RPMI with 20 U/ml hIL-2 (R&D Systems) and 25 micrograms/ml of MAGE 3 A2.1 peptide. T cells can be restimulated at day 7 and assayed at day 14 of culture. For quantification, flat-bottom, 96-well nitrocellulose plates (MultiScreen-HA; Millipore, Bedford, Mass.) can be coated with IFN-γ mAb (2 μg/ml, 1-D1K; Mabtech, Stockholm, Sweden) and incubated overnight at 4° C. After washings with PBS containing 0.05% TWEEN 20, plates can be blocked with complete RPMI for 2 h at 37° C. A total of $1\times10^5$ presensitized CD8+ T effector cells can be added to each well and incubated for 20 h with 25 micrograms/ml peptides. Plates then can be washed thoroughly with PBS containing 0.05% Tween 20, and anti-IFN-mAb (0.2 μg/ml, 7-B6-1-biotin; Mabtech) can be added to each well. After incubation for 2 h at 37° C., plates can be washed and developed with streptavidin-alkaline phosphatase (1 μg/ml; Mabtech) for 1 h at room temperature. After washing, substrate (3-amino-9-ethyl-carbazole; Sigma-Aldrich) can be added and incubated for 5 min. Plate membranes displaying dark-pink spots that can be scanned and analyzed by ZellNet Consulting Inc. (Fort Lee, N.J.).

Certain assays for cytotoxic T cell activity can assess the cell-killing (e.g., cell lysis) activity of activated T cells. Certain assays detect a component inside a cell released when it is killed by an activated T cell, and one example is a chromium release assay. In a non-limiting example of a chromium release assay, antigen recognition can be assessed using target cells labeled with 51 Chromium (Amersham) for 1 h at 37° C. and washed three times. Labeled target cells (5000 cells in 50 μl) can be then added to effector cells (100 μl) at certain effector:target cell ratios in V-bottom microwell plates at certain concentrations. Supernatants can be harvested after 6-h incubation at 37° C., and chromium release is measured using MicroBeta Trilux counter (Perkin-Elmer Inc, Torrance Calif.). Assays involving LNCaP cells can be run for 18 hours. The percentage of specific lysis is calculated as:

$$100*[(\text{experimental}-\text{spontaneous release})/(\text{maximum}-\text{spontaneous release})].$$

Specificity of activated T cells also can be assessed by methods known in the art. For example, a tetramer staining assay can be utilized to determine activated T cell specificity. In a non-limiting example of a tetramer staining assay, HLA-A2 tetramers assembled with MAGE-3.A2 peptide (FLWG-PRALV) can be obtained from Baylor College of Medicine Tetramer Core Facility (Houston, Tex.). Presensitized CD8+ T cells in 50 μl of PBS containing 0.5% FCS can be stained with PE-labeled tetramer for 15 min on ice before addition of FITC-CD8 mAb (BD Biosciences). After washing, results can be analyzed by flow cytometry. The assay described in this paragraph utilizes a particular peptide (i.e., MAGE-3.A2 peptide) that may or may not be applicable to certain therapeutic methods and compositions described herein, and another relevant peptide may be substituted.

A polarization assay can be utilized to determine whether antigen presenting cells are capable of activating T cells from a donor by assaying for activated cells that display CD4 and IFN-γ markers. In a non-limiting example of a polarization assay, naïve CD4+CD45RA+ T-cells from HLA-DR11.5-positive donors (genotyped using FASTYPE HLA-DNA SSP typing kit; BioSynthesis, Lewisville, Tex.) can be isolated by negative selection using naïve CD4+ T cell isolation kit (Miltenyi Biotec, Auburn, Calif.). T cells can be stimulated with autologous DCs pulsed with tetanus toxoid (5 FU/ml) and stimulated with various stimuli at a stimulator to responder ratio of 1:10. After 7 days, T cells can be restimulated with autologous DCs pulsed with the HLA-DR11.5-restricted helper peptide TTp30. Cells can be stained with PE-anti-CD4 Ab (BD Biosciences), fixed and permeabilized using BD Cytofix/Cytoperm kit (BD Biosciences), then stained with hIFN-γ mAb (eBioscience, San Diego, Calif.) and analyzed by flow cytometry. Supernatants can be analyzed using human TH1/TH2 BD Cytometric Bead Array Flex Set on BD FACSArray Bioanalyzer (BD Biosciences). The assay described in this paragraph utilizes a particular peptide (i.e., peptide TTp30) that may or may not be applicable to certain therapeutic methods and compositions described herein, and another relevant peptide may be substituted (e.g., another HLA peptide may be utilized and donors having an HLA that presents the peptide can be selected).

Any suitable assay can be utilized to determine the activity of DCs as they are differentiated. A migration assay (e.g., chemotaxis assay) can be utilized to determine whether viable dendritic cells are present in a culture medium, for example, and methods for assessing DC migration are known in the art. In a non-limiting example, migration of DCs can be measured by passage through a polycarbonate filter with 8 micrometer pore size in 96-Multiwell HTS Fluoroblok plates (BD Biosciences). Assay medium (250 μL) containing 100 ng/ml CCL19 (R&D Systems) or assay medium alone (as a control for spontaneous migration) can be loaded into a lower chamber. DCs (50,000) can be labeled with Green-CMFDA cell tracker (Invitrogen), unstimulated or stimulated for 48 h with the indicated reagents, and can be added to an upper chamber in a total volume of 50 μL for 1 hour at 37° C. and 5% $CO_2$. Fluorescence of cells, which have migrated through the microporous membrane, can be measured using the FLUOstar OPTIMA reader (BMG Labtech Inc., Durham, N.C.). The mean fluorescence of spontaneously migrated cells can be subtracted from the total number of migrated cells for each condition.

Administration of Cytotoxic T Cells and Treatments

Cytotoxic T cells herein provided may be formulated in a pharmaceutical composition in any manner appropriate for administration to a subject. A composition may be prepared by washing cells one or more times with a medium compatible with cells of the subject (e.g., phosphate buffered saline). Cells also may be combined with components that form a time-release matrix or gel in some embodiments. Non-limiting examples of components that form a matrix include, without limitation, fibrin, proteoglycans or polysaccharides. A matrix sometimes is a thrombus or plasma clot in some embodiments.

Compositions comprising cytotoxic T cells can be administered to patients for treatment of a condition. The cytotoxic T cells often are administered to the same patient, from whom stimulator cells were derived used to generated the T cells. In some embodiments, cytotoxic T cells are administered to a subject who is not the patient from which the stimulator cells used to prepare the T cells were derived.

A composition can be administered to a subject in need thereof in amount effective to treat a cell proliferative condition (e.g., cancer, tumor), inflammation condition or autoimmune condition. The terms "treat" and "treating" as used herein refer to (i) preventing a disease or condition from occurring (e.g. prophylaxis); (ii) inhibiting the disease or condition or arresting its development; (iii) relieving the disease or condition; and/or (iv) ameliorating, alleviating, lessening, and removing symptoms of the disease or condition. The terms also can refer to reducing or stopping a cell proliferation rate (e.g., slowing or halting tumor growth) or reducing the number of proliferating cancer cells (e.g., removing part or all of a tumor).

Given that activated T cells often are alloreactive and can kill cells of a patient that present patient antigen to which the cytotoxic T cells are sensitized, the T cells often are administered in a manner that does not lead to significant killing of non-afflicted tissue. Activated T cells also often are administered to a part of the body that does not rapidly inactivate the administered T cells. In certain embodiments, activated T cells can be administered to an immuno-privileged region of a subject. An immuno-privileged region sometimes is characterized by one or more of the following non-limiting features: low expression of MHC molecules; increased expression of surface molecules that inhibit complement activation; local production of immunosuppressive cytokines such as TGF-beta; presence of neuropeptides; and constitutive expression of Fas ligand that controls the entry of Fas-expressing lymphoid cells. An immuno-privileged region can be semi-immuno-privileged, where a minority subset of cells are subject to the immune system. In certain embodiments, a composition is administered to the brain, an immuno-privileged region, to treat a cancer, where cancer cells are the predominant antigen presenting cells and are preferentially killed by the T cells over non-cancer cells. Other non-limiting examples of immuno-privileged regions of the body are portions of the eye (e.g., ocular anterior chamber, ocular uveal tract, cornea, central nervous system), testis, liver and pregnant uterus.

Activated T cells also may be administered to another part of the body that is not immuno-privileged, in certain embodiments. In some embodiments, activated T cells are administered to a part of the body where T cells are not substantially cleared or inactivated. For example, activated T cells may be administered directly to a solid tumor mass, where the T cells may not be readily transported to other parts of the body or inactivated (e.g., injected into the tumor). Compositions can be administered to the subject at a site of a tumor, in some embodiments. Diffuse cancers are treatable where the composition is maintained in contact with cells within a limited area (e.g., within the cranial cavity), in certain embodiments.

Cytotoxic T cells are delivered in any suitable manner. A dose can be administered by any suitable method, including, but not limited to, systemic administration, intratumoral administration, bolus injection, infusion, convection enhanced delivery, blood-brain barrier disruption, intracarotid injection, implant delivery (e.g., cytoimplant), and combinations thereof (e.g., blood-brain barrier disruption followed by intracarotid injection). Blood-brain barrier disruption can include, without limitation, osmotic disruption; use of vasoactive substances (e.g., bradykinin); exposure to high intensity focused ultrasound (HIFU); use of endogenous transport systems, including carrier-mediated transporters such as glucose and amino acid carriers, for example; receptor-mediated transcytosis for insulin or transferrin; blocking of active efflux transporters such as p-glycoprotein, for example; intracerebral implantation; convection-enhanced distribution; use of a liposome; and combinations of the foregoing. Cytotoxic T cells are delivered by injection in a suitable volume (e.g., about 5 ml to about 20 ml volume (e.g., about 10 ml volume)), and in a suitable medium (e.g., saline; phosphate buffered saline). An implant sometimes includes a gel or matrix. In certain embodiments, an infusion is via a catheter and/or reservoir (e.g., Rickham, Ommaya reservoir).

The dose given is an amount "effective" in bringing about a desired therapeutic response (e.g., destruction of cancer cells) by the alloreactive cytotoxic T cells in the composition. For pharmaceutical compositions described herein, an effective dose often falls within the range of about $10^8$ to $10^{11}$ cells. The cells can include allogeneic stimulators and responders, or may be purified to a certain degree (e.g., substantially pure) for responder cells (e.g., activated T cells). About $1\times10^9$ to about $5\times10^{10}$ cells sometimes are delivered, in some embodiments, and in certain embodiments, about $10^8$ to about $10^{10}$ cells, about $10^9$ to about $10^{11}$ cells, about $10^8$ to about $10^9$ cells, about $10^9$ to about $10^{10}$ cells, about $10^{10}$ to about $10^{11}$ cells, about $2\times10^9$ to about $2\times10^{10}$ cells, or about $2\times10^9$ to about $2\times10^{10}$ cells, are delivered. Multiple doses can be delivered over time to achieve a desired effect, and often, each dose delivers an effective amount of cells. Cells in the composition delivered can contain a mixture of responder cells and stimulator cells, sometimes in a ratio between about 1:1 and about 100:1, and sometimes in a ratio between about 5:1 and about 25:1, and sometimes about 10:1. In some embodiments, cytotoxic T cells are purified to a certain degree (e.g., cytotoxic T cells are about 30% or more of cells in the composition (e.g., from about 30% to about 95% or more cells in the composition)). Any number of component cells or other constituents may be used, as long as the composition is effective as a whole. The number of cells utilized in a composition also can depend culture conditions and other factors during preparation.

A pharmaceutical composition provided herein may be administered following, preceding, in lieu of, or in combination with, one or more other therapies relating to generating an immune response or treating a condition in the subject (e.g., cancer). For example, the subject may previously or concurrently be treated by chemotherapy, radiation therapy, surgery, cell therapy and/or a forms of immunotherapy and adoptive transfer. Where such modalities are used, they often are employed in a way or at a time that does not interfere with the immunogenicity of compositions described herein. The subject also may have been administered another vaccine or other composition to stimulate an immune response. Such alternative compositions may include tumor antigen vaccines, nucleic acid vaccines encoding tumor antigens, anti-idiotype vaccines, and other types of cellular vaccines, including cytokine-expressing tumor cell lines. Non-limiting examples of chemotherapeutic agents include, without limitation, alkylating agents (e.g., cisplatin); antimetabolites (e.g., purine, pyrimidine); plant alkaloids and terpenoids (e.g., taxanes); vinca alkaloids and topoisomerase inhibitors. Surgeries sometimes are tumor removal or cytoreduction, the latter of which is removal of as much tumor as possible to reduce the number of tumor cells available for proliferation. Surgeries include, without limitation, surgery through the nasal cavity (trans-nasal), surgery through the skull base (trans-sphenoidal), and craniotomy (opening of the skull). Radiotherapies include, without limitation, external beam radiotherapy (EBRT or XBRT) or teletherapy, brachytherapy or sealed source radiotherapy, systemic radioisotope therapy or unsealed source radiotherapy, virtual simulation, 3-dimensional conformal radiotherapy, intensity-modulated radiotherapy, particle therapy and radioisotope therapy. Conventional external beam radiotherapy (2DXRT) often is delivered via two-dimensional beams using linear accelerator machines. Stereotactic radiotherapy is a type of external beam radiotherapy that focuses high doses of radiation within the body (e.g., cyberknife, gamma knife and Novalis Tx). Cell therapies include, without limitation, administration alone or in combination of dendritic cells, alloreactive cytotoxic T-lymphocytes, stem cells, and monocytes.

A composition may be administered in intervals, and may be replenished one or more times. A composition may be administered, one or more times, for example, about one to about 20 times. The time interval between each administration independently may be of days or even months, for example 1 month to about 6 months, or about 1 day to about 60 days, or about 1 day to about 7 days. Subsequent administration of a composition described herein can boost immunologic activity and therapeutic activity.

Timing for administering compositions is within the judgment of a managing physician, and depends on the clinical condition of the patient, the objectives of treatment, and concurrent therapies also being administered, for example. Suitable methods of immunological monitoring include a one-way mixed lymphocyte reaction (MLR) using patient lymphoblasts as effectors and tumor cells as target cells. An immunologic reaction also may manifest by a delayed inflammatory response at an injection site or implantation site. Suitable methods of monitoring of a tumor are selected depending on the tumor type and characteristics, and may include CT scan, magnetic resonance imaging (MRI), radioscintigraphy with a suitable imaging agent, monitoring of circulating tumor marker antigens, and the subject's clinical response. Additional doses may be given, such as on a monthly or weekly basis, until the desired effect is achieved. Thereafter, and particularly when an immunological or clinical benefit appears to subside, additional booster or maintenance doses may be administered.

When multiple compositions are administered to a patient, it is possible that an anti-allotype response could manifest. The use of a mixture of allogeneic cells from a plurality of donors, and the use of different allogeneic cell populations in each dose, are strategies that can help minimize the occurrence of an anti-allotype response. During the course of therapy, a subject sometimes is evaluated on a regular basis for general side effects such as a febrile response. Side effects are managed with appropriate supportive clinical care.

In some embodiments, methods and compositions provided herein are utilized to treat a cell proliferative condition. Examples of cell proliferation disorders, include, without limitation, cancers of the colorectum, breast, lung, liver, pancreas, lymph node, colon, prostate, brain, head and neck, skin, liver, kidney, and heart. Examples of cancers include hematopoietic neoplastic disorders, which are diseases involving hyperplastic/neoplastic cells of hematopoietic origin (e.g., arising from myeloid, lymphoid or erythroid lineages, or precursor cells thereof). The diseases can arise from poorly differentiated acute leukemias, e.g., erythroblastic leukemia and acute megakaryoblastic leukemia. Additional myeloid disorders include, but are not limited to, acute promyeloid leukemia (APML), acute myelogenous leukemia (AML) and chronic myelogenous leukemia (CML) (reviewed in Vaickus, Crit. Rev. in Oncol./Hemotol. 11:267-297 (1991)); lymphoid malignancies include, but are not limited to acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease. In a particular embodiment, a cell proliferative disorder is non-endocrine tumor or endocrine tumors. Illustrative examples of non-endocrine tumors include but are not limited to adenocarcinomas, acinar cell carcinomas, adenosquamous carcinomas, giant cell tumors, intraductal papillary mucinous neoplasms, mucinous cystadenocarcinomas, pancreatoblastomas, serous cystadenomas, solid and pseudopapillary tumors. An endocrine tumor may be an islet cell tumor. Also included are pancreatic tumors (e.g., as pancreatic ductal adenocarcinomas); lung tumors (e.g., small and large cell adenocarcinomas, squamous cell carcinoma, and bronchoalveolar carcinoma); colon tumors (e.g., epithelial adenocarcinoma, and liver metastases of these tumors); liver tumors (e.g., hepatoma, cholangiocarcinoma); breast tumors (e.g., ductal and lobular adenocarcinoma); gynecologic tumors (e.g., squamous and adenocarcinoma of the uterine cervix, anal uterine and ovarian epithelial adenocarcinoma); prostate tumors (e.g., prostatic adenocarcinoma); bladder tumors (e.g., transitional, squamous cell carcinoma); tumors of the reticuloendothelial system (RES) (e.g., B and T cell lymphoma (nodular and diffuse), plasmacytoma and acute and chronic leukemia); skin tumors (e.g., malignant melanoma); and soft tissue tumors (e.g., soft tissue sarcoma and leiomyosarcoma).

A cell proliferation disorder may be a tumor in an immune-privileged site, such as the brain, for example. A brain tumor is an abnormal growth of cells within the brain or inside the skull, which can be cancerous or non-cancerous (benign). A brain tumor is any intracranial tumor having (and/or arising from) abnormal and uncontrolled cell division, often in the brain itself (neurons, glial cells (astrocytes, oligodendrocytes, ependymal cells), lymphatic tissue, blood vessels), in the cranial nerves (myelin-producing Schwann cells), in the brain envelopes (meninges), skull, pituitary and pineal gland, or spread from cancers primarily located in other organs (metastatic tumors). Primary brain tumors sometimes are located infratentorially in the posterior cranial fossa (often in children) and in the anterior two-thirds of the cerebral hemispheres or supratentorial location (often in adults), although they can affect any part of the brain. Non-limiting types of brain tumors include glioma (e.g., mixed glioma), glioblastoma (e.g., glioblastoma multiforme), astrocytoma (e.g., anaplastic astrocytoma), oligodendroglioma, medulloblastoma, ependymoma, brain stem tumors, primitive neural ectodermal tumor, and pineal region tumors.

As certain embodiments are directed to administering a composition containing cytotoxic T cells can be administered to an immuno-privileged region of a subject, any disorder occurring in such a region can be treated. For example, a disorder of the eye, liver, testis or pregnant uterus amenable to treatment by alloreactive cytotoxic T cells can be treated with a composition of cytotoxic T cells described herein.

Certain matters are considered when compositions described herein are utilized to treat a brain tumor. If a tumor mass is resectable or partly resectable, then the composition can be administered at or near the site or in a cavity generated by the resection. If a brain tumor is completely removed it still often is beneficial to administer the composition to surrounding tissue to kill remaining cancer cells. A convenient time to administer alloactivated cells to a resectable site is during the time of surgery, in some embodiments. To keep the cells at the site until completion of the surgical procedure, it is convenient to administer the cells in a pharmaceutically compatible artificial gel, or in clotted plasma.

When the solid tumor mass is not resectable, or where less invasive procedures are desired, the composition can be injected at or near the tumor site through a needle. For deeper sites, the needle can be positioned using ultrasound, radioscintigraphy, or some other imaging technique, alone or in combination with the use of an appropriate scope or cannula. For such applications, the cell population is conveniently administered when suspended in isotonic saline or a neutral buffer in a suitable volume (e.g., about 5 to about 20 ml (e.g., 10 ml)).

EXAMPLES

The examples set forth below illustrate certain embodiments and do not limit the invention.

Example 1

Cellular Therapy Studies with Autologous and Allogeneic Effector Cells

MHC can Act as a Glioma Directed Antigen.

These studies examine low-passage glioma cell explants by flow cytometry to assess their MHC Class I and II expression. Single cell suspensions were prepared from dissociated primary brain tumor specimens and placed into culture. From these specimens, tumor cells plated and glia did not. Fresh normal brain cells were also derived from temporal tip lobectomy specimens from seizure patients or from autopsy tissue (<8 hr). Brain tumor cell explants expressed high levels of MHC Class I antigens (93-100% positive; mean fluorescence intensity or MFI range 4-662), and little to no MHC Class II (0.1-7% positive; MFI all below 2 or negative). Normal brain did not express, or expressed little, Class I (0.5-15%; MFI<2) or II (1-5%; MFI<2.3) antigens. This suggests that patient MHC can act as a brain tumor directed antigen in the brain. Thus, alloCTL directed against tumor-bearing host MHC could be used for adoptive immunotherapy treatment if given intratumorally, since lysis of cells should be largely restricted to tumor cells while leaving normal brain cells intact. Other cells in the brain, such as endothelial cells, microglia and reactive astrocytes may express some MHC; however, even if some of these accessory cells were injured, they were capable of repopulating in the brain.

In Vivo Animal Studies Using alloCTL for Treatment of Rat Gliomas.

Evidence in a rat model indicated that there was no occurrence of extreme inflammatory reactions to multiple installations of alloCTL into normal brain, and that very focal inflammatory responses result when they were placed into tumor-bearing regions of brain. Implantation of cannulas into the brains of Fischer 344 rats gave us an experimental model in which to study trafficking of adoptively transferred alloCTL in cannulated brain. It was found that the alloCTL were capable of moving through brain parenchyma, a feature necessary if infiltrating pockets of tumor cells in brain neuropil are to be eliminated. Trafficking of alloCTL in the caudate-putamen area was shown when placed into brain parenchyma in a site far removed from the cannula and instillation track (right frontal brain). Furthermore, efficacy of alloCTL in eradicating new and established intracranial (i.c.) rat brain tumors was demonstrated. Repeated i.c. infusions of alloCTL (using either single or multiple donors) were tolerated well by the animals. Adoptive transfer of alloCTL into tumor-bearing animals resulted in all animals exhibiting extended survival compared to sham treated controls and, in addition, a cure rate of between 20-35%, which was something not clearly observed with LAK cells. Despite the immunogenicity documented for the 9L tumor model, alloCTL-treated animals that succumbed to tumor exhibited an increased survival relative to sham-treated controls.

In Vitro Studies Using Human alloCTL to Lyse Glioma Cells.

Figure 7:
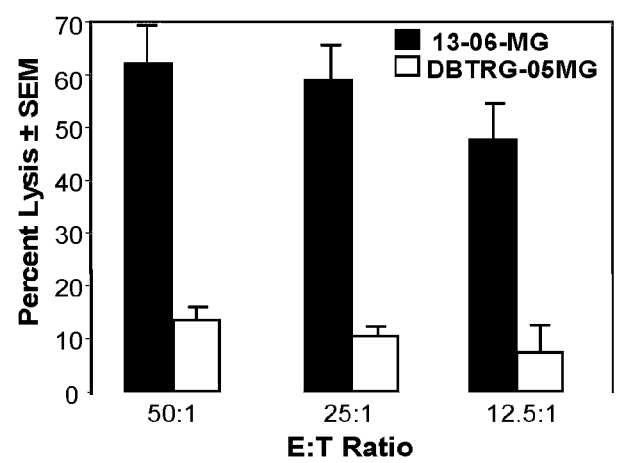
FIG. 7 shows that, in some embodiments, specificity of alloCTL for relevant glioma target can be demonstrated in 51Cr-release cytotoxicity assays.

Human tumor specimens were often unavailable to use for sensitization of tumor-specific CTL. However, lymphocytes that do express high levels of HLA can be isolated and expanded from patients. Since brain tumor cells display HLA class I antigens and normal brain cells do not, HLA can act as tumor-directed antigens if alloCTL are used for brain tumor therapy.

alloCTL are cytolytic toward relevant tumor target cells and demonstrate specificity as determined by cold target inhibition assays and by chromium-release cytotoxicity assays with blocking antibodies to class I molecules and to the T-cell receptor. With reference to FIG. 7, specificity of alloCTL for relevant glioma target is demonstrated in 51Cr-release cytotoxicity assays. CTL specificity is demonstrated by showing that alloCTL, directed to the HLA antigens of patient 13-06, is more capable of lysing that patient's glioma cells (13-06-MG), than another person's glioma cells (DBTRG-05MG) having 2 HLA alleles in common with 13-06-MG. 51Cr-release assays are the standard for determining CTL. It is demonstrated that normal brain cells are not targets of alloCTL directed toward the HLA antigen of the donor; it is also demonstrated that nearly 100% of the cells isolated from 18 glioma cell explants displayed HLA class I antigen at variable relative antigen densities. Furthermore, if the display of HLA on gliomas is upregulated with exogenous interferon, or if the tumor cells are transduced with vectors coding for the interferon gene, reflective of what may occur in a proinflammatory environment, they are better targets of alloCTL. In addition, little change in glioma lysis by alloCTL occurs when co-incubated in the presence of dexamethasone. Thus, short-term lysis by the alloCTL is not affected even if the patients treated were on immunosuppressive steroid therapy.

Generation of alloCTL in Artificial Capillary Systems.

alloCTL generation in Baxter LifeCell Tissue Culture Bags has been developed as an alternative to the artificial capillary systems (FDA BB-IND 5423 reactivation materials, 12/2007). Protocols were developed for the ex vivo expansion of stimulator lymphocytes from brain tumor patients using non-specific stimulation (OKT3 & IL-2) and growth in artificial capillary systems. Furthermore, an efficient and cost-effective method has been developed to generate responder alloCTL, also in artificial capillary systems. Responder lymphocytes from healthy unrelated donors, immunologically distinct from the patient, were used as a source of precursor alloCTL, and a one-way mixed lymphocyte reaction (MLR) proceeded with irradiated patient lymphocytes as sensitizing cells.

In Vitro Studies with Immunoresistant Glioma Cell Clones.

Selective pressure with multiple alloCTL preparations was applied in vitro to a glioma cell explant derived from a patient at initial diagnosis. Stably immunoresistant glioma cell clones were obtained only after the application of continuous in vitro selective pressure, but not with intermittent selective pressure. The latter mimicked the in vivo treatment where patients were given alloCTL infusions a month apart over a 10 month period. This suggests that patients do not build up a tolerance to repeated intracranial administrations of alloCTL when made from single or multiple allodonors.

In summary, it was demonstrated that:

alloCTL precursors (PBMC) directed against an MHC mismatch are readily transformed into tumoricidal CTL in vitro, alloCTL placed intracranially are protected long enough in this immunologically semi privileged site from a host immune response to perform their effector functions, alloCTL are capable of trafficking through brain tumor tissue to reach infiltrating tumor cells, multiple alloCTL administrations are more efficacious in reducing tumor burden than a single administration, single or multiple donors of precursor alloCTL can be used for the therapy of one patient, repeated, frequent infusions maintain alloCTL presence in the brain (20% of injected dose remained at 1 week), treatment with ex vivo activated alloCTL may be effective in patients on steroids to alleviate edema, patient lymphocytes can be used in place of tumor as the sensitizing cells, brain tumor cells display high levels of MHC antigen and normal brain cells very little, therapeutic numbers of alloCTL can be produced in artificial capillary systems (hollow fiber bioreactors) and in tissue culture bags, there is little likelihood that patients will build up a tolerance to intermittently-applied alloCTL preparations.

Example 2

Clinical Experience

Pilot Phase I Clinical Trial with Intratumorally Administered alloCTL

Patient Profiles.

Six recurrent glioma patients (ages 26-46 years) were treated with intracavitary alloCTL and interleukin-2 (IL-2). With toxicity as the primary concern, patients with a variety of histological types were allowed to enroll (see Table 1). The pathologic diagnoses included three recurrent glioblastoma multiformes (GBMs), two anaplastic oligodendrogliomas, and one anaplastic astrocytoma. All had failed treatment consisting of 1 to 3 debulking surgeries and standard radiation (>5000 cGy). All but one also had failed prior chemotherapy and two had additionally failed gamma knife treatment. At entry, the choices were hospice care or experimental therapy.

TABLE 1

Patients, Immune Therapy, & Status

| Patient Number/ Tumor histology | # of alloCTL cycles | Time to tumor progression/Survival |
| --- | --- | --- |
| BTP1/Glioblastoma | 2 | TTP 3 mos, recurrence at distant site, died at 4 mo |
| BTP2/Glioblastoma | 2 | TTP 3 mos, local tumor recurrence, died at 4 mo |
| BTP3/Anaplastic oligodendroglioma | 5 | TTP 32 mos, died at 40 mo |
| BTP4/Anaplastic oligodendroglioma | 2 | Withdrew from study, alive with stable disease at 14 yr |

TABLE 1-continued

Patients, Immune Therapy, & Status

| Patient Number/ Tumor histology | # of alloCTL cycles | Time to tumor progression/Survival |
| --- | --- | --- |
| BTP5/Anaplastic astrocytoma | 5 | Completed protocol, live with stable disease at 14 yr |
| BTP6/Glioblastoma | 1 | TTP <1 mo, died at 1 month |

AlloCTL Treatment Cycles and Clinical Status.

Five treatment cycles were possible. Each cycle was given every other month and involved 2 3 intracranial infusions of alloCTL within a two week period. Different donors were used at each cycle that differed from the patient by 2-3 HLA, AB loci (Table 2, matching loci are shaded). All three GBM patients had tumor recurrence and died before completing 5 cycles. Two other patients (BTP3 and BTP5) completed the entire 10-month series. BTP3, with an anaplastic oligodendroglioma, did well until tumor progression was noted on MRI at 32 months; he died at 40 months from the start of immunotherapy. Patient BTP4, also with an anaplastic oligodendroglioma, experienced side effects during the second treatment cycle and withdrew from the protocol. She was still alive, with no evidence of tumor progression at fourteen years from start of immunotherapy. BTP5, with an anaplastic astrocytoma, was also alive at fourteen years with no signs of tumor recurrence. The three Grade III glioma patients received the highest number of alloCTL.

Short-Term and Long-Term Toxicity.

The toxicity and follow-up on patients treated in this pilot trial were reported. The side-effects of the treatment were transient and tolerable (headache, lethargy, fever and nausea). No long-term side effects (as determined by neurologic exams and Karnofsky performance scores) were experienced by the patients. Although development of GVH was of concern, no signs or symptoms indicating development of GVH were recorded from the multiple placements of alloCTL.

AlloCTL Infusate Numbers, Phenotypes, and HLA Types.

The alloCTL numbers and viabilities given to the patients, along with the cumulative phenotypic expression of the CTL infusates were previously summarized. The total lymphocyte doses per patient ranged from $1 \times 10^8$ to $5.2 \times 10^9$. Donors of the precursor alloCTL differed by minimally 2 HLA-AB loci from the host. CTL cultures between 12 to 35 days after sensitization were used for therapy, but in most instances the 2-3 infusions occurred between days 14-21. CTL were used as effectors and activated lymphocyte blasts from the patient and donor were used as targets in 4-hr $^{51}$Cr-release assays. The percent lysis of the patient targets ranged from 29-64% at a 10:1 effector to target (E:T) ratio; whereas lysis of the irrelevant donor targets was zero.

Neuroimaging and Follow-Up.

The gadolinium-enhanced MRI of all patients, upon entrance into this study, had to show unequivocal evidence of tumor progression when measured and compared to a prior scan. Follow-up MRI scans from BTP3, who died at 40 months post-immune therapy were examined. Two patients, BTP4 and BTP5, were still alive with stable disease at 14 years post-immune therapy and routinely receive follow-up; their MRI scans show no change in a series of contrast T1-weighted MRI scans taken.

TABLE 2

HLA types of patients and donors

| | Patient | | | | | | | | | | |
|---|---|---|---|---|---|---|---|---|---|---|---|
| | BTP1 | | | BTP2 | | | BTP3 | | | | |
| | CYCLE | | | | | | | | | | |
| | | 1 | 2 | | 1 | 2 | | 1 | 2 | 3 | 4 | 5 |
| HLA type | SELF | Donor 1 | Donor 2 | SELF | Donor 1 | Donor 2 | SELF | Donor 1 | Donor 2 | Donor 3 | Donor 4 | Donor 5 |
| A1 | | | | | | XX | | X | | | | |
| A2 | X | | X | X | | | | X | XX | X | | |
| A3 | | | X | | X | | | | | X | | X |
| A11 | | X | | | | | | | | | X | |
| A24 | | | | | | X | | | | | | |
| A26 | | X | | | | | | | | | X | |
| A28 | | | | | | | | | | | | |
| A29 | | | | | | | | | | | | |
| A31 | | | | | | X | | | | | | |
| A32 | | | | | | | | | | | | |
| A33 | | X | | X | | | | | | | | |
| B7 | | X | X | X | | | X | | | | X | |
| B8 | | | | | XX | | X | X | | | X | |
| B13 | | | | | | | | | | | | X |
| B14 | | | | | | | | | | | | |
| B17 | | | | | | | | | | | | |
| B18 | | | | X | | | X | | | | | |
| B27 | | | | | | | | | | | | |
| B38 | | | | | | | | | | | | |
| B41 | | | | | | | | | X | | | |
| B44 | X | | | X | | | | | | | | |
| B49 | | | | | | | | | | | | |
| B50 | | | | | | | | | | | | |
| B51 | | | | | | | | | X | | | |
| B58 | | X | | X | | | | | | | | |
| B60 | X | X | | | | | | | | | X | |
| B62 | | | | | | | | | X | | | |
| B63 | | | | | X | | | | | | | |

| | Patient | | | | | | | | | |
|---|---|---|---|---|---|---|---|---|---|---|
| | BTP4 | | | BTP5 | | | | | | BTP6 |
| | CYCLE | | | | | | | | | |
| | | 1 | 2 | | 1 | 2 | 3 | 4 | 5 | | 1 |
| HLA type | SELF | Donor 1 | Donor 2 | SELF | Donor 1 | Donor 2 | Donor 3 | Donor 4 | Donor 5 | SELF | Donor 1 |
| A1 | | X | | X | | | | X | X | | |
| A2 | | | XX | X | X | | | | | X | |
| A3 | | X | | | X | X | | | | | |
| A11 | | | | | | | | | | | |
| A24 | | | | | | | | | | | |
| A26 | | | | | | | X | X | | | |
| A28 | | | | | | | | | X | | X |
| A29 | | | | | | | X | | | X | X |
| A31 | X | | | | | X | | | | | X |
| A32 | X | | | | | | | | | | |
| A33 | | | | | | | | | | | |
| B7 | | X | | | | XX | | | X | | |
| B8 | | | X | | | | | | | | |
| B13 | | | | | | | | X | | | |
| B14 | | | | | | | | | X | | |
| B17 | X | | | | | | | | | | |
| B18 | | | | | | | | | | | |
| B27 | | | | | | | X | X | | | |
| B38 | | | | | | X | | | | | |
| B41 | | | | | | | X | | | | |
| B44 | | | X | | | | | | | X | |
| B49 | X | | | | | | | | | | |
| B50 | | | | | | | | | | | X |
| B51 | | | | | | X | | | | | |
| B58 | | | | | | | | | | | |
| B60 | X | | | | | | | | | X | |
| B62 | | | XX | | | | | | | | |
| B63 | | | | | | | | | | | |

Tumor Bank/HLA-Typed Tumors.

Seventeen low-passage cultured glioma cell explants and established glioma cell lines that were characterized for HLA and tumor associated antigens (TAA) are provided. For seven of them the HLA was typed at class I and II alleles by molecular analyses using RT-PCR SSP (Table 3). For some patients lymphocyte specimens were matched to go along with the tumor.

TABLE 3

HLA-Typed Cultured Glioma Cells 04-11-MG: A*0101; B*08(01, 19N),*5701; Cw*0602, *07(01, 06, 18); DPB1*0101, *0301; DRB1*0301, *1302; DRB3*0101, *0301; DQB1*0201, *0604
D-645MG: A*02(05, 14), 23(01, 02); B*35(01, 42), *4901; Cw*04(01, 09N), *07(01, 06, 18); DRB1*0101, *0405, DRB4*0103; DQB1*0302,*0501
DBTRG05-MG: A*02(01, 04, 09), 68(01, 11N, 23); B*35(01, 42), *3801; Cw*12(03, 04), 15(02, 07);
DR B1*0402, *14(01, 39); DR B3, B4; DQ B1*0302, *0503
NR103: A*0201, B*07(02, 05, 06), *40(01, 33); Cw*0304, *0702; DPB1*0401; DRB1*0408, *1501; DRB4*0103, 5*0101; DQB1*0301, *0602
NR106: A*0201; B*1501; Cw*0304;
DPB1*1301; DRB1*0405; DRB4*0105; DQB1*0303
NR213: A*0201; B*44(02, 10N, 27), *5501; Cw*0303, *05(01, 03); DPB1*0401, *1101; DRB1*0401, *1501; DRB4*0103, 5*(0101); DQB1*0301, *0602
T98G: A*0201; B*3503, *3906; Cw*04(01, 09N), *0702; DPB1*0301,*0401; DRB1*0801, *1201; DRB3*0202; DQB1*0302, *0402

Percentages of CD3+ T Cells within the alloCTL Preparations Displaying Activated Markers (CD69+/IFN-γ).

Precursor alloCTL were combined with inactivated sensitizing lymphocyte blasts at a responder to stimulator (R:S) ratio of 10:1. At 14 days after the initial one-way MLR, the cells were restimulated with OKT-3 (10 ng/ml) overnight before analysis using the BD Fast Immune Kit. The kit contained surface markers for CD3-APC, CD8-PercP-Cy5.5, CD69-PE and provided for intracellular interferon-γ (IFNγ-FITC) determination. CD69 is an early activation marker and IFN-γ generally sorts with CD69+ cells.

It was informative to look at those subsets that also expressed CD69 and intracellular IFN-γ. When the activated CD69+ marker was associated with each of these two subpopulations, they had mean fluorescence intensities (MFI) for IFN-γ that greatly exceeded those MFIs for the individual CD3+/CD4+ (1.5 fold) and CD3+/CD8+ (5.2 fold) subpopulations (see Table 4).

TABLE 4 alloCTL Subset Analyses

| alloCTL Phenotype | IFN-γ MFI |
|---|---|
| CD3+ | 2503 |
| CD3+/CD8+ | 1720 |
| CD3+/CD8+/CD69+ | 8950 |
| CD3+/CD4+ | 2600 |
| CD3+/CD4+/CD69+ | 3792 |

Response by the alloCTL CD8+ Subset to Incubation with Relevant Target.

An example is provided in Table 5 from a different alloCTL preparation. The subset of CD3+/CD8+ cells that were also CD69+ was 10.5%, and half of that subset (i.e., 52.1%) also expressed IFN-γ at a MFI equal to 500. When that same alloCTL preparation was incubated with relevant glioma targets for 18 hr, the percentage of CD3+/CD8+/CD69+ cells went up 6-fold. A third of those cells also expressed IFN-γ at a 5-fold higher MFI. When alloCTL from the same preparation were analyzed for CD3+/CD4+/CD69+ cells, upon incubation with relevant target the percentage rose 2.3-fold, but less than 1% of them were IFN-γ positive. Thus, the CD3+/CD8+ cells react by producing proinflammatory IFN-γ upon exposure to the relevant HLA glioma antigens.

Flow cytometric analyses are quite sensitive and can detect phenotypic subsets present in small percentages. The CTL precursor frequency to major antigen can be as high as 10%. With approximately 7-14 doublings possible over a 2 to 3 week alloCTL culture period, enrichment of the alloCTL effectors responding to restimulation should be detectable in the alloCTL pool. Examining the fold increases in the activated CD3/CD69 subsets producing IFN-γ upon exposure to relevant target cells is proposed.

7-AAD Flow Cytometric Assays Determine Cell Injury Caused by alloCTL to Targets Displaying Relevant HLA Antigen(s).

During cell injury, the plasma membrane becomes increasingly permeable and a fluorescent DNA dye, 7-AAD that selectively binds to guanosine/cytosine regions of the DNA, is taken up by the cells in proportion to the degree of injury. Scattergrams are generated from this flow cytometric-based assay that distinguish live, early apoptotic, and dead/late apoptotic cells.

Figure 8:
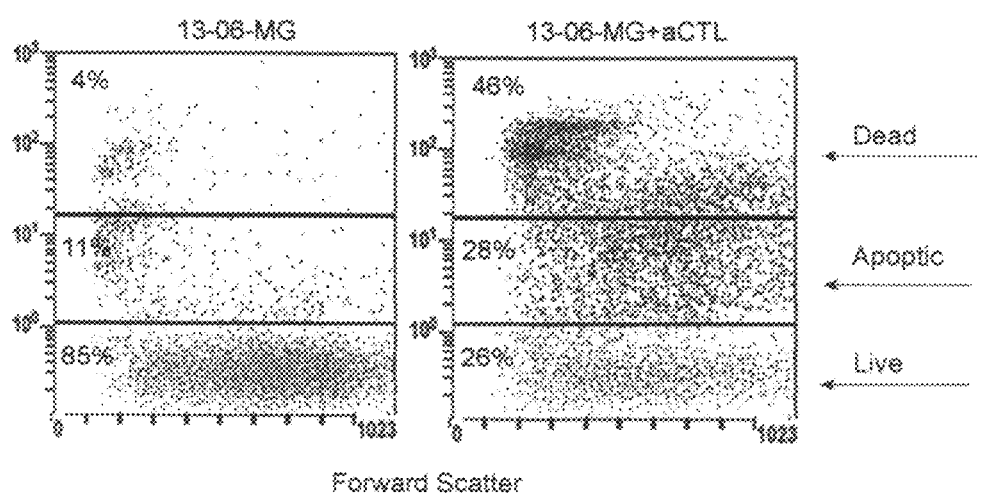
FIG. 8 shows an exemplary detection of apoptotic and necrotic cells by the 7-amino actinomycin D (7AAD) assay.

The images in FIG. 8 show carboxyfluorescein diacetate succinimidyl ester-labeled human 13-06-MG glioma cells that were or were not co-incubated with anti-13-06 alloCTL for 4 hours at an E:T ratio of 10:1. By the 7-AAD assay, the percentages of cell injured (apoptotic and dead) totaled 74% from a starting population that was 85% viable. Significant glioma cell injury occurred within a very short time.

Significant glioma cell injury occurred quite rapidly upon their coincubation with alloCTL. This assay appears to be an alternative assay to the chromium release cytotoxicity assay. Apoptotic/necrotic segregation was confirmed, demonstrating that cells within the "dead region" were positive for propidium iodide, and ≥75% of the cells within the "apoptotic region" stained with annexin-V that binds the early apoptotic marker, phosphatidylserine.

TABLE 5

Phenotypic analysis of activated T-cell subsets within alloCTL before/after exposure to relevant target glioma.

| alloCTL +/− relevant glioma target | T-cell subset phenotype | % of CD3+ cells with phenotype | % of CD3+ subset also IFN-γ+ | IFN-γ MFI |
|---|---|---|---|---|
| alloCTL | CD3+/CD8+/CD69+ | 10.5% | 52.1% | 500 |
| alloCTL + target glioma | CD3+/CD8+/CD69+ | 62.7% | 34.7% | 2543 |
| alloCTL | CD3+/CD4+/CD69+ | 35.3% | 0.7% | 254 |
| alloCTL + target glioma | CD3+/CD4+/CD69+ | 80% | 0.9% | 1605 |

AlloCTL can Induce Glioma Cell Apoptosis and Lysis.

In an vitro morphologic assay of hematoxylin and eosin (H&E) stained cells, glioma cells were exposed to alloCTL directed against the HLA antigens present on the glioma. Additional evidence of the significant cell injury capability of the alloCTL to glioma cells in a short period is visible after only a 4-hr exposure of the alloCTL to the monolayer of glioma cells.

In addition to obvious lysis of glioma cells from the monolayer culture, apoptotic cells are also revealed by their condensed or fragmented nuclei. Vesiculation of cells is also visually apparent. H & E staining morphologically demonstrates apoptotic cells glioma cells exposed to alloCTL. 13-06-MG glioma cells cultured for 4 hours in the absences of alloCTL show normal, non-apoptotic brain tumor cells, which were large in size, contained ample cytoplasm, and had large oval nuclei. 13-06-MG glioma cells co-incubated with anti-13-06-MG alloCTL demonstrate classic morphologic changes: condensed nuclei, fragmented nuclei, apoptotic bodies, and membrane blebbing. There was evidence of the DNA fragmentation of a large glioma cell (CellTracker Orange labeled) caused by T effector cells (CellTracker Green labeled) in close conjunction to the glioma cell. Also, the quick, recycling capability of cytolytic T cells was shown. CTL can rapidly lyse tumor cells. Three tumor cells in contact with one effector cell were lysed in 480 sec. One CTL effector cell staining positive for granzymes was shown in contact with 3 tumor cells. CTL had the ability to "recycle" and lyse more than one tumor cell in a short period when they came into contact with them. In each of the successive panels, one tumor cell bound to the CTL was lysed. Over a span of 480 sec, one CTL bound to three tumor cells induced the lysis of all three targets. [WE DO HAVE IMAGE OF THIS—FIG. 10 FROM NEW PROVISIONAL]

Example 3

Dendritic Cells

Dendritic Cell Studies.

PBMC recovered from melanoma patients were subjected to density gradient centrifugation. The enriched adherent monocyte fraction was cultivated in serum-free AIM-V medium supplemented with rhGM-CSF and rhIL-4 for 6 days. The adherent monocytic cells can be visualized with projections by inverted light microscopy. Inverted light photomicrographs can also depict human monocyte derived, immature DC (based on low CD83 expression) displaying typical membrane projections after one week in vitro cultivation.

Flow cytometry revealed that these DCs were 98% positive for HLA-DR class II and these DCs were also characterized for other costimulatory molecules (see Table 6). In vitro monocyte-derived DCs were characterized by flow cytometry using four color flow cytometry. The third decade expression (MFI) of HLA-DR, CD11c, CD80, CD83, and CD86 surface expression on the DC was noted. They may be classified as immature based on their lower level CD83+ surface expression, but they had high CD11c, CD86, and CD80 expressions.

DCs were capable of macropinocytic function by incubation with dextran-FITC for 60 min at 4° C. and at 37° C. Active uptake was also demonstrated. DCs were tested for their functional ability to uptake fluorescently-labeled dextran. Following removal of 0 minute samples, dextran-FITC was added to DCs. Cells were incubated 60 min at 4° C. or 37° C. After incubation, cells were washed, fixed, and analyzed by flow cytometry. The results supported the active uptake by DC (macropinocytosis).

TABLE 6

DC expression of standard surface markers

| Surface Markers | Percent Positive |
|---|---|
| HLA-DR | 98 |
| CD11c | 98 |
| CD80 | 20-25 |
| CD83 | <1% |
| CD86 | 60-70 |

Dendritic cells are strong activators of the allogeneic lymphocytic response because of their high surface level expression of HLA class I and II and a number of other minor histocompatibility antigen molecules. In order to investigate this functional allogeneic stimulatory capability, standard immature DCs were setup in a one-way lymphocyte-irradiated dendritic cell reaction (LDCR) and the resulting allogeneic lymphocytes were tested for proliferative response. Results show lymphocytes proliferate in response to incubation with irradiated DCs, whereas they do not when incubated with uncultivated monocytes. The proliferative response of allogeneic T cells to DCs. Mean cpm±SD were calculated from three triplicate wells. Enriched, uncultivated monocytes were frozen, stored, and used as control stimulator cells.

It was also demonstrated that DC-lymphocytes interact in vitro after a 4 hr co-incubation. Multiple lymphocytes are also seen in contact with each other. Elongated adherent DCs interacting with small lymphocytes have been observed in vitro. Bifurcation of the DC's terminal end, where it and the lymphocyte are contacting one another, also was noted. Also seen were large adherent DC with projections wrapping around small refractile lymphocytes.

Example 4

Structural Analysis by an Algorithm

Analysis of Mismatched HLA Eplets by an Algorithm: Brain Tumor Patients and their alloCTL Donors Used in the Pilot Clinical Study.

Brain tumor patients (BTP) 3, 4 and 5 treated in the pilot clinical trial exhibited prolonged survival after alloCTL immunotherapy. The patients and donors were serologically HLA typed. Each healthy donor differed by at least two HLA AB loci from the patient. Serological HLA types of the patients and healthy donors were converted to the most likely molecular HLA types based on race/ethnicity. FIG. 1 shows the molecular HLA types of BTP3, 4 and 5, and the HLA types of the donor's whose alloCTL they received during therapy. To determine the eplets that were mismatched between each patient and their alloCTL donors, the presumed molecular HLA types of the patient:donor pairs were then entered into the algorithm program and the number of mismatched eplets was quantified for each patient:donor pair. Not surprisingly, the three responding BTP generally received higher cumulative numbers of mismatched eplets (range 42-117) during their course of treatment, compared to the nonresponders (range 20-59), but this likely related to the responding patients receiving more infusions. More interestingly, it was found that certain eplet mismatches were exclusive to the responding BTPs. The 151RV and 62QE were mismatched in at least one treatment for each responding patient (FIG. 1), while no mismatches were found to be exclusive to patients who did not respond. Additionally, it is noteworthy that several other eplet mismatches were associated with the responder group, being present in multiple alloCTL preparations administered to the patients (i.e. 9T, 56R, 166DG, etc). In contrast, there were no mismatched eplets common to the multiple alloCTL preparations administered to nonresponding patients.

The locations of mismatched eplets shown on the α1 and α2 helices of the HLA molecule that are common to the BTPs who responded to treatment are shown in FIGS. 6a-6b. In particular, FIGS. 6a-6b shows diagrammatically the relative location of mismatched eplets from the BTP responder group in Table 6 on the face of the HLA Class I molecule.

Unlike alloantibody (B cell) responses that occur due to three dimensional structure (conformational) nonrecognition, such that the contact of the alloantibody with the HLA molecule might be outside of the space shown in FIGS. 6a-6b, CTL (T cell) responses occur due to nonrecognition of linear short aa sequences that are located at the interface plate between the TCR and the HLA molecule shown.

Interestingly, all of these mismatched eplets were located on the face of the HLA Class I α chains or peptide binding groove that would interact with the T cell receptor (TCR). Some of these mismatched polymorphic residues have been shown to be important for stimulating allogeneic CTL (residue numbers 62 and 166), while another aa (116) located within the peptide binding groove is associated with acute GVHD and a high rate of transplant related mortality following bone marrow transplantation.

The R:S pairs strategically mismatched at polymorphic residues in the HLA Class I:TCR interface may have an affect on the antitumor functionality of alloCTL used for therapy. The significance of the preclinical work in this study is that it can lead to an improved and consistent alloCTL in vitro generation method resulting in potent cytotoxic alloreactive killers. As well, the work can lead to a better personalized allodonor selection for glioma patients in the cellular therapy trial; this would be based upon an analysis of the molecular HLA types of the responding donor lymphocytes relative to that of the patient.

Example 5

Comparison of alloCTL Molecular/Cellular and Functional Characteristics when Generated Using One-Way Mixed Lymphocyte Reaction (MLR) Versus Those Made by One-Way Lymphocyte Dendritic Cell (DC) Reaction (LDCR).

The ability to differentiate human monocytes in vitro into DC using recombinant growth factors is a new opportunity to use DC as stimulators for optimizing the in vitro generation of alloCTL used for the cellular therapy of brain gliomas. Molecular/cellular and functional characteristics of alloCTL currently generated by a standard 1-way MLR technique were compared to those when generated by a technique employing stimulation by 1-way LDCR.

An alternative method of using DC presentation of alloantigen optimizes the generation of potent cytolytic alloreactive killers and induces proinflammatory responses. It is expected that alloCTL generated by LDCR have stronger lytic activity to relevant HLA-bearing targets than those generated by the standard 1-way MLR technique. Activated, mature DC display very high levels of HLA molecules compared to other cell types including lymphoblasts; they are also strong antigen-presenting cells (APC). The exploitation of the high level of surface HLA expression by DC in generating alloCTL results in consistent alloCTL generation with strong lytic alloreactive activity.

Peripheral blood mononuclear cell (PBMC) populations from different individuals as responders and stimulators were used. For one-way MLR, irradiated stimulator lymphoblasts are mixed with responder lymphocytes from normal, healthy HLA-mismatched donors. For one-way LDCR, the monocytes were differentiated into stimulator DC first. Irradiated, activated, and mature DC were mixed with responder lymphocytes from healthy, HLA-mismatched donors to produce alloCTL. The alloCTL generated by each technique was tested for their molecular, cellular and functional characteristics to evaluate their respective alloreactivity.

Figure 5:
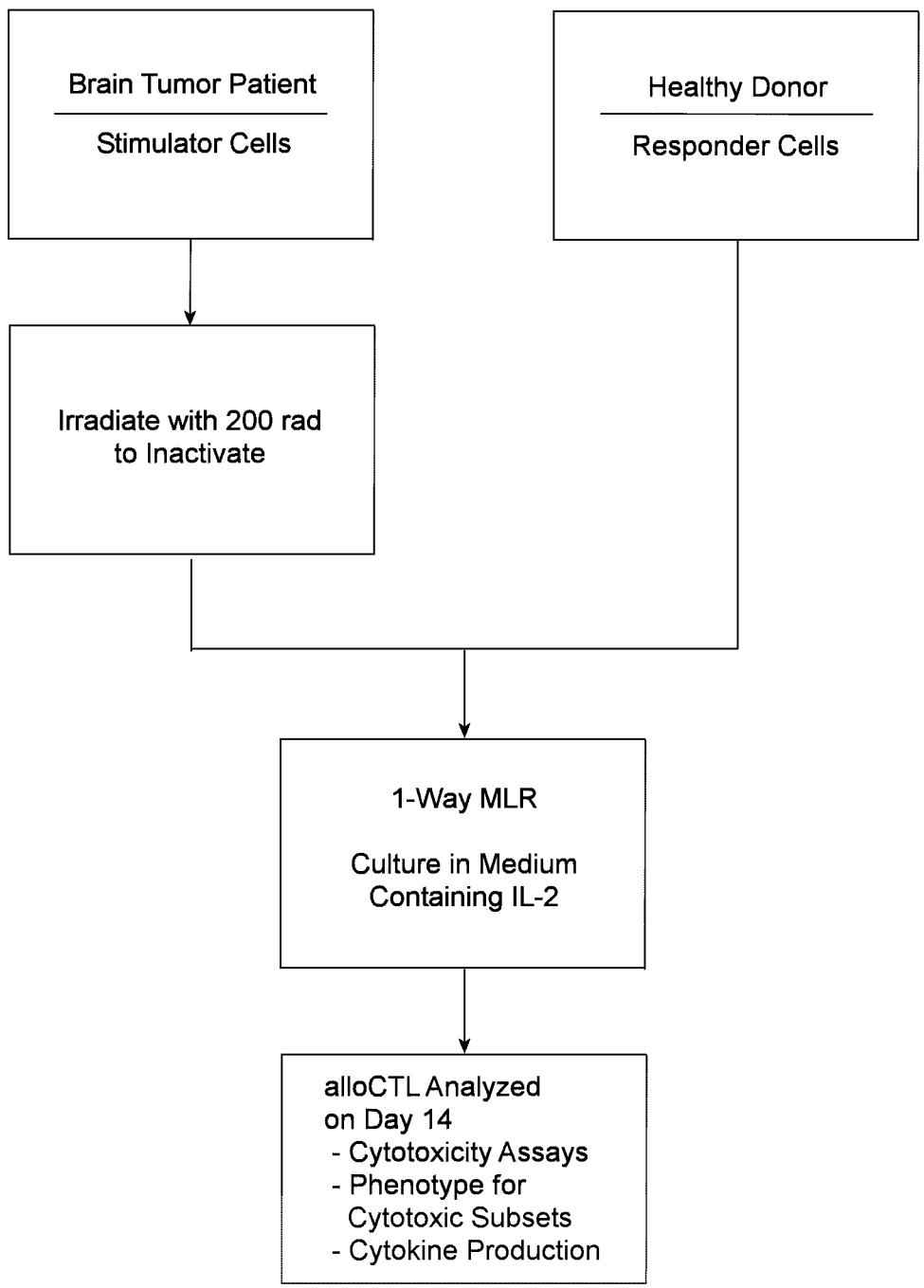
FIG. 5 shows an exemplary method of generating alloCTL when irradiated lymphoblasts isolated from a brain tumor patient are mixed with peripheral blood mononuclear cells (PBMC) isolated from a healthy donor in a one-way mixed lymphocyte reaction (MLR).

In particular, FIG. 5 shows that therapeutic alloCTL are generated when irradiated lymphoblasts isolated from a brain tumor patient are mixed with PBMC isolated from a healthy donor in a one-way MLR. AlloCTL were cultured in medium with low concentration IL-2. Cytolytic function and cytokine production by cells of appropriate phenotype were assayed on day 14 post MLR.

For alloCTL preparations generated from the same responder/stimulator pairs by MLR or by LDCR, the following was performed:

Determination of the cytotoxicity of the alloCTL to relevant target, i.e., stimulator lymphoblasts displaying the HLA to which they are sensitized.

Determination of the fold-increase in the phenotypic subset displaying the activated T cell marker (CD3/CD69) that produces IFN-γ within the alloCTL upon exposure to relevant target, i.e., stimulator patient lymphoblasts displaying the HLA to which they are sensitized.

Determination of the proliferative response of the alloCTL upon exposure to relevant target.

Determination of the soluble Th1 to Th2 cytokine ratios (i.e., IFN-γ to IL-10 or TNFα to IL-4) produced upon alloCTL exposure to relevant target.

Methods for Example 5

Sources of Responder and Stimulator Cells.

To obtain PBMC for preclinical studies, in order to generate PBMC information, the following were performed: (1) normal blood donor collections at 100 ml or less, (2) purchase of buffy coats from the San Diego Blood Bank, and (3) limited leukapheresis of donors. Donors had to test negative for all infectious disease agents. The density gradient isolated PBMC was washed then fractionated, using standard plastic adherence, into monocytes and lymphocytes. The nonadherent cells from the PBMC containing T, B and NK cells was either used fresh or cryopreserved in vials containing 107-108 cells for the MLR generation method. From experience using PBMC as responders, the MLR could be applied equally well to fresh PBMC as well as to vitally-frozen PBMC. For LDCR, the adherent monocytes was differentiated to DC.

Standardizing alloCTL Generated by One-Way MLR or LDCR.

Irradiated stimulator (S) lymphocytes and responder (R) lymphocytes were employed from normal, healthy HLA-mismatched donors. The strategy was to use a small pool of young (18-50 years old) normal blood donors to help standardize the PBMC reactivity to alloantigen. PBMC from older people did not respond to antigenic stimulation as well, i.e., they had quantitative and functional defects in the CD4 T helper cell compartment and cells that lack CD40L. Furthermore, it was demonstrated that resting lymphocytes, activated lymphocytes (aka lymphoblasts), as well as lymphocytes or lymphoblasts that have been cryopreserved and then thawed, all have high HLA surface expression levels, thus could adequately serve as stimulators.

Isolation and Expansion of Stimulator Lymphocytes for Sensitization of alloCTL by MLR.

A 100 ml blood draw yielded 1 2×108 PBMC after isolation from Ficoll density gradients. After washing several times with Hank's balanced salt solution (HBSS), the PBMC was suspended in 20 ml of AIM V synthetic medium containing 5% autologous serum. The cells were injected into the extracapillary space (ECS) of the artificial capillary cartridge and perfused with medium containing Orthoclone OKT3 antibody (50 ng/5×107 cells) and 240 IU/ml of rIL 2. The perfusion volume was doubled every 2 4 days by adding fresh rIL 2 containing medium. Lactic acid concentration was measured daily (7 days/week, YSI Stat lactate/glucose analyzer) to determine the rate of lactate production (usually 0.2 0.25 gm/109 cells/day). Cells were fed every 4 to 5 days or when the concentration of lactate was at 0.5 0.7 gm/liter. Lactic acid production paralleled the expansion rate of the cells.

Multiple vials of stimulator lymphocytes were vitally-frozen so there was the capability of performing multiple alloCTL cultures from any given responder to stimulator (R:S) pairs; minimally 3 cultures were generated from one R:S pair. The number of stimulator PBMC frozen was based upon starting cultures at a R:S ratio of 10:1. Cells harvested from one starter culture were cryopreserved in 10% DMSO/ autologous serum and stored at 80° C. The stimulator lymphocytes were thawed prior to inactivation with gamma-irradiation (127Cs-source, 2000 Rads), then washed before combining with allogeneic responder lymphocytes.

Isolation of Monocytes and Generation of Stimulator DC.

PBMC isolated from whole blood by density gradient centrifugation was washed 2× with Hank's balanced salt solution (HBSS). The PBMC was suspended at a density of 5×106/ml in serum-free, AIM V synthetic medium in plastic tissue culture flasks.

After 30 min incubation at 37° C., the nonadherent cells containing lymphocytes were recovered and cryopreserved; the adherent monocytic cells were washed with HBSS to removed loosely adherent cells then overlaid with fresh AIM-V medium and cultivated overnight at standard conditions. The next day the adherent cells were washed with HBSS to remove residual platelets, then overlaid with AIM-V medium supplemented with 1,000 IU/ml of GM-CSF and 500 IU/ml of rIL-4 and cultivated for 6 days to differentiate monocytes into immature DCs. At day 6, the medium was supplemented with recombinant human TNF-α, IL-6 and IL-1β (10 ng/ml for each cytokine) and cultured an additional 2 days to mature the DCs. Other studies support an estimate that approximately 10% of the starting cell number are obtained as mature DCs. The DCs were subjected to gamma-irradiation (127Cs-source, 2000 Rads), and washed 1× with HBSS in preparation for the LDCR protocol; these represent the stimulator DCs.

Generation of alloCTL by One-Way MLR.

Responder PBMC, from a donor genetically distinct from the donor supplying the stimulator cells, was isolated with Ficoll Hypaque and washed 2× with HBSS. The responder lymphocytes was combined with 127Cs-irradiated stimulator lymphocytes, at a responder to stimulator (R:S) ratio of 10:1 (i.e., one-way MLR). They were placed into the artificial capillary cartridges and cultivated at 37° C. with 5% $CO_2$ with AIM V medium containing 5% autologous serum and 60 International Units (IU)/ml of rIL 2 for 14 days; the cells over a 7 10 day period were weaned from serum containing medium. A restimulation of the alloCTL occurs at day 12 post-MLR with relevant lymphoblasts at a R:S of 10:1 [48]. Cytotoxicity assessments, proliferation, phenotypically-defined cytotoxic subsets and cytokine production were determined on day 14 post-MLR cells as described in later methods.

Generation of alloCTL by One-Way LDCR.

The allodonors used for responders or pCTL were HLA-disparate to the donor supplying stimulator cells. The adherent cells were grown with growth factors that encourage DC (immature) growth. Growth factors were then to be added to the culture medium to mature the DC.

Briefly, the plastic adherent monocytic cells were cultured in serum free AIM-V medium supplemented with 1000 units/ml rhGM-CSF and 500 units/ml rhIL-4 at 37° C. in a humidified, 5% CO2 incubator. Six days later, the immature DC were stimulated with recombinant human TNF-α, IL-6 and IL-1β (10 ng/ml for each cytokine) to induce their maturation for 2 days. DCs were harvested, irradiated and combined with responder PBMC for LDCR at a R:S ratio of 10:1. The DC presented alloantigen (i.e., stimulators) to the T lymphocytes of the allodonor in the presence of low dose IL-2 (60 IU/ml). Reactive responder lymphocytes developed into alloCTL capable of recognizing the HLA on the stimulator cells over a 12 day period. They were restimulated with DC at a 10:1 R:S on day 12 post-LDCR and assessed 2 days later in 4 hour 51Cr-release cytotoxicity assays, for proliferation, and for phenotype and cytokine production.

Example 6

Methods Specific to Example 5A-D

Methods specific to Example 5A

Chromium Release Cytotoxicity Assays.

alloCTL preparations were generated from the same R: S pairs by either MLR or by LDCR. It was determined whether the cytotoxicity of the alloCTL to relevant target, i.e., stimulator lymphoblasts displaying the HLA to which they were sensitized. 51Cr-release assays can be used to determine the lytic activity of alloCTL effector cells when they were co-incubated with the target cells.

Four hr assays were run in 96-well plates at multiple effector to target (E:T) ratios of 3:1, 10:1, 30:1 with triplicate samples as previously described in other publications. Percent specific release was calculated by the formula: [(cpm experimental-cpm spontaneous)/(cpmmaximal-cpmspontaneous)]×100%. Spontaneous release was measured for targets in assay medium alone and maximal release were be produced by lysis of the targets with 2% Triton X-100 (Sigma, St. Louis, Mo.). Lysis obtained at each given E:T ratio was determined and the thresholds of low, moderate and high cytotoxicity can be defined accordingly.

Day 14 alloCTL generated by 1-way MLR and 1-way LDCR were compared. Statistical assessment of lytic activity and the effects of reaction type (MLR vs LDCR), the three E:T ratios evaluated as an ordered factor, the three samples, and their possible interactions were made by 2×3×3 ANOVA with planned post-hoc comparisons. All statistical operations for this and all subsequent methods are accomplished in R, version 2.9 or higher. Optimization of alloCTL by DC presentation was considered possible if the cytotoxic responses, by DC-generated alloCTL compared to 1-way MLR generated alloCTL, against stimulator lymphoblast target cells was >15% higher when all data were grouped and normalized from three equivalent E:T ratios tested.

The alloCTL preparations should have the ability to elicit alloantigen-specific immune responses against relevant target cells in vitro. PHA-stimulated lymphoblasts can be used as target cells, which display high levels of HLA antigen. "Relevant" targets were the lymphoblasts derived from stimulator PBMC. Responding donor lymphoblasts express HLA that should be regarded as "self" and therefore should not be targets of the alloreactive T cells but as a background, negative control. Additionally, K562 natural killer (NK)-sensitive cell targets did not express HLA antigen and could be used as "irrelevant" target cells to assess nonspecific injury caused by NK cells (non-MHC-restricted killing) that was unrelated to T-cell alloreactivity (MHC-restricted killing).

Lysis of K562 was subtracted from stimulator lymphoblast lysis for these comparisons also. The levels of HLA expression by lymphoblasts was analyzed by flow cytometry using the pan HLA-ABC antibody (W6/32) to assess whether the cytotoxicity directly relates to the relative antigen density (MFIs) of HLA on the relevant target cells.

Exemplary Variation.

Figure 6:
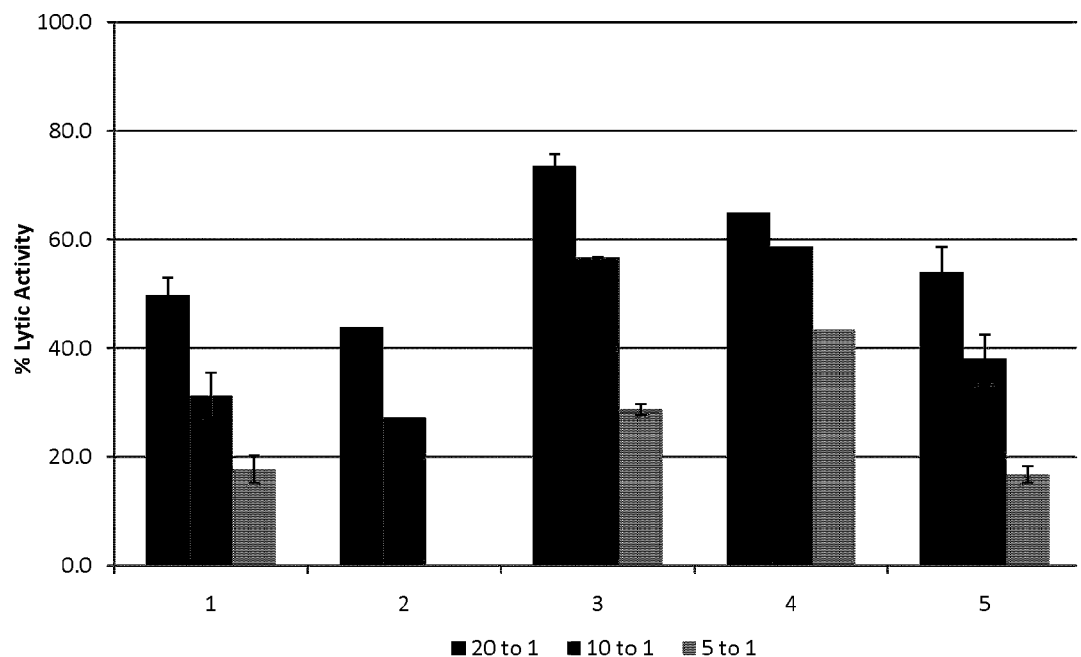
FIG. 6 shows the percentage lysis achieved in 4 hr Chromium-51 (51Cr)-release assays at 3 effector to target (E:T) ratios (left-most columns, 20:1; center columns, 10:1; right-most columns, 5:1). alloCTL was generated following one-way mixed lymphocyte reaction (MLR) using responder cells from five different donors are variably cytotoxic toward target lymphoblasts.

A variation of the above described example is illustrated in FIG. 6, which shows the percentage lysis from 51Cr-release 4 hr assays at 3 E:T ratios (black, 20:1; red, 10:1; blue, 5:1). alloCTL were made with 5 different R:S pairs in MLRs, and the numbers on the abscissa refer to the one-way MLR number. Statistical significance was evaluated using two-way ANOVA and Bonferroni post-tests (*$p<0.05$). These data were representative of two separate experiments performed with triplicate wells.

Methods Specific to Example 5B

Phenotypic Characterization of Activated, Mature Dendritic Cells.

Aliquots of DC were stained with monoclonal antibodies (mAbs) against DC surface markers (anti-HLA class I conjugated to fluorescein isothiocyanate (FITC), anti-HLA class II DR conjugated to PerCp, anti-CD11c conjugated to APC, anti-CD80, anti-CD83, and anti-CD86 conjugated to phycoerythrin (PE) (BD Biosciences/Pharmingen, San Diego, Calif.) on ice for 1 hour. The cells were washed three times with cold PBS before analyzing on an LSR II flow cytometer.

Phenotypic Characterization of Activated, CD3 Cytotoxic T Cell Subsets by Flow Cytometric Analyses.

The cytotoxic subsets with alloCTL preparations were utilized for production of IFN-γ, because this particular cytokine has previously been shown to be most relevant to the Th1 cell-mediated responses to immunotherapy exhibited by T lymphocytes. Additionally, IFN-γ has been used as an in vitro monitoring tool to predict GVH in renal transplant patients where slight mismatches in donor to patient HLA were expected.

With alloCTL preparations generated from the same responder/stimulator pairs by MLR or by LDCR, the fold-increase in the phenotypically-defined CD3/CD8 cytotoxic subset displaying the activated T cell marker (CD69) that produces IFN-γ within the alloCTL upon exposure to relevant target, i.e., stimulator patient lymphoblasts displaying the HLA to which they were sensitized, was determined. The cell subset positive for CD3, CD8, CD69, and intracellular IFN-γ (BD Fast Immune Kit, BD Biosciences) was determined at 24 hr after incubation with or without relevant target cells (stimulator lymphoblasts at a R:S of 10:1). In the last 6 hr of the 24 hr incubation, 10 µg/ml of Brefeldin A, a secretion inhibitor, was added. Nonstimulated or stimulated alloCTL were each aliquoted into three tubes (106 cells/tube) and pelleted at 100×g. Flow cytometric analysis was performed, staining for cell surface markers (e.g., CD3+, CD8+, CD69+) and cytoplasmic IFN-γ cytokine expression. The Fix and Perm reagents e used where indicated according to the manufacturer's protocol. In brief, alloCTL cell pellets were resuspended and incubated with a fluorochrome-conjugated monoclonal antibody (mAb) cocktail on ice for 30 minutes. The cells were washed, fixed and permeabilized, then incubated with a fluorochrome-conjugated mAb specific for IFN-γ for 30 min. Following the second antibody incubation, the cells were washed again and resuspended in PBS and analyzed by flow cytometry. The analyses were performed with a six-color capable BD LSR II flow cytometer. Percentages of the positive activated T cell subset and the mean fluorescence intensities (MFI) of IFN-γ were obtained.

The fold increases in the percentages of the activated subset in the alloCTL that were restimulated versus those not were determined. As well, the fold increases in the MFIs for IFN-γ in the alloCTL subsets that were or were not restimulated were determined. Each of these measures can be useful for prediction of the extent of cytolysis. It was noted that an increase in the cytotoxic subset or the degree of IFN-γ expression that was >1.5-fold may reach significance based upon other's observations with patient PBMC in vaccine trials for glioma. Helping to validate this approach, others showed that data collected by this flow cytometric method compare well to that collected by limiting dilution analyses and supports use of this methodology for subset analysis.

Methods Specific to Example 5C

Determination of the Proliferative Response of the alloCTL Made by MLR or DC Presentation Upon their Exposure to Relevant Stimulator Lymphoblasts.

The CTL precursor frequency within a donor mononuclear cell pool to patient HLA antigens was variable. That may be as high as 10% to allogeneic MHC antigen or as low as 0.1-0.01%. Anticipating that the precursor CTL frequency was identical in any given responder/stimulator pair, it was possible to determine in the experiments here if DC presentation was better than T lymphocyte presentation in an MLR in enhancing the proliferative events of alloresponders. The overall intent was to generate therapeutically significant quantities of alloCTL. The ability of T cells to proliferate when exposed to the antigens that they were sensitized to has been used as an indicator of the presence of antigen-specific CD4+ helper T cells.

The proliferative response of the alloCTL preparations was characterized upon their exposure to relevant patient lymphoblasts displaying the HLA to which they were sensitized. With alloCTL preparations generated from the same R:S pairs made by MLR or by LDCR, the proliferative response of the alloCTL was determined upon their exposure to relevant stimulator lymphoblasts and convert them to stimulation indices for comparison.

The capacity to proliferate in response to HLA presentation by relevant stimulator cells were measured by tritiated thymidine uptake at a R:S ratio of 10:1. In response to the alloCTL seeing relevant antigen, proliferation should ensue. After 48 hr, the culture was pulse-labeled with 3H-thymidine. DNA synthesis, as a measure of proliferation, was quantified by using a liquid scintillation counter to measure the amount of radiolabeled thymidine incorporated into the DNA. A stimulation index (SI) was calculated by dividing the number of cpm for the resensitized alloCTL by the number of cpm for the cells incubated without sensitizing cells.

The SIs obtained for each alloCTL preparation was categorized as having a high proliferative population versus a low proliferative population. The in vitro proliferative capacity of the alloCTL was compared to their cytotoxicity (see Example 5A), phenotypic analyses (Example 5B), and the level of HLA mismatch between the responder and stimulator (Example 7). In general, while there is some consensus in the literature that proliferative events correlate with responder/stimulator MHC disparities at Class II, while cytolytic activity is a function of disparities at Class I, it is possible to confirm the separation of proliferative and cytolytic functions by analyzing the data with molecular HLA types of the responder and stimulator. This was addressed using both conventional and robust regression analyses. In addition to comparing the proliferative differences in alloCTL generated by MLR vs LDCR methods, it was also possible to discern if proliferation of the alloresponder enriched cultures at restimulation resulted from HLA Class II disparities, whereas the functionality of the cells as determined by cell injury, and cytotoxic cell phenotype/cytokine production, related to HLA Class I disparities between responder and stimulators.

Methods Specific to Example 5D

Determination of the Soluble Th1 to Th2 Cytokine Ratios Produced Upon alloCTL Exposure to Relevant Target.

Other researchers have compared IFN-γ/IL-10 ratios as an in vitro monitoring tool for assessing tumor host response using PBMC pre- and post-vaccination, and for T cell induced GVH development and rejection in transplant patients. With alloCTL preparations generated from the same R:S pairs by MLR or by LDCR, it is possible to determine the soluble Th1 to Th2 (i.e., IFN-γ to IL-10 or TNF-α to IL-4) cytokine ratios produced upon alloCTL exposure to relevant stimulator target. It is observed that higher Th1 to Th2 ratios were correlated with induction of a proinflammatory response in vivo and/or correspond to better cytolysis to relevant target.

Supernatants from alloCTL coincubated for 24 hr in the presence or absence of relevant irradiated stimulator lymphoblasts were examined. The cell suspensions were clarified by refrigerated centrifugation at 400×g for 10 min. The clarified medium, or dilutions of it if necessary, were analyzed using the BD cytometric bead array system. The cytokines to be tested include Th1 and Th2 cytokines: IL-2, IL-4, IL-5, IL-10, gamma interferon (γ-IFN) and tumor necrosis factor alpha (TNF-α). The array system allowed for collection of multiple cytokine results from a single small sample at relatively sensitive levels of detection (2.0-4.0 pg/ml). Therefore, the processes not only analyzed IFN-γ/IL-10 ratios but other alternative Th1/Th2 cytokine permutations (i.e., TNF-α/IL-4) as well. For this reason, the array was a cost effective alternative to ELISAs specific for the four cytokines was considered.

Statistical Evaluation.

Statistical analysis was performed by a biostatistician. For statistical analysis in Example 5, the data was described using conventional and statistically robust techniques. Data descriptions include standard 5-point summaries as well as the first four moments and MAD (median absolute deviations). To elucidate the interrelationships of functional alloresponsiveness (i.e., cytotoxicity of the alloCTL, fold-increases in the phenotypic subset displaying the activated T cell marker, proliferation in response to exposure to relevant antigens and/or proinflammatory cytokine production) relative to HLA mismatch, correlative studies included both pairwise analyses with confidence intervals and additional analyses to investigate systematic nonlinearities. Both conventional ANOVA and its robust analogues were used to investigate the relationships. It was possible to compare the mean averages of triplicate samples in three separate experiments using the same R:S pairs of at least 15 alloCTL preparations made by both methods. The number of experiments needed depend upon the pilot data and power analyses. The implication to obtaining significantly higher cytotoxic assessments with alloCTL generated by LDCR vs MLR was an alteration of the generation of alloCTL for clinical studies in the existing IND to the FDA.

Interpretation of Data and Alternative Approaches.

Generally, with alloCTL preparations one might assume that the proliferative events and cytolytic activity correlate with responder/stimulator HLA disparities at Class II and Class I, respectively. This could be reconfirmed using HLA molecularly-typed individuals for HLA-A,B,C and HLA-DR,DQ allelic differences.

At present, alloCTL populations made by MLR for the clinical trial must meet three minimal release criteria before they can be administered. First, the gross phenotypes of all alloCTL populations must show that the preparations were >60% CD3+. Second, the viabilities of the cultures, determined by trypan blue dye exclusion counts on a hemocytometer, must be >60%. Third, the minimum cytotoxicity they must exhibit to patient lymphoblasts is 30% lysis at a 30:1 effector to target ratio (E:T). It was expected that alloCTL made by LDCR would consistently meet those minimum requirements. If the presently proposed LDCR were inadequate, it was quite possible that the activation state of the DCs could dramatically influence alloCTL generation and function. It was possible to explore agents such as ssRNA, dsRNA, LPS, imiquiod, or other toll-like receptor (TLR) agonists that would affect the TLR expressivity by the DC and then measure alloreactivity by the alloCTL preparations.

A 51Cr-release cytotoxicity assays can be substituted with the 7-amino actinomycin D (7AAD) flow cytometric based cytotoxicity assay as a nonradioactive, rapid alternative, albeit the latter was a cell hungry technique. For proliferation, a nonradioactive alternative to tritiated thymidine was the BrdU Flow Kit (BD Biosciences). That kit could provide BrdU and 7-AAD staining along with surface phenotype, such as CD3, to permit the enumeration and characterization of cells that were actively synthesizing DNA (BrdU incorporation) in terms of their cell cycle position (i.e., G0/1, S, or G2/M phases as defined by 7-AAD staining intensities).

Example 7

The Algorithm Evaluates and Predicts Suitable HLA Partial Mismatches Between Alloresponder and Stimulator Lymphocyte Pairs that Will Induce the Generation of Potent Cytotoxic Alloreactive Killers It was determined whether the extent or type of HLA eplet mismatch between responder and stimulator lymphocytes correlated with (1) the in vitro ability of the responding donor alloCTL to lyse stimulator lymphoblasts; or upon alloCTL exposure to relevant target cells, would (2) cause increases in the appearance of cytotoxic subsets producing proinflammatory IFN-γ cytokine, or (3) cause a skew to higher Th1 to Th2 secreted cytokine ratios. It was noted that nonpermissive HLA mismatch between the responder and stimulator (either number and/or specific type of immunogenic eplets) as recognized by the HLAMatchmaker (HLAMm) algorithm modified for cellular response were predictive of functional alloreactivity.

HLAMm is an algorithm configured to provide structurally based HLA matching. In particular, when HLAMm is applied to the diverse HLA repertoire, it is able to reliably predict B cell driven alloantibody generation following organ transplantation. HLAMm operates by finding permissible mismatch between molecularly HLA-type donors and recipients such to minimize rejection.

Two phases were employed for this work. Example 7A involves a "Discovery" phase where in vitro functional assessments (i.e., cytolysis of relevant target, appearance of phenotypic cytotoxic subsets or proinflammatory cytokine induction to target exposure) were used to drive the modification of the cellular version of the HLAMm program. Versions of the HLAMm computer program can determine quantitative estimates of structural compatibility and identification of specific eplets or other amino acid configurations (some that are already associated with T cell induced GVH disease) that might have relevance here, since theoretically a strong alloresponse is desired. Example 7B involved a "Validation" phase where matched glioma patient lymphocytes and glial tumor specimens were available as stimulator cells and relevant tumor targets, respectively, along with prospectively chosen allodonors from a pool of HLA-typed individuals that HLAMm would categorize as robust or nonrobust allodonors. The modified HLAMm program was validated for successful in vitro prediction of alloCTL functional alloreactivity.

A training set using molecularly HLA-typed responder and stimulator lymphocytes for the HLA Matchmaker (HLAMm) cellular program was created. It was also determined whether the extent or type of HLA eplet mismatch between the stimulator cells and the responder donor PBMC was indicative of the in vitro ability of the donor alloCTL to lyse stimulator lymphoblasts, or upon exposure to relevant HLA target antigen, to significantly increase the activated T cell subset (CD3+/CD8+/CD69+) producing the proinflammatory cytokine, IFN-γ, or to skew the secreted cytokines to a higher Th1/Th2 ratio (i.e., IFN-γ:IL-10 or TNF-α/IL-4).

HLAMm, used in the transplantation setting to predict alloantibody responses, is based upon analysis of mismatched epitopes defined by so-called eplets that are configurations of polymorphic amino acid residues within a 3-Angstrom radius. The computer program applies different algorithms to consider the two major causes of HLA mismatch-induced bone marrow (BM) transplant patient mortality: engraftment failure and graft-versus host (GVH) disease. HLA mismatch-induced engraftment failures occur during the early post-transplant period and appear to involve antibody-mediated mechanisms, whereas HLA mismatch-induced GVH disease is primarily induced by alloreactive T cells, which interact through their T cell receptors (TCR) with alloepitopes on mismatched HLA molecules. The current algorithm has accurately predicted alloantibody responses in transplant patients according to the number of structurally defined mismatched epitopes of the donor, and it does not as reliably predict the T cell induced GVH disease.

Structurally-based HLA matching at the amino acid level by HLAMm for hematopoietic stem cell transplantation was inaccurately hypothesized to benefit transplant patient survival. Permissible matching at the amino acid level had only a modest effect on engraftment and acute GVH disease, and it did not benefit patient survival. Interestingly, structural mismatching at the intermediate level seemed to convey the highest risk for acute GVH disease; this finding was consistent with CTL precursor data reported by the Leiden transplant group. Other algorithms were structurally based and include the polymorphism of the peptide-binding groove and the structural aspects of the T cell receptor (TCR)-HLA contact area. Obviously, where permissive mismatches were required for transplant patients, nonpermissive mismatches were identified that would lead to good cytotoxic allokillers. Understanding of the structural and functional basis of T cell alloreactivity was useful to ultimately enable choosing donors that provide functionally robust alloCTL based on HLA eplet mismatch between patient and donor. HLAMm findings using best-fit serologic HLA data from earlier pilot clinical trial with alloCTL indicated that the three responders, but none of the non-responders, had mismatches at two eplets, 151RV and 62QE.

The degree of cytotoxicity to stimulator lymphoblast target cells by each alloCTL preparation made from HLA-typed R:S pairs was assessed. It was noted that the alloCTL preparations with higher percentages of lysis to relevant target correlate with specific HLA mismatch eplets. Fold increases in each alloCTL preparation were assessed for the activated T cell subset with IFN-γ expression upon exposure to relevant stimulator lymphoblasts. It was noted that alloCTL preparations with significant fold increases (i.e., >1.5-fold) in the activated cytotoxic T cell subset producing IFN-γ upon exposure to relevant target correlate with specific HLA mismatch eplets. Production of Th1 and Th2 cytokines was determined by BD Cytometric Array and ratios of IFN-γ/IL-10 and TNF-γ/IL-4 in the supernates of alloCTL coincubated with irradiated stimulator lymphoblasts were assessed. It was noted that secreted Th1/Th2 ratios that were >1:1 (proinflammatory) correlate with specific HLA mismatch eplets between responder and stimulator pairs.

Methods for Example 7

AlloCTL Generation and Determination of Alloresponsive Functionality.

Either of the methods in Example 5 can be used for alloCTL preparation in this example. Cytotoxicity assays, phenotypic analyses, and cytokine determinations and their statistical evaluations were as described in Example 5.

Cytotoxicity of Relevant Target.

Relationships were drawn between the degree/type of HLA mismatch (structural) of responder/stimulator pairs and the alloresponsive characteristics (functional) of each alloCTL preparation. In particular, lysis of target lymphoblasts by the alloCTL in 4 hr assays (triplicate samples at effector:target ratios of 3:1, 10:1, and 30:1) was evaluated and normalized. Normalized cell lysis by the alloCTL of stimulator lymphoblasts are categorized as low (e.g., achieving between 0-33% cell injury), moderate (say, between 34-65% cell injury), or high (>66% cell injury). Both conventional regression modeling with the general linear model and its robust analogues were used to assess the HLA mismatch and alloresponsive characteristics across effector:target ratios. In vitro cytotoxicity data is correlated with the HLA mismatch structural evaluations.

Appearance of Cytotoxic T Cell Subsets Producing Proinflammatory Cytokine Upon Exposure to Relevant Targets.

The phenotypic analysis of the alloCTL preparations by flow cytometry using the BD Fast Immune Kit allowed a determination of the CD3+/CD8+/CD69+/IFN–γ+fold increases achieved upon restimulation of the alloCTL with irradiated stimulator lymphoblasts. The fold increases is specifically related to mismatched HLA-eplets (number and type). For purposes of multi-factorial analysis, fold increases of the cytotoxic T cell subset producing proinflammatory cytokine were analyzed by categorizing each alloCTL preparation into one of three cytotoxic T cell categories. Although subject to modification once the data were collected, definitions for categories were used as follows: (1) low as <1-fold increase in CD3+/CD8+/CD69+/IFNγ+, (2) intermediate as >1 but <1.5-fold CD3+/CD8+/CD69+/IFNγ+, and (3) high as >1.5 CD3+/CD8+/CD69+/IFNγ+. Because the alloCTL were labeled with CFSE before incubation with stimulator lymphoblasts, it was possible to distinguish between R and S cells. Additionally, since it was possible to analyze the T cell subset that was CD3+/CD8+, the T-helper cell CD4+ phenotype was analyzed by default as cells that were CD3+/CD8−. Three CD4+ helper/inducer T-cell categories were similarly defined as low, intermediate, and high. The fold increases obtained in the activated T cell subsets within alloCTL preparations, and the CD4:CD8 ratios that were also CD69+, were correlated with HLA mismatches and analyzed by polytomous logistic regression analyses.

Production of Th1/Th2 Cytokines Upon Exposure to Relevant Targets.

Supernates from alloCTL coincubated for 24 hr in the presence of irradiated stimulator lymphoblasts were examined for cytokine secretion as described earlier. The Th1 and Th2 cytokines assessed by BD cytometric bead array included IL-2, IL-4, IL-5, IL-10, IFN-γ and TNF-α using clarified medium (100 µl aliquots). While ratios of four cytokines (IFN-γ, IL-10, TNF-α, IL-4) can be measured using sandwich ELISA kits at levels of detection of 2.0-4.0 pg/ml, the array system was a cost effective, time-saving alternative. Again, subject to modification based upon the data collected, ratios of Th1:Th2 cytokines >2.0 were used that were considered to be highly proinflammatory, ratios <2.0 but >1.0 was proinflammatory, and ratios <1.0 were anti-inflammatory. Other permutations of the Th1 to Th2 cytokines were assessed, such as IL-12/IL-10, or additive Th1 and Th2 cytokine ratios (i.e., IFN-γ+TNF-α/IL-10+IL-4) were analyzed if dichotomous results were obtained. IL-2 was disregarded as it was a component of the medium in which the alloCTL was maintained and thus likely to be at a concentration in a non-linear range. These analyses were chosen as ratios of the Th1- to Th2-type cytokine producing cells (i.e., IFNγ/IL-10 ratios) because they were informative before in predicting rejection, a T-cell driven response in transplant patients, and as a response in immunotherapy treated (vaccinated) patients.

HLA Typing.

The responders and stimulators were HLA typed by high resolution molecular DNA methods for class I HLA-A,B,C and class II HLA-DR,DP,DQ using RT-PCR sequence specific primers (SSP) or by sequence based typing (SBT). Serological typing may also accompany these analyses. As in Example 5, lymphocytes from young, normal donors were used.

Serum screening methods for HLA antigens include complement-dependent lymphocytotoxicity (CDC) determined by direct testing, such as the NIH standard and Amos modified tests, and anti-human globulin augmentation (AHG) technique and in antigen-binding assays such as flow cytometry, ELISA, and Luminex.

It should be noted that high and intermediate resolution methods may be employed. In general, a "high resolution method" is defined as any method that results in specific sequence data, while an "intermediate resolution method" is defined as a method that provides at least partial sequence data. Examples of high and intermediate resolution methods include sequence based typing (SBT), sequence specific primer (SSP), restriction fragment length polymorphism (RFLP), or sequence specific oligonucleotide (SSO) methods.

Such high or intermediate resolution methods also include molecular DNA sequencing methods, molecular RNA sequencing methods, and molecular protein sequencing methods and may be employed to determine patient cell information and/or donor cell antigen information.

HLAMatchmaker (HLAMm) Algorithm.

The class I and class II HLAMatchmaker programs used for transplant rejection predictions are posted at the website: http://www.hlamatchmaker.net/. Here it was tested whether the extent/type of HLA mismatch at the epitope level between the stimulator (i.e., clinical translation=brain tumor patient) and the responder (i.e., clinical translation=alloCTL donor) was predictive of the functional properties of the alloCTL. The number and type of mismatched eplets (for functional epitopes) were analyzed between responder and stimulator at HLA class I and class II alleles by HLAMm. It was determined whether a significant relationship existed between the in vitro-collected functional data sets and the ability of the cytotoxic variant of the HLAMatchmaker program to predict the robustness of the functional response. The program's parameters can be modified to be reflective of the in vitro data involving cytolysis and Th1 responses.

Initially, a data set was collected (e.g., as in Example 7A) and utilized as a training set for the algorithm. Validation of the HLAMm algorithm occurs in Example 7B. The resulting HLAMm algorithm provides a useful tool in clinical studies if it allows a prediction of functionally active allCTL and selection of appropriately mismatched donors for brain tumor patients based on molecular HLA types.

Characterization of Structural Mismatches.

Direct alloreactivity was seen when T cells restricted to one HLA molecule were exposed to APC bearing a different, but related HLA molecule. Many of the contacts involved in TCR antigen recognition involve binding of TCR elements to the HLA antigen-presenting face, and because of allelic structural differences, the binding of the stimulator alloHLA to a TCR on a responder may be with greater affinity than to cognate self-HLA. As well, aa substitutions in the antigen binding groove of HLA could contribute to alloreactivity. Therefore, it was possible to focus on two aspects: (1) those HLA residues on the TCR "docking" face which were exposed and capable of taking part in direct TCR binding, and (2) those HLA residues lining the HLA antigen-binding groove, which are capable of participating in antigen binding. Since the enhanced affinity of the TCR for alloHLA+peptide may result from (a) changes in TCR/HLA interactions, (b) changes in TCR/peptide interactions, or (c) a combination of these, comparator algorithms were developed to look at these two classes of allelic changes first separately, then in combination, seeking predictive correlations between structural differences and allostimulation potential. A "mismatch scoring" procedure was developed for related HLA alleles that was predictive of alloresponses associated with the mismatch.

Two conditions were used to evaluate structural based matching to cellular immune alloresponsive functionality (see Table 7). First, three general mismatch levels involving direct contact between HLA and TCR were considered. Group 1 related to structurally identical or very similar mismatch between alleles of responder and stimulator that might have low alloresponsive functionality. Group 2 related to mismatches with an "intermediate" level of structural mismatching would cause more cytolysis of relevant target cells or increase the cytotoxic subset upon restimulation. Group 3 related to structurally very dissimilar mismatches would have less responsiveness than Group 2 because the self-restricted T-cell repertoire would have a lower alloreactive potential for such mismatches. The multivariate analysis suggested a correlation between grades II to IV acute GVH disease and increasing low numbers of triplet/patch mismatches (from 0 to 4), but the 5+ triplet/patch mismatches had actually a lower incidence of GVH disease. Moreover, another transplant group reported lower cytotoxic T cell precursor frequencies towards more structurally divergent mismatches. Second, the polymorphisms of the peptide-binding groove were considered because they affect the HLA bound peptide repertoire recognized by T cells. Mismatched alleles with differences in groove residues will bind different repertoires of peptides including the minor histocompatibility antigens and these variations depend on the number of residue substitutions and key residues in the binding pockets. While the binding pocket polymorphisms could be described with patches similar to eplets, previously reported concepts about binding patterns such as the supertypes described by Sidney et al. BMC Immunology 9 (2008) 1 and by Doytchinova et al J Immunol 172 (2004) 4314-23 were applied.

TABLE 7

Predicted Alloresponse Based Upon HLA Allele Mismatch of R and S

| Combination | R:S Mismatch - Allele 1 | R:S Mismatch - Allele 2 | Net Predicted Alloreactive Response |
| --- | --- | --- | --- |
| 1 | Low | Low | Very Low |
| 2 | Low | Intermediate | High |
| 3 | Low | High | Low |
| 4 | Intermediate | Intermediate | Very High |
| 5 | Intermediate | High | High |
| 6 | High | High | Low to Very Low |

For each responder/stimulator allele mismatch, the two corresponding HLA structures were compared. A "mismatch scoring" algorithm was developed to quantify the structural mismatch between pairs as low, intermediate and high. Recalling that alloreactivity was the result of T cells encountering a foreign HLA molecule(s) that was sufficiently similar to self to allow TCR/HLA interactions, yet sufficiently different to trigger the activation of a subset of those cells, it was noted that intermediate level mismatching may result in the strongest alloreactive response. Assuming that to be the case, and further assuming additive alloresponses across two mismatched alleles, Table 8 shows predicted net alloreactive responses from different HLA mismatch combinations.

A characterization of structural mismatch with the alloreactive response between stimulator and allo-responder involves the number/type of eplets, with binding avidity to the docking interface of the TCR/HLA, or to polymorphic patches in the peptide binding groove. It was possible to observe and record other eplets with amino acid configurations that were associated with functional alloresponsiveness. Functional assessments includes the alloCTL preparation's cytotoxicity to HLA-relevant target cells, or upon alloCTL exposure to relevant stimulator targets, the appearance of a higher percentage of cells displaying the cytotoxic phenotype that was producing IFN-γ, and a skew to proinflammatory cytokine secretions. Three sets of in vitro data (cytotoxicity, cytotoxic phenotype, cytokine secretion) were analyzed relative to the various HLA structural mismatch approaches. The combined information was analyzed with conventional and robust multivariate regression analyses to determine systematic underlying relationships across approaches.

The multifaceted approach that was taken incorporates current concepts for the in vitro collected information. In addition to HLAMm, other investigators have used serologic crossreactive group (CREG) typing, or structural approaches such as Histocheck that applies the so-called distance index of Risler to assess functional similarities between aa substitutions on disparate HLA molecules, or other counting of aa according to physiochemical properties, but these efforts have largely been unsuccessful in the transplantation field. Other issues considered included alloreactive-enriched preparations that could also contain natural killer (NK) cells. Although the alloCTL preparations were enriched for allokillers, the NK cell impact on the cytotoxicity obtained was considered; data collected using non-MHC expressing, NK-sensitive K562 target cells in the cytotoxicity assays; and that effect subtracted. The structural matching approach included polymorphisms in the 77-82 sequence positions that could be considered as sites for NK cell inhibition or activation along with the associated KIR polymorphisms.

The structural basis of indirect allorecognition raised the possibility of a single allele mismatch generating immunogenic allopeptides that could be presented by the matched alleles of the HLA phenotype. Several investigators have developed computer algorithms that predict for any protein, the most likely nonamer peptides that could bind to a given class I allele (http://www.imtech.res.in/raghava/mmbpred/algorithm.html). This program could be readily used for mismatched alleles.

The HLAMm was modified to predict functional in vitro cytolytic and Th1 responses to glioma target cells by alloCTL made with particular responder:stimulator pairs. With matched patient glioma and lymphocytes, it was possible to determine the cytotoxicity to patient glioma when patient HLA-expressing lymphoblasts were used for stimulation of the alloCTL. This developed a tool that allowed selection of allodonors of specific molecular HLA types that predicted robust/nonrobust alloCTL cytolytic or proinflammatory response to the relevant tumor target cells.

The ability of the modified HLAMm algorithm to prospectively predict functional in vitro cytolytic and Th1 responses to glioma target cells by alloCTL made with particular responder:stimulator pairs was tested. It was noted that slighter degrees of HLA mismatch (number and/or type of eplets) between donors and patient, as recognized by the modified HLAMatchmaker algorithm, would result in more cytolytic allokillers than those HLA mismatches that were totally disparate. Alternatively, it was possible to find that the extent of overall eplet mismatch was not as important as certain types of mismatches that might consistently appear in multiple donor mismatches. The information gathered was useful as a screening method for choosing donors whose PBMC will consistently generate robust alloresponses to the patient's HLA antigens present on the glial tumor but not on normal brain glia. The clinical extrapolation was that molecular HLA analyses between allodonors to the glioma patient were predictive of either acute toxicity and/or response to treatment in patients treated with intratumoral alloCTL.

Methods in Example 7B

Matching criteria established during research were applied to a separate cohort of data coming from matched glioma patient lymphocyte and tumor specimens in a tumor bank. The modified HLAMm program was used to predict stimulator:responder pairs that would result in robust alloCTL functionality. Cytotoxicity, phenotype, and cytokine response following co-incubation with target cells were measured as above in Example 7A.

Validation Using Patient Tumor/Lymphocyte Sets as Targets and Stimulator of alloCTL.

A tissue bank contains matched patient lymphocyte and glioma specimens. Tissue in the bank was collected using an IRB-approved protocol, under which patient confidentiality was maintained. The patient lymphocytes acted as stimulators of alloCTL. The cultured glioma specimens acted as relevant targets in cytotoxicity assays. It was documented that tumor cells in situ and in culture express MHC class I antigens.

It was possible to use precursor alloCTL from a pool of molecularly-HLA typed, young 18-50 year old allodonors to maximize the likelihood of a vigorous response. The specificity, effector function, and avidity of alloCTL were predicted by the modified HLAMm program, based on the HLA type of the alloCTL precursor (responder) and stimulator cells. Stimulator:responder pairs could be chosen that the program would predict to be robust or nonrobust based upon molecular differences in HLA type. For this, it was possible to obtain PBMC from glioma patients and close relatives expected to have little HLA variability, and as well, PBMC from unrelated donors of different race/ethnicity expected to have large HLA variability.

The validation phase was performed with several patients matched tumor:lymphocyte sets (i.e., tumor targets:stimulator lymphocytes) and several allodonors as responders for each of the tumor:lymphocyte sets. The ability of HLAMm to predict function was assessed, especially cytotoxicity using multiple alloCTL preparations from the various allodonors. The validation models employed both conventional and robust linear regression and analysis of variance and covariance models for continuous data.

When choosing extensively mismatched donor PBMC this will generate nonrobust alloCTL responses, whereas minimizing the extent of HLA mismatch might generate the most efficacious alloCTL responses, i.e., minor HLA mismatch may better signal aberrant self and induce a better allo reaction than total mismatch. If it was found that no correlation exists between the extent of HLA mismatch and the degree of alloCTL responsiveness, these data would suggest that other factors might be playing a critical role in the generation of cytotoxic alloCTL. Other parameters to consider induce evaluating apoptosis induction relative to lysis by 7AAD assays instead of Chromium release cytotoxicity assays. There was evidence that effector CTL caused direct cell injury upon contact with glioma cells by perforin/granzyme-mediated lysis and by induction of tumor cell apoptosis. It was also possible that finding other combinations of Th1/Th2 cytokine secretions relative to HLA differentials to feed into the HLAMm algorithm also was better predictive.

It was noted that patient treatment by intratumoral adoptive transfer of alloCTL may include not only the effects of adoptively transferred, ex vivo activated alloCTL, a passive immunotherapy component, but in addition, an active immunotherapy component as well. Microglia and other APCs could engulf apoptotic glioma cells, which were then capable of presenting endogenous tumor-associated antigens to circulating T lymphocytes. This process of cross-presentation has the overall effect of increasing the patient's CTL precursor frequency and function against TAA. Similar to what has been previously observed in tumor vaccination protocols, it was expected that increases in endogenous tumor-specific anti-glioma CTL activity following adoptive transfer of alloCTL. If observed, these increases would suggest that the endogenous immune system (active immune therapy) played a role in a cellular (passive therapy) approach.

This was easily tested by using both patient tumor and patient lymphoblasts as targets. After accruing patients to a dose escalation clinical study involving repeated intratumoral placements of alloCTL in recurrent glioma patients, it was then determined whether HLAMm prediction of the number and type of mismatched HLA-eplets could also be related to the acute toxicity the patient may experience after infusion with a particular alloCTL infusate. In addition, that same information gathered over the entire treatment period for any patient's alloCTL repertoire could be related to patients segregated into responder/nonresponder groups.

An increase was expected in the frequency of host CD8+ "cytotoxic" T cells following alloCTL immunotherapy, presumably responding to TAAs on the host glioma cells damaged by adoptively transferred alloCTL, after multiple cycles of treatment. However, it was possible that the CTLp frequency to tumor antigen would be very low in glioma patients. After first subtracting "self with no TAA" values from "self with TAA" values, the differences between pre- and post-treatment CD8+ cytotoxic T-cell activity could be assessed. This was useful insight as to the HLA differences required of donors to yield cytotoxic alloreactive killers. This information enhanced the response rate to brain tumor adoptive cellular immunotherapy with alloCTL.

Example 8

Molecular HLA Class I Types and Eplet Mismatches in Five Responder:Stimulator Pairs Data was gathered to develop the algorithm that evaluates the molecular HLA types of a brain tumor patient against that of a pool of healthy allodonors. These data provide additional insight to reliably predict which allodonors will provide responder cells for consistent generation of alloCTL with robust proinflammatory cytokine production and cytolytic effector functions. Six PBMC donors were molecularly HLA-typed by RT-PCR SSP (see Table 8).

The PBMCs from one donor were used as stimulator cells and the PBMCs from five different donors were used as responder cells in five separate one-way MLRs to generate alloCTL. The alloCTL preparations were evaluated for their cytotoxicity toward relevant stimulator lymphoblast targets. MLRs 3 & 4 were notably superior to MLRs 1, 2 & 5 (significance $p<0.05$, see FIG. 7). It was also confirmed that the lysis of target cells was significantly reduced when anti-HLA was titrated into the assay, confirming that alloreactive HLA-restricted CTL were present. To determine if cytotoxicity correlated with differences in HLA Class 1 molecular structure between the R:S pairs that were used to generate alloCTL, the HLAMm program was used to evaluate eplet mismatches (see Table 8).

Figure 9A:
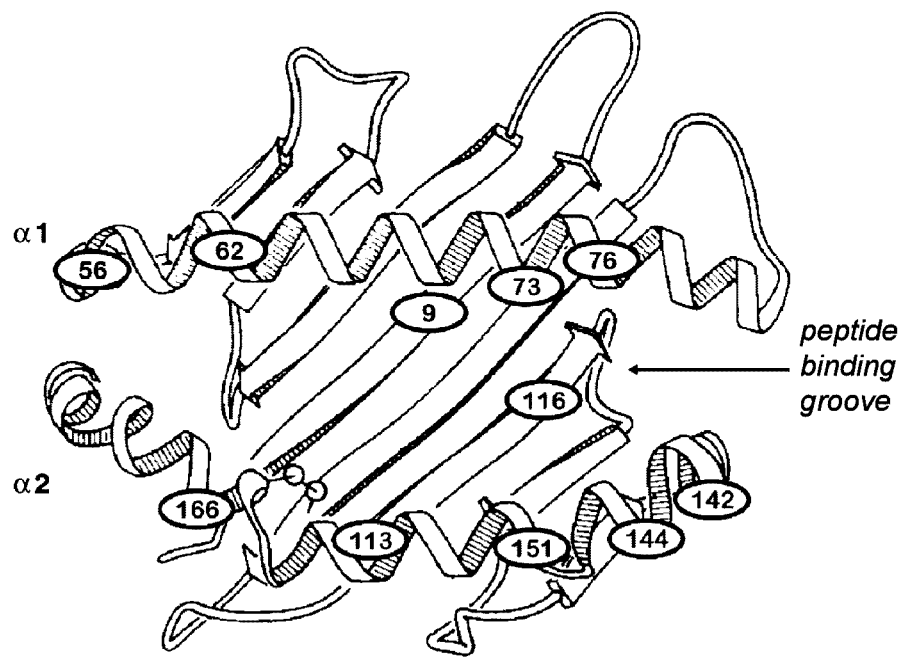
FIGS. 9A-9B shows diagrammatically the relative location of mismatched eplets from the brain tumor patients (BTP) responder group of Table 5 on the face of the HLA Class I molecule and in the peptide binding groove.
Figure 9B:
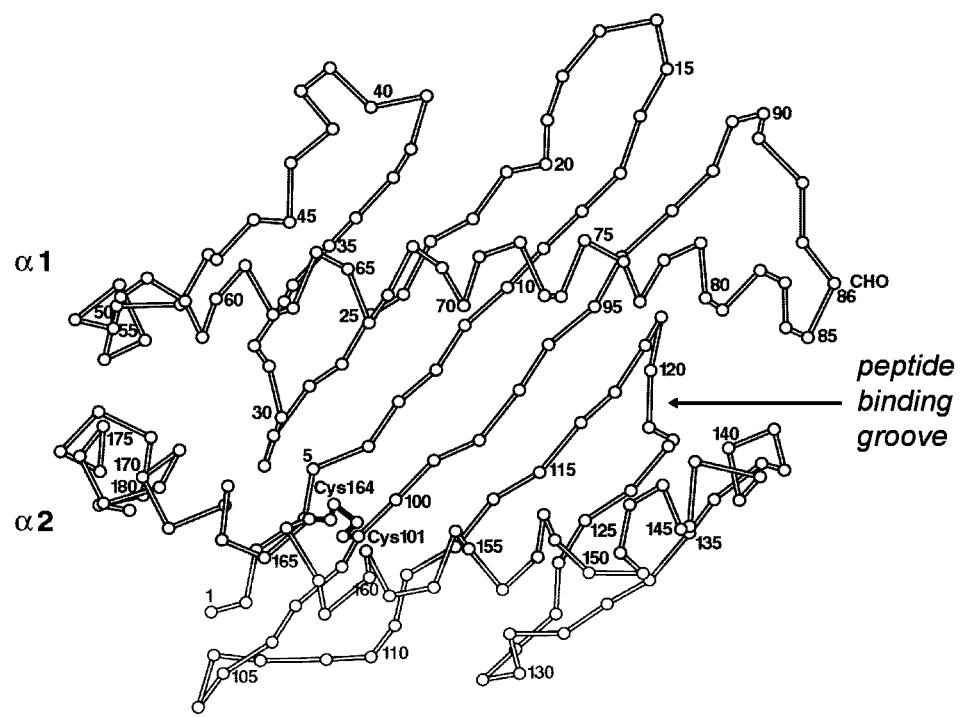

Interestingly, alloCTL generated in MLR 3 had the greatest number of mismatched eplets, corresponding to the largest number of mismatched polymorphic residues, between the R and S. Residues of the HLA Class I molecule that have been shown by others to be important for stimulation of allogeneic CTL were printed in lighter color. The total number of mismatched polymorphic residues on the HLA Class I molecules between R:S pairs was a potential contributing factor to the cytotoxic effects of alloCTL generated following one-way MLR. In addition, the type of mismatch may also be important. Of particular interest were aa sequence differences at locations on the α1 and α2 helices of the HLA molecule, such as those pointed out earlier on the class I molecule (see FIGS. 9a-b): aa 56, 62, 65, 69, 72/73, 76, 142, 144, 151/152, 154/155, 162/163. Specific aa on the class II molecule: aa 11, 35, 69, 76, 84-87, 55, 67, 70 is also of interest.

In addition, mismatched alleles with differences in groove residues bind different repertoires of peptides including the minor histocompatibility antigens, and these variations depend on the number of residue substitutions and key residues in the binding pockets. As shown for class I (see FIGS. 9a & b): aa 9, 97, 113/114, and 116 were locations of particular interest, and for class II: aa 8, 9, and 71.

TABLE 8

| Molecular HLA type of Stimulator | Responder/ one-way MLR Number | Molecular HLA type of Responder | Number of Mismatched eplets at each HLA Class I locus | Cumulative number of mismatched eplets | Mismatched eplets |
|---|---|---|---|---|---|
| A*2407 | 1 | A*2407 | 0 | 9 | — |
| A*2407 |   | A*3401 | 0 |   | — |
| B*0705 |   | B*1535 | 5 |   | 65QIA, 70 AQA, 163E, 177DT, 180E |
| B*4002 |   | B*3802 | 4 |   | 9H, 41T, 44RKE, 163E |
| Cw*0702 |   | Cw*0702 | 0 |   | — |
| Cw*0702 |   | Cw*0702 | 0 |   | — |
|   | 2 | A*0201 | 8 | 37 | 62EE, 65GKA, 73TN, 76ERI, 82ALR, 142MI, 144TKR, 166DG |
|   |   | A*6801 | 8 |   | 62EE, 65GKA, 73TN, 76ERI, 82ALR, 142MI, 144TKR, 166DG |
|   |   | B*3512 | 5 |   | 44REE, 65QIA, 70AQA, 177DT, 180E |
|   |   | B*4427 | 0 |   | — |
|   |   | Cw*0401 | 8 |   | 9D, 147L, 253Q, 73AS, 113YD, 116S, 151RA, 193PL |
|   |   | Cw*0801 | 8 |   | 9D, 147L, 253Q, 73AS, 113YD, 116S, 151RA, 193PL |
|   | 3 | A*0201 | 4 | 41 | 62EE, 65GKA, 76ERI, 166DG |
|   |   | A*1101 | 4 |   | 62EE, 65GKA, 76ERI, 166DG |
|   |   | B*4402 | 9 |   | 44REE, 62RN, 65QIA, 70AQA, 76ERN, 113HN, 163E, 177DT, 180E |
|   |   | B*4427 | 4 |   | 9H, 76ERN, 113HN, 163E |
|   |   | Cw*0304 | 8 |   | 9D, 11AVR, 147L, 253Q, 73AS, 116S, 151RA, 193PL |
|   |   | Cw*0401 | 8 |   | 9D, 11AVR, 147L, 253Q, 73AS, 116S, 151RA, 193PL |
|   | 4 | A*0201 | 1 | 26 | 70AQS |
|   |   | A*2402 | 1 |   | 70AQS |
|   |   | B*1501 | 6 |   | 44REE, 65QIA, 70AQA, 163E, 177DT, 180E |
|   |   | B*3502 | 4 |   | 9H, 41T, 44RKE, 163E |
|   |   | Cw*0303 | 7 |   | 9D, 11AVR, 147L, 253Q, 73AS, 151RA, 193PL |
|   |   | Cw*0401 | 7 |   | 9D, 11AVR, 147L, 253Q, 73AS, 151RA, 193PL |
|   | 5 | A*2402 | 0 | 10 | — |
|   |   | A*2902 | 0 |   | — |
|   |   | B*4001 | 4 |   | 44RE, 62RN, 65QIA, 70AQA |
|   |   | B*4501 | 0 |   | — |
|   |   | Cw*1203 | 3 |   | 253Q, 151RA, 193PL |
|   |   | Cw*0602 | 3 |   | 253Q, 151RA, 193PL |

Example 9

In Vitro Studies with Human Cells and Functionality Testing of alloCTL Preparations HLA can act as tumor directed antigen and blood lymphocytes may be used to sensitize CTL. It has been demonstrated through tests that HLA is absent on normal brain cells (i.e., neurons, oligodendrocytes, and astrocytes), but is present on brain tumor cells.

Low-passage glioma cell explants and single cell suspensions of fresh normal brain cells (tissue derived from seizure patients undergoing lobectomy) were examined by flow cytometry to assess their MHC Class I and II expression. Brain tumor cell explants expressed high levels of HLA Class I antigens, and little to no Class II, whereas normal brain did not express, or expressed little, Class I and II antigens, suggesting that patient HLA could act as brain tumor directed antigen (see Table 9). Nearly 100% of the cells isolated from 18 glioma cell explants displayed HLA class I antigen at variable MFIs. The concept of intratumoral alloCTL for cellular therapy of brain tumors, where lysis should be largely restricted to tumor cells, was first developed by the present inventor. Since brain tumor specimens are often unavailable to use for sensitization of tumor-specific CTL, a cellular therapy that employs allogeneic effector cells derived from healthy donors holds advantage and relies only on the blood lymphocytes from the patient to use as stimulators as they display high levels of HLA (see Table 9).

TABLE 9

| HLA | Average % Positive (MFI) | |
| --- | --- | --- |
| | Class I | Class II |
| Normal Brain | 6.6 (1.1) | 2.1 (1.5) |
| Gliomas | 98.5 (168) | 2.2 (1.0) |
| Lymphocytes | 86.5 (9.8) | 15.8 (1.0) | alloCTL are cytolytic towards targets displaying the HLA to which they are sensitized. Data from a chromium release assay (see Table 10) show that alloCTL made from two donors (D1 and D2) that were sensitized to the HLA of glioma patient 12-11, lysed the 12-11-MG glioma cells and lymphoblasts autologous to the patient, but not the donor blasts (negative control). However, alloCTL made from the same two donors sensitized to the HLA of normal brain donor 03-08, did not lyse 03-08-NB normal brain cells. These data provide evidence that the goals could be accomplished, to achieve alloCTL lysis of lymphoblasts, also to achieve lysis of glioma cells.

Moreover, alloCTL demonstrated exquisite specificity to targets displaying the HLA to which they were sensitized, being more cytolytic to relevant tumor target cells than partially-relevant tumor targets (see FIG. 8). alloCTL specificity by cold target inhibition assays and alloreactivity was demonstrated by proving an inhibition to lysis when blocking antibodies to class I or to TCR molecules were placed into cytotoxicity assays. Other preclinical and animal studies showed alloCTL mobility and specific injury to glioma cells in vivo, implying that the immune privilege of the brain protects the allogeneic cells from endogenous immune cell attack long enough that such allogeneic cells fulfill their trafficking and effector functions.

TABLE 10

| Cytotoxicity Data of Relevant/ Irrelevant Targets | | | | |
| --- | --- | --- | --- | --- |
| Effector | | Percent Lysis | | |
| alloCTL[a] | Human Target Cells[b] | 100:1[b] | 50:1 | 25:1 |
| D1 anti-12-11 | 12-11-MG Glioblastoma | 44.7 ± 2 | 41.3 ± 2 | 31.0 ± 0 |
| | 12-11 Lymphoblasts | 52.7 ± 3 | 61.6 ± 3 | 66.3 ± 5 |
| | D1 Lymphoblasts | 0.0 | 0.0 | 0.0 |
| D2 anti-12-11 | 12-11-MG Glioblastoma | 33.2 ± 1 | 27.4 ± 2 | 15.6 ± 1 |
| | 12-11 Lymphoblasts | 43.2 ± 3 | 49.2 ± 4 | 47.1 ± 5 |
| | D2 Lymphoblasts | 0.0 | 0.0 | 0.0 |
| D1 anti-03-08 | 03-08-NB Normal Brain | 0.0 | 0.8 | 0.0 |
| D2 anti-03-08 | 03-08-NB Normal Brain | 0.0 | 0.0 | 0.0 |

[a]The alloCTL day 14 post MLR. Sensitization was to the HLA antigen present on irradiated 12-11 or 03-08 lymphoblasts at a R:S of 10:1.
[b]The E:T ratio at which the mean percent lysis ± SE in the chromium release assay.

Cytokine Production by alloCTL, Glioma Cells and Upon their Coincubation.

Multiple human cytokines were detected by use of a Th1/Th2 10-plex cytokine kit. The Th1 and Th2 cytokines secreted by the alloCTL; the glioma cells; and the results when the two were coincubated (after treatment of the glioma cells with brefeldin to prevent secretion) are given in Table 11. The cytokine data indicate the vigorous response, especially IL-6 and IL-8, to coincubation of the alloCTL with relevant target cells (13-06-MG) compared to the less robust response to partially relevant target cells (DBTRG-05MG). Although interferon-γ (IFN-γ) was also upregulated upon alloCTL coincubation, production surprisingly was not more robust. However, it was found to be much more informative to look at the specific cytotoxic subsets within the alloCTL preparations.

TABLE 11

Cytokines secreted by alloCTL or glioma cells, or by coincubates of alloCTL & brefeldin-treated glioma cells.*

| Effector | Targets | GM-CSF | IFN-γ | TNF-α | IL-1β | IL-4 | IL-5 | IL-6 | IL-8 | Il-10 |
| --- | --- | --- | --- | --- | --- | --- | --- | --- | --- | --- |
| anti-13-06 alloCTL | None | 40 | 164 | 37 | 14 | 44.5 | 886 | 81 | 1245 | 483 |
| None | 13-06-MG | 16 | 14 | 21 | 15 | 46.5 | 16 | 635 | 3431 | 10 |
| anti-13-06 alloCTL | 13-06-MG | 96 | 284 | 51 | 16 | 50.5 | 1112 | 2007 | 5644 | 578 |
| None | DBTRG-05MG | 12 | 26 | 23 | 13 | 44.5 | 24 | 47 | 511 | 12 |
| anti-13-06 alloCTL | DBTRG-05MG | 76 | 309 | 45 | 17 | 42.5 | 1102 | 217 | 2003 | 518 |

*Concentrations of cytokines in pg/ml are given after subtracting medium alone values.

Response by alloCTL Cytotoxic T Cell Subsets to Restimulation with Relevant Target.

alloCTL preparations were monitored using the BD Fast Immune Kit, which contains surface markers for CD3-APC, CD8-PerCP Cy5.5, CD69-PE and provides for intracellular FITC determination. CD69 is an early activation marker and IFN-γ generally sorts with CD69+ cells. Precursor alloCTL were combined with inactivated sensitizing lymphocyte blasts at a R:S ratio of 10:1. At 14 days post-MLR, the alloCTL were phenotypically analyzed, or restimulated with relevant inactivated glioma targets for 18 hr and then similarly analyzed. In Table 12, alloCTL with a CD3+/CD8+/CD69+ subset at 10.5% of the total CD3+ cells are shown; half of that subset (52.1%) also expressed IFN-γ at a MFI of 500. When the alloCTL were restimulated with relevant target cells, the percentage of CD3+/CD8+/CD69+ cells increased 6-fold and a third of them also expressed IFN-γ at a 5-fold higher MFI. When the same preparation was analyzed for the CD3+/

CD4+/CD69+ subset, upon incubation with relevant target less than 1% of them were IFN-γ positive. Thus, the CD3+/CD8+ cells reacted by producing proinflammatory IFN-γ upon exposure to the relevant HLA glioma antigens.

TABLE 12

Phenotypic analysis of activated T-cell subsets within alloCTL before and after restimulation with relevant target cells

| alloCTL +/− relevant glioma target | T-cell subset phenotype | % of CD3+ cells with phenotype | % of CD3+ subset also IFN-γ+ | IFN-γ MFI |
|---|---|---|---|---|
| alloCTL | CD3+/CD8+/CD69+ | 10.5% | 52.1% | 500 |
| alloCTL + target glioma | CD3+/CD8+/CD69+ | 62.7% | 34.7% | 2543 |
| alloCTL | CD3+/CD4+/CD69+ | 35.3% | 0.7% | 254 |
| alloCTL + target glioma | CD3+/CD4+/CD69+ | 80% | 0.9% | 1605 |

Methods for Example 9

HLA Typing.

Histocompatibility antigen typing of volunteer donors is planned. The R and S cells will be HLA typed by high resolution molecular DNA methods for class I HLA-A, B, C and for class II DR, DP, DQ using real time polymerase chain reaction (RT-PCR) sequence specific primers (SSP) or by sequence-based tying (SBT). This will provide an assessment of the effectivity of one or more of the described methods, because of potential mismatches at class I and class II, which influence MLR cytolytic and proliferative responses.

AlloCTL Generation.

alloCTL could be generated as previously described. Precursor alloCTL (PBMC) from a pool of molecularly-HLA typed, young (21-50 year old) allodonors was employed, since use of young donors maximizes the likelihood of a vigorous response. Responder PBMC was combined with 127Cs-irradiated stimulator lymphocytes, at a R:S ratio of 10:1 (i.e., one-way MLR). They were cultivated at 37° C. with 5% $CO_2$ with AIM V medium containing 5% autologous serum and 60 IU/ml of rIL 2 for 14 days, during which the cells were weaned from serum containing medium. Two days after restimulation (day 14 post-MLR) cytotoxicity assessments, proliferation, phenotypically-defined cytotoxic subsets and cytokine production could be determined.

Cytotoxicity of Relevant Target.

Lysis of target lymphoblasts by the alloCTL in 4 hr assays (triplicate samples at E:T of 3:1, 10:1, and 30:1) could be evaluated and normalized. Normalized cell lysis by the alloCTL of stimulator lymphoblasts could be categorized as low (e.g., achieving between 0-33% cell injury), intermediate (between 34-65% cell injury), or high (>66% cell injury). Both conventional regression modeling with the general linear model and its robust analogues could be used to assess the HLA mismatch and alloresponsive characteristics across E:T ratios. In vitro cytotoxicity data could then be correlated with the HLA mismatch structural evaluations.

Cytotoxic T Cell Subsets Producing Proinflammatory Cytokine Upon Exposure to Relevant Targets.

The phenotypic analysis of the alloCTL preparations by flow cytometry using the BD Fast Immune Kit could allow a determination of the CD3+/CD8+/CD69+/IFN-γ+ fold increases achieved upon restimulation of the alloCTL with irradiated stimulator lymphoblasts, as detailed earlier.

To evaluate proliferation of the specific subsets, the BrdU-APC Cy7 antibody could be included in the staining mixture as well. The fold increases is specifically related to mismatched HLA-eplets (number and type). For purposes of multi-factorial analysis, fold increases of the cytotoxic T cell subset could be analyzed that produce proinflammatory cytokine by categorizing each alloCTL preparation into one of three cytotoxic T cell categories. Although subject to modification once additional data were collected, the definitions for categories were envisioned to be: (1) low as <1-fold increase in CD3+/CD8+/CD69+/IFN-γ+, (2) intermediate as >1 but <1.5-fold CD3+/CD8+/CD69+/IFN-γ+, and (3) high as >1.5 CD3+/CD8+/CD69+/IFN-γ+.

Because the stimulator lymphoblasts are lethally-irradiated before being mixed with responder cells, they do not fall in the live cell gates analyzed. Additionally, since the T-helper cell CD4+ phenotype could be analyzed, three CD4+ helper/inducer T-cell categories could be similarly defined as low, intermediate, and high. The fold increases obtained in the IFN-producing, activated T cell subsets within alloCTL preparations, and the CD4:CD8 ratios that are also CD69+/BrdU+, could be correlated with HLA mismatches and analyzed by polytomous logistic regression analyses.

Production of Th1/Th2 Cytokines Upon Exposure to Relevant Targets.

Supernates from alloCTL coincubated for 24 hr in the presence of irradiated, brefeldin-treated stimulator lymphoblasts could be examined for cytokine secretion in triplicate as described earlier. The Th1 and Th2 cytokines assessed by BD Cytometric Bead Array included IL-2, IL-4, IL-5, IL-10, IFN-γ and TNF-α using clarified medium (100 µl aliquots). Although the four cytokines (IFN-γ, IL-10, TNF-α, IL-4) could be measured using sandwich ELISA at levels of detection of 2.0-4.0 pg/ml, the array system was a cost effective, time-saving alternative that could provide analysis of multiple Th1:Th2 permutations. Again, subject to modification based upon additional data collected, ratios of Th1:Th2 cytokines >2.0 may be used, which would be considered to be highly proinflammatory, ratios <2.0 but >1.0 to be proinflammatory, and ratios <1.0 to be anti-inflammatory.

Other permutations of the Th1 to Th2 cytokines could be assessed, such as IL-12/IL-10, or additive Th1 and Th2 cytokine ratios (i.e., IFN-γ+TNF-α/IL-10+IL-4) could be analyzed if dichotomous results were obtained. IL-2 would be disregarded as it is a component of the medium in which the alloCTL were maintained and thus likely to be at a concentration in a nonlinear range. These analyses were selected as ratios of the Th1- to Th2-type cytokine producing cells (i.e., IFNγ/IL-10 ratios) as informative in predicting rejection, a T-cell driven response, in transplant patients, and as a response in immunotherapy treated (vaccinated) patients.

Example 10 alloCTL Could Induce Glioma Cell Apoptosis and Lysis

During cell injury, the plasma membrane of the target cells becomes increasingly permeable and a fluorescent DNA dye, 7-amino actinomycin D (7AAD) that selectively binds to guanosine/cytosine regions of the DNA, is taken up by the cells in proportion to the degree of injury. FIG. 8 depicts scattergrams that were generated from this flow cytometric-based assay that distinguished live, early apoptotic, and dead/late apoptotic cells.

Significant glioma cell injury occurred quite rapidly upon their coincubation with alloCTL. The apoptotic/necrotic segregation was confirmed, demonstrating that cells within the "dead region" were positive for propidium iodide, and >75% of the cells within the "apoptotic region" stained with annexin-V that binds the early apoptotic marker, phosphatidylserine. This assay can serve as an alternative assay to the chromium release cytotoxicity assay.

FIG. 10A shows the quick recycling capability of cytolytic T cells. Over a span of 480 sec, one CTL bound to three tumor cells induced the lysis of all three targets.

In particular, FIG. 10A shows under fluorescent microscopy, a single effector killer T cell is in contact with three tumor (glioma) cells. Within 480 seconds, the killer cell sequentially lyses each of the tumor cells. One CTL effector cell (identified as CTL) staining positive for granzymes (position between cell CTL and cells 1, 2 and 3) is shown in contact with three tumor cells (identified by numerals 1, 2, and 3).

CTL showed the ability to "recycle" and lyse more than one tumor cell in a short period when they come into contact with them. In each of the successive panels, one tumor cell bound to the CTL was lysed.

FIG. 10B shows Hematoxylin & Eosin stained 13-06-MG glioma cell monolayer cultured for 4 hr in the absence of aCTL. Normal, non-apoptotic adherent brain tumor cells were large in size, contained ample cytolplasm, and had large oval nuclei. Few apoptotic brain tumor cells were detected.

FIG. 10C shows the 13-06-MG glioma cell monolayer coincubated with nonadherent anti-13-06 aCTL for 4 hr. After washing the monolayer to remove nonadherent cells, the attached glioma cells appeared apoptotic and demonstrated classic morphologic changes indicative of programmed cell death: condensed nuclei (small black arrows, identifies as A1), fragmented nuclei (large black arrows, identified as A2), and shedding of apoptotic bodies and membrane blebbing (paler arrowheads identified as A3).

Methods for Example 10

AlloCTL generation, 51-Cr release assays, proliferation of cytotoxic immunophenotypes and cytokine analysis were performed as described in Example 9, except that the cells used for targets and for restimulation were cultured glioma cells from the same patient who provided stimulator lymphocytes for the MLR.

Considerable experience exists in processing brain tumor specimens into single cells and their subsequent culture (Bakir A, Gezen F, Yildiz O, Ayhan A, Kahraman S, Kruse Calif., Varella-Garcia M, Yildiz F, Kubar A, Establishment and characterization of a human glioblastoma multiforme cell line, could Gen and Cytogenet, 1998; 103(1):46-51; Gjerset R, Fakhrai H, Shawler D, Turla S, Dorigo O, Grover-Bardwick A, Mercola D, Wen S, Collins H, Lin H, et al, Characterization of a new human glioblastoma cell line that expresses mutant p53 and lacks activation of the PDGF pathway, In Vitro Cell & Dev Biol. 1995; 31(3):207-14; Kruse C, Mitchell D, Kleinschmidt-Demasters B, Franklin W, Morse H, Spector E, Lillehei K, Characterization of a continuous human glioma cell line DBTRG-05MG: growth kinetics, karyotype, receptor expression, and tumor suppressor gene analyses, In Vitro Cell Dev Biol. 1992; 28A (9-10):609-14; Kruse C, Varella-Garcia M, Kleinschmidt-Demasters B, Owens G, Spector E, Fakhrai H, Savelieva E, Liang B, Receptor expression, cytogenetic, and molecular analysis of six continuous human glioma cell lines, In Vitro Cell & Dev Biol. 1998; 34(6):455-62).

Example 11

Clinical Experience with alloCTL

Prior experience with six recurrent malignant glioma patients (3 Grade III, 3 Grade IV) entered into a pilot alloCTL clinical trial (FDA BB-IND-5423) demonstrated that the acute toxicity was acceptable and long-term toxicity was not evident. Besides demonstrating feasibility and tolerable short-term toxicity, it was also demonstrated that the immune-based therapy might had been beneficial for the three recurrent Grade III gliomas in long-term follow-up. One recurrent Grade III patient lived 40 months following entrance into the immunotherapy protocol, a much better response than the typical natural history of the disease. Two other recurrent Grade III glioma patients are still alive with no evidence of tumor recurrence at over fifteen years from the start of immunotherapy. They have since received no other therapy for their tumors.

The data in Table 13 highlight the experience built in evaluating patient acute toxicity by NCI Common Toxicity Criteria (1-5 scale, right half) and long-term toxicity by assignment of KPS ratings (left half) given to the patients in follow-up. Table 13 also summarizes the highest toxicity recorded over time after receiving the multiple alloCTL infusates during the 10 month treatment period collected with the first five patients receiving a cumulative number of 1 to 52×108 alloCTL in the pilot clinical study. Transient Grades 0 3 toxicity is expected to be seen following administration of individual alloCTL infusates.

Toxicity, if it occurred following infusion, was variable from one infusate to another and included symptoms including fever, headache, nausea, vomiting, and fatigue. The toxicity normally resolved within 24 hr following infusion, except on two occasions for one patient, and one occasion for another, where several more days were needed.

TABLE 13

Evaluation of acute toxicity by NCI Common Toxicity Criteria and long-term toxicity by KPS rating in BTPs.

| Patient No. | Karnovsky Performance Scale rating | | | | | NCI Common Toxicity Criteria/Rating | | | | | |
|---|---|---|---|---|---|---|---|---|---|---|---|
| | 1 | 2 | 3 | 4 | 5 | Fever | Headache | Nausea | Vomiting | Neruomoter | Other |
| BTP1 | 80 | 80 | NA | NA | NA | 2 | 2 | 2 | 2 | 1 | 1 |
| BTP2 | 70 | 70 | NA | NA | NA | 2 | 2 | 2 | 1 | 1 | 1 |
| BTP3 | 90 | 90 | 90 | 100 | 100 | 1 | 2 | 2 | 2 | 1 | 3 |
| BTP4 | 90 | 90 | NA | NA | NA | 2 | 3 | 3 | 2 | 1 | 3 |
| BTP5 | 90 | 90 | 100 | 100 | 100 | 2 | 2 | 3 | 0 | 0 | 1 |

The study had been designed as a standard dose-escalation study. At the first treatment cycle, 108 alloCTL/infusate could be administered. Individual patients received five treatment cycles consisting of two alloCTL infusions a week apart. The first three patients received a cumulative dose of 109 alloCTL over a ten month period, i.e., 10 infusions. Two-fold escalation then proceeded in a 3+3 design for six dose levels that involved 32×108 alloCTL/infusate at the highest dose level. Advancing to the highest dose level could be anticipated, without reaching a maximum tolerable dose determined by modified NCI CTCAEv3.0 criteria.

A reportable adverse event was defined as a "prolonged" grade 2-4 toxicity that does not resolve to <1 within 4 days. This definition allowed a window of three days for QC release criteria to be met for a second infusion, if toxicity should occur from the first infusate, and for inflammation in the CNS to resolve. Added time was given for neurotoxicity to dampen, since CNS immunotherapy treatments could cause transient inflammation that was seen by neuroimaging and resulted in premature placement of some patients off-protocol.

Methods for Example 11

Acute Toxicity Monitoring.

The primary endpoint of concurrent Phase I trial for grade III glioma patients was safety/toxicity. Acute CNS and systemic toxicity assessments were planned. The GCRC provideed a controlled setting where monitoring occurred on an inpatient basis. Acute toxicity measurements were to be assigned following each infusate using a modified NCI CTCAEv3.0 criteria at each treatment cycle and would reflect the highest grade monitored during the 24-hour period following each alloCTL infusion.

Enrollees were to be administered two infusates/allodonor a week apart from which acute toxicity grade relative to R:S HLA disparity was to be assessed. Five donors allogeneic to the patient are to be used as sources of precursor alloCTL. Thus, each of 15 patients was to receive up to ten alloCTL infusates over ten months. Acute toxicity from up to 150 infusates was to be monitored and assigned acute toxicities of grades 0 through 5. Conceivably, one donor from the pool could provide cells for multiple patients. Grade assignments was to be as follows: grade 0—no adverse event (AE), grade 1—minor AE, grade 2—moderate AE requiring minimal intervention, grade 3—severe AE requiring intervention, grade 4—life-threatening or disabling AE, and grade 5—unacceptable AE causing death. It was to be determined whether the developed algorithm prediction for a robust/nonrobust R:S pair used for alloCTL generation correlated to the individual graded acute toxicity the patient might experience after infusion. Comprehensive reporting of all observed toxicities was to be provided, with descriptions of individual toxicities for each patient following each infusate. Sign tests would then be employed to categorize total number of predicted robust/nonrobust R:S pairs for alloCTL used over the entire treatment period and relate that to the total number of AEs graded recorded in each category.

The survival from entry into immune therapy (IMT-S), and overall survival (OS) from diagnosis were to be determined for each patient. It would then be determined whether the developed algorithm prediction for total number of robust/nonrobust R:S pairs for alloCTL gathered over the entire treatment period for any given patient's alloCTL repertoire could be related to the patient segregated into responder/nonresponder groups by survival parameters. All data manipulation and statistical computations were to be done using R, an open-source international collaborative effort that increasingly is becoming the accepted standard for advanced statistical work. A major benefit of R was its enormous roster of contributed analytic packages developed by outstanding statistical professionals around the world.

Based upon available data, it was anticipated that choosing extensively mismatched or similar donor PBMC would generate nonrobust alloCTL responses, whereas an intermediate level of HLA mismatch might generate the most efficacious alloCTL responses. If it resulted that there was no correlation between the extent of HLA mismatch and the degree of alloCTL responsiveness, that would suggest that other factors might be playing a critical role in the generation of cytotoxic alloCTL. This multifaceted approach incorporated current concepts that would be modified for best fit once the in vitro collected information becomes available.

In addition to HLAMm, other investigators have used serologic crossreactive group (CREG) typing, or structural approaches such as Histocheck that applies the so-called distance index of Risler to assess functional similarities between aa substitutions on disparate HLA molecules, or other counting of aa according to physiochemical properties. To date, these efforts have been unsuccessful at predicting the cellular immune response contributing to GVHD in the transplantation field. It is possible they may be useful with the in vitro dataset that are to be collected.

Algorithms that predict for any protein the most likely nonamer peptides that could bind to a given class I allele, see e.g. http://www.imtech.res.in/raghava/mmbpred/algorithm-.html, might be employed to supplements the tests in progress. It might be found that the HLA alignment tool part of the IMGT/HLA Database can be of and these approaches might be employed at a later stage.

Example 12

A mathematical method developed and applied to cancer therapy to predict alloCTL functionality and probable glioma patient response to cellular therapy with any given donor's alloCTL could provide a significant advance in cancer therapy. Such an algorithm, identified herein as HLAalloVx, could also provide more wide-reaching applications within the immunotherapy field.

Cancer patients receiving experimental vaccines made from allogeneic tumor cells or autologous dendritic cell vaccines pulsed with allogeneic tumor lysates rely on tumor antigen-specific immune responses coupled with adjuvant enhancing alloresponse. Effective vaccines would activate endogenous T cell mediated responses to tumor associated antigens restricted to specific HLA types.

The novel algorithm can match specific HLA-typed allogeneic tumor specimens with tumor-bearing individuals, making it possible to appropriately select tumor cells from a bank in order to synthesize a vaccine.

Other applications of the novel algorithm include cellular therapies employing allogeneic cytotoxic T cells and the field of transplantation biology, because a program better predictive of the generation of the T cell immune response associated with GVHD, like HLAMm already was for alloantibody response, would have far-reaching beneficial implications to organ/tissue recipients. Indeed, the same fundamental question answered for brain tumor patient response to alloCTL immunotherapy applies to T-cell driven GVHD transplant predictions, only in reverse.

The HLA-alloVx algorithm finds additional applications in cancer patients receiving types of cancer vaccines that activate tumor antigen-specific immune responses and that were coupled with an adjuvant enhancing alloresponse. One such example is use with vaccines made from allogeneic tumor cells/lysates or vaccines made from autologous dendritic cells pulsed with allogeneic tumor lysates. Another example is allogeneic treatments for cancer such as allogeneic T cells that were genetically modified to express molecules that would target them to bind glioma cells or allogeneic T cells that target viral antigens on glioma cells. These types of therapies would be especially important for patients who have brain tumors in non-resectable areas of the brain such as the brain stem, or parietal area of the brain.

The above described applications of the novel algorithm are only exemplary. In different situations, the novel algorithm would be implemented on a computer-type machine that includes recordable media and provides screen displays of results, either in numerical or/and in graphical form.

Moreover, an algorithm according to the invention enables the production of one or more compositions that are administered to a patient to overcome a tumor, organ rejections, or other types of illnesses.

In one embodiment, the invention relates to a composition to kill a brain tumor. The composition is injected into the patient's cranium after an initial surgery has generated a conduit, through which the clinician can dispense the composition to the target brain area.

Example 13

Tumor associated antigens (TAA) have been found to be proteins that are expressed by tumor cells, but not by normal cells. Since TAA appear "foreign to self" they are processed and presented on HLA class I molecules. Referring to Tables 14 and 15, TAA expression on HLA class I molecules resulted in the activation of cytolytic T cells. Interestingly, TAA were HLA restricted, meaning that specific TAA were expressed by specific HLA types (See Tables 14 and 15). The types of TAA associated with a tumor of any given individual might be predicted by their HLA type. Alternatively, knowing what TAAs are present could help in predicting HLA type.

TABLE 14

Examples of tumor associated antigens (TAA) and the HLA alleles that they align with..

| HLA-A2 | HLA-A1 | HLA-A24 | HLA-A26 |
|---|---|---|---|
| B-cyclin | Aim-2 | Sart-1 | Sart-1 |
| ephA2 |  | Survivin |  |
| Gage-1 |  | hTERT |  |
| gp100 |  |  |  |
| Her2/neu |  |  |  |
| hTERT |  |  |  |
| IL-13R 2 |  |  |  |
| MART |  |  |  |
| MAGE |  |  |  |
| Trp-2 |  |  |  |
| Tyrosinase |  |  |  |
| Survivin |  |  |  |

HLA molecules are different between a cancer patient and an allogeneic tumor cell line or lysate. Parts of the HLA molecule is expected to be processed and presented by the patient's HLA, thus allowing for the establishment of an allogeneic adjuvant response in addition to the response to TAA discussed above. Thus, the HLA-Vx algorithm can be used to determine which tumor cell lines or tumor cell lysates contribute to the most robust allogeneic adjuvant response based on disparity in HLA between patient and cell line/lysate.

TABLE 15

Tumor associated precursor proteins detected in glioma cell lines that have been associated with specific HLA types, and real Time PCR expression of AIM-2, GAGE-1, SART-1 and Trp-2 mRNA

| | Glioma | | | | | | | | | | | |
|---|---|---|---|---|---|---|---|---|---|---|---|---|
| Antigen | A172 $\Delta C_t$ | SF767 $\Delta C_t$ | D-54 $\Delta C_t$ | LN229 $\Delta C_t$ | U-251 $\Delta C_t$ | T98G $\Delta C_t$ | U-373 $\Delta C_t$ | U-87 $\Delta C_t$ | LN18 $\Delta C_t$ | SNB19 $\Delta C_t$ | LNZ308 $\Delta C_t$ | U-118 $\Delta C_t$ |
| Aim-2 | 18.5 | 20.3 | 17.2 | 17.3 | 14.6 | 16 | 17.9 | 18.3 | 15.3 | 17 | 14.8 | 14.9 |
| Gage-1 | ND | ND | ND | ND | ND | ND | ND | ND | ND | ND | ND | 20.4 |
| Sart-1 | 21.5 | 22.6 | 19.7 | 19.1 | 22.9 | 20 | 21.4 | ND | 18 | 22 | ND | 19.8 |
| Trp-2 | ND | 21.6 | ND | 18.9 | ND | 21 | 22.3 | ND | ND | ND | ND | 20.1 |
| HLA | A1+ | | A3+ | | | | 2+ | | | | 24+ | |

Tumor cell lines or lysate allogeneic to the tumor bearing patient are the basis to provide cancer immunotherapies. Banks of tumor cell lines are already established that can be used for allogeneic vaccines to treat an array of cancer types. When allogeneic tumor cells or lysates are used as part of a cell based vaccine, the tumor proteins become broken down, processed, and presented by dendritic cells. This can be performed in vitro, when the patient's dendritic cells are "loaded" with the allogeneic tumor cells or lysate in the laboratory, or in vivo, when the patient's dendritic cells endogenous to the body come into contact with the injected allogeneic cells or lystae. The TAAs can also be presented to the dendritic cells attached to a nanoparticle, for example, a nanoparticle of the type described above.

Figure 11:
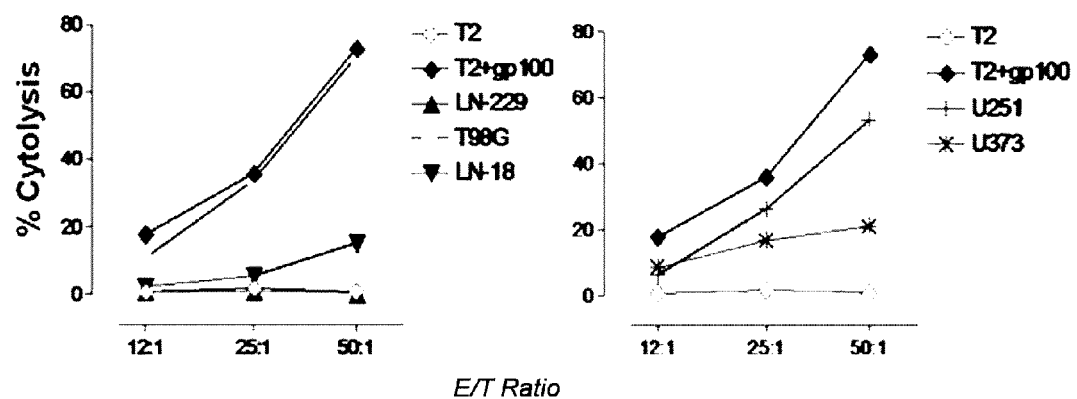
FIG. 11 shows that CTL obtained through certain embodiments are very specific and can kill targets that only display both the correct HLA allele and the tumor associated antigen (TAA).

In particular, allogeneic T cells modified to target glioma specific antigens such as IL-13Ra2 or CMV antigens contain a precursor population of alloresponsive T cells that recognizes and potentially cytotoxically respond to HLA expressed on tumor cells. FIG. 11 illustrates that CTLs are very specific and could kill targets only that display both the correct HLA allele and the TAA. In particular, FIG. 11 shows that gp100-Specific tumor infiltrating lymphocytes (TIL) recognize and kill only the HLA-A2+Glioma Cells Expressing gp100.

Since the above described cytotoxic response is mediated by differences in HLA between the brain tumor patient and allo-donor, the HLA-Vx algorithm can determine donors of allogeneic cells that provide a strong allogeneic response in addition to a response achieved by the targeted glioma expressed molecules.

As mentioned, the HLAalloVx algorithm is applicable to vaccines that activate an endogenous T cell mediated response to tumor associated antigens (TAA) as TAA are restricted to specific HLA types. In this case, specific HLA-typed allogeneic tumor specimens are matched with the HLA type of the patient so that appropriate selection of tumor cells from a bank could be chosen to synthesize of a vaccine.

Currently, no computer based algorithm is available that predicts acute graft versus host disease (GVHD) based on the HLA types of the recipient and donor. GVHD is primarily T cell mediated (Pidala, J. and Anasetti, C, Could antigen-specific regulatory T cells protect against graft versus host disease and spare anti-malignancy alloresponse? Haematologica, 95 660-5; Reddy, P, 2003, Pathophysiology of acute graft-versus-host disease, Hematol Oncol, 21 149-61). Lymphocytes in transplanted tissue are activated to proliferate by the antigen presenting cells of the recipient. According to the invention, the algorithm identifies mismatches between organ donor and recipient that would be non-permissible. Since this immunological response is in part mediated by differences in HLA, the algorithm is applicable to transplantation immunobiology.

In fact, one aspect of the invention relates to a program better predictive of the generation of the T cell immune response associated with GVHD. This program is expected to have far-reaching beneficial implications to organ/tissue recipients. The patient's immune cells could be the responders (Host vs Graft) or the stimulators (GVHD). The stimulators could be cells from the transplanted tissue (GVHD) or from the patient (Host vs Graft Disease).

Comparing the HLA of the patient with the organ/tissue donor focuses on specific matches of molecular HLA types. Precise matching provided by HLA-Vx results in reduction in T cell mediated GVHD or HVGD, and enhanced/improved engraftment following transplant compared to matching based on serotypes.

Because an active immune therapy operates endogenously within the patient in the way of a tumor vaccine, the use of HLA-alloCT or HLA-alloVx for cancer vaccines can cover a variety of cancers, including those vaccines targeting "cancer stem cells" that have been shown to express high levels of HLA Class I (Wei J, Barr J, Kong L Y, Wang Y, Wu A, Sharma A K, Gumin J, Henry V, Colman H, Sawaya R, Lang F F, Heimberge A B, Glioma-associated cancer-initiating cells induce immunosuppression, Clin Cancer Res, 16 461-73).

The patient's endogenous immune cells could also be caused to respond. Such cells may include T-cells, dendritic cells, or other types of immune cells. The stimulator is a tumor associated antigen (TAA) rather than inactivated patient lymphocytes. In this respect, TAA sources include: whole tumor cells, DNA/RNA vaccines, whether or not conjugated with liposomal membrane proteins, tumor cell lysates or homogenates, established tumor cell lines, or synthetic peptides or fragments therein of TAAs.

The pairing of the stimulator to the responder focuses on specific matches of molecular HLA types. Precise matching provided by the new algorithm produces more specific cell-mediated responses than choosing donors based on HLA serotypes. This results in more reproducible (and therefore more predictable) vaccine effects, more effective cell-mediated effects against tumor targets, and minimized undesirable effects such as autoimmunity, expansion of T suppressor cell populations and TGF beta levels, escape of "tumor stem cell" populations, or inflammation-mediated damage to normal tissues.

Cancer vaccines produced using the algorithm according to the invention could be combined with other passive immunotherapy strategies such as cellular therapy, including adoptive transfer of ex vivo activated CTL. Such vaccines could be used in combination with other existing therapies—particularly those which downregulate T suppressor cells or suppressive myeloid cells, such as antibodies to Foxp3 or CTLA4. Instead, surgical resection would reduce suppression of tumor-produced immunosuppressive factors, such as TGF-beta, IL-10 and infiltrating suppressive immune cells.

Methods for Example 13

Cytotoxicity Assays.

Fourteen days after the start of the one-way mixed lymphocyte reactions (MLRs), alloreactive cytotoxic T lymphocytes (alloCTLs) were evaluated for their cytotoxic ability toward relevant target (or stimulator) cells in a 4 hr Chromium-51 (Cr-51) release assay. Briefly, target cells were loaded with Cr-51 and plated with alloCTL at multiple effector to target (E:T) ratios.

After a 4 hour incubation, cell death was determined by release of Cr-51 into the supernatant. Spontaneous and maximal release of Cr51 was measured, and the percent lytic activity of each alloCTL preparation was calculated according to the following equation:

(test release−spontaneous release/maximal release−spontaneous release)×100.

FIG. 6 reproduces data showing that different alloCTL preparations kill target lymphoblasts to varying extents. In particular, FIG. 6 reproduces data from 4 hr Cr51 release assays showing that alloCTL generated following one-way MLR using responder cells from five different donors are variably cytotoxic toward target lymphoblasts. Numbers on the axis refer to one-way MLR number. Statistical significance was evaluated using two-way ANOVA and Bonferroni post-tests. (* $p<0.05$). These data are representative of two separate experiments.

alloCTL generated in one-way MLR3 were significantly ($p<0.05$) more lytic toward target cells than alloCTL generated on one-way MLR1, 2 and 5. alloCTL, generated in one-way MLR4 killed target lymphoblasts, were significantly ($p<0.05$) better than those generated in one-way MLR 2. The percent lysis of target cells was significantly reduced when target cells were incubated with anti-HLA indicating that the cytolytic function of alloCTL is in part HLA restricted. Taken together, these data further show that choice of R:S pairs could affect cytotoxic effector functions of alloCTL generated following one-way MLR.

Phenotype, Proliferation and Cytokine Production.

The ability of allogeneic subsets of CD4+ and CD8+ T cells to proliferate and produce IFN-γ following re-stimulation with target lymphoblasts was evaluated using flow cytometry. Data were from five separate one-way MLR's that are from different R:S pairs than above. AlloCTL were restimulated on day 14 post one-way MLR at a 1:1 responder to stimulator (R:S) ratio with target lymphoblasts, or left unstimulated. Cells were then cultured for 24-48 hours at 37° C. in a 5% $CO_2$ humidified incubator in the presence of the uridine analog bromodeoxyuridine (BrdU). BrdU was incorporated into the DNA of the cell as it divided. A protein transport inhibitor, GolgiStop, was added during the last five hours of culture. Cells were then surface stained for CD4 and CD8, and then fixed, permeabilized and stained for BrdU and IFN-γ according to protocol (BD BrdU Flow Kit). Cells were phenotyped on a LSR II flow cytometer (BD Biosciences), and analysis was performed using the program FlowJo.

Figure 12A:
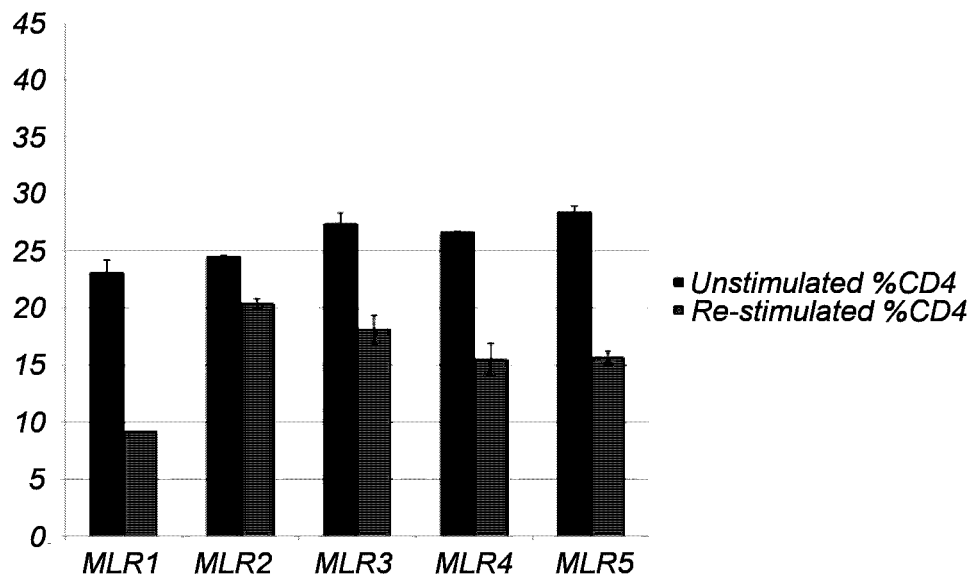
FIGS. 12A-12B show the results of an experiment, in which alloCTL generated in five separate one-way MLR's were unstimulated (darker bars) or re-stimulated (paler bars) for 48 hours.
Figure 12B:
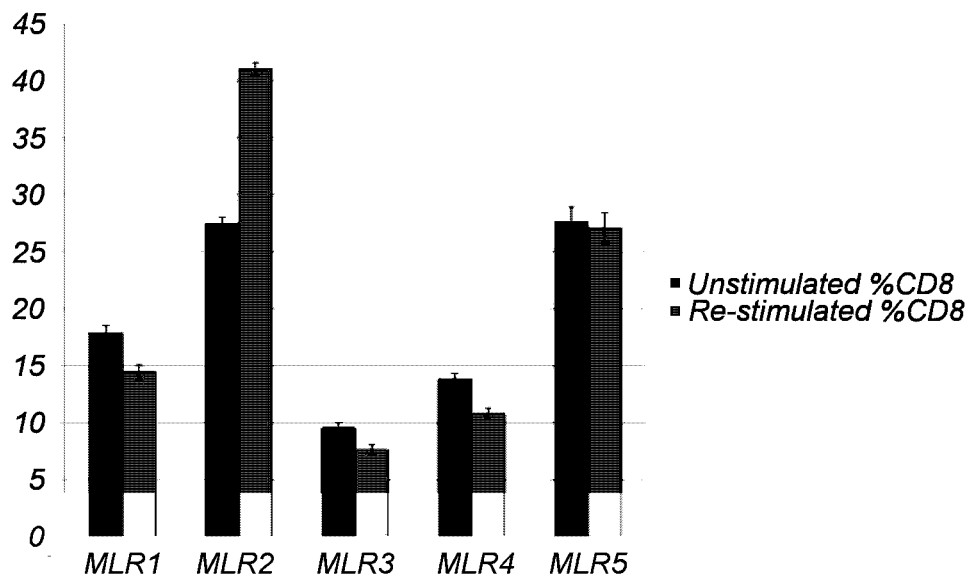

These data show that CD4+ (FIG. 12A) and CD8+ (FIG. 12B) T cells represented an average of 26.0% (range: 23.1% to 28.4%) and 19.3% (range: 9.56% to 27.6%) of the unstimulated alloCTL culture, respectively. Interestingly, 48 hr following re-stimulation with lymphoblasts the percentage of CD4+ T cells was reduced by 16-60%, while the percentage of CD8+ T cells was only modestly reduced by only 2-20% or in some cases increased significantly ($p<0.007$), as in MLR 2.

The percentage of CD4+ and CD8+ T cells that were proliferating, and producing the cytokine IFN-γ, were also quantified. Tables 16 and 17 show the percentage of CD4+ and CD8+ T cells that took up the BrdU during the 48 hr culture period. Overall, the percentage of CD4+ T cells that were positive for BrdU (see Table 16) was reduced following re-stimulation with lymphoblasts, except in the case of MLR 2 where the percent of CD4+BrdU+ T cells was significantly higher. Restimulation did not generally affect the percentage of proliferating CD4+BrdU+ T cells that were also making IFN-γ, except in the case of MLR2 and 5 ($p<0.002$).

TABLE 16

Percent of CD4+ T cells that are BrdU+ and expressing IFN-γ

| | | % CD4+ BrdU+ | % CD4+ BrdU+ IFN-γ+ |
|---|---|---|---|
| MLR 1 | unstimulated | 3.0 ± 0.1 | 1.1 ± 0.1 |
| | re-stimulated | 1.8 ± 0.3 | 0.73 ± 0.3 |
| MLR 2 | unstimulated | 3.0 ± 0.01 | 0.91 ± 0.1 |
| | re-stimulated | 6.6 ± 0.3* | 4.2 ± 0.1* |
| MLR 3 | unstimulated | 3.7 ± 0.7 | 0.79 ± 0.3 |
| | re-stimulated | 1.4 ± 0.03 | 0.6 ± 0.7 |
| MLR 4 | unstimulated | 5.1 ± 0.3 | 1.2 ± 0.001 |
| | re-stimulated | 2.8 ± 0.3 | 1.87 ± 0.23 |
| MLR 5 | unstimulated | 10.5 ± 0.1 | 3.0 ± 0.1 |
| | re-stimulated | 8.0 ± 0.8 | 4.1 ± 0.01* |

*$p < 0.002$ when compared to unstimulated cells by students, t test

Proliferation of CD8+ T cells following re-stimulation of the five separate MLRs was variable (see Table 17, below). In some cases, re-stimulation did not result in increased proliferation, as in MLR1, 3 and 4. However, restimulation resulted in a significant increase in proliferation of CD8+ T cells in the case of MLR2 and 5 ($p<0.02$).

Expression of IFN-γ by proliferating cells followed the same trend, and the percent of CD8+BrdU+ T cells that were also producing IFN-γ was significantly increased in MLR2 and 5 following restimulation.

TABLE 17

Percent of CD8+ T cells that are BrdU+ and expressing IFN-γ

| | | % CD8+ BrdU+ | % CD8+ BrdU+ IFN-γ+ |
|---|---|---|---|
| MLR 1 | unstimulated | 8.6 ± 0.8 | 4.9 ± 0.01 |
| | re-stimulated | 12.1 ± 1.0 | 5.6 ± 3.4 |
| MLR 2 | unstimulated | 9.0 ± 0.7 | 4.7 ± 0.5 |
| | re-stimulated | 36.7 ± 0.3* | 28.9 ± 0.4* |
| MLR 3 | unstimulated | 2.6 ± 0.3 | 1.1 ± 0.38 |
| | re-stimulated | 2.9 ± 0.13 | 2.4 ± 0.38 |
| MLR 4 | unstimulated | 7.0 ± 0.2 | 3.8 ± 0.1 |
| | re-stimulated | 7.4 ± 0.7 | 5.9 ± 0.9 |
| MLR 5 | unstimulated | 15.0 ± 1.1 | 8.4 ± 1.6 |
| | re-stimulated | 24.3 ± 0.8* | 21.5 ± 1.0* |

*$p < 0.002$ when compared to unstimulated cells by students t test

Overall, the above data show that alloCTL generated following one-way MLR with different S:R pairs results in variable phenotypic and cytotoxic subsets, and in cells that respond variably to re-stimulation. Supernatants from the unstimulated and re-stimulated alloCTL were also harvested, and cytokine arrays could also be performed to quantify the milieu of cytokines that were produced during the culture period.

Molecular HLA-Type.

To evaluate how disparity in HLA may play a role in growth and effector functions of alloCTL following one way MLR, stimulator and responder PBMC were high resolution HLA-typed. Molecular HLA Class I and II types of donors providing stimulator and responder cells are summarized in Table 18.

High resolution HLA data types and the above data can be used to evaluate computational programs that identify S:R pairs that generate the most robust and cytotoxic effector alloCTL.

TABLE 18

Molecular HLA Class I and II Types of Donors Providing Stimulator and Responder Cells

| Donor Number | HLA Class I | | | | | | HLA Class II | | | |
|---|---|---|---|---|---|---|---|---|---|---|
| | A | | B | | C | | DR | | DQ | |
| 06-19 | *2407 | | *0705 | *4002 | *0702 | | *1501 | | *0501 | *0502 |
| 10-18 | *2407 | *3401 | *1535 | *3802 | *0702 | | *1201 | *1502 | *0301 | *0502 |
| 03-18 | *0201 | *6801 | *3512 | *4002 | *0401 | *0801 | *0404 | *0802 | *0302 | *0402 |
| 19-07 | *0201 | *1101 | *4402 | *4427 | *0304 | *0401 | *1201 | *1608 | *0301 | *0502 |
| 18-12 | *2402 | *2902 | *4001 | *4501 | *1203 | *0602 | *0401 | *1101 | *0301 | |
| 13-10-08 | *0201 | *2601 | *3501 | *3801 | *0501 | *1203 | *0103 | *0402 | *0501 | *0302 |
| 11-05 | *0101 | *0201 | *0801 | *4402 | *0501 | *0701 | *0301 | *1501 | *0201 | *0602 |
| 03-13 | *0301 | *2501 | *0702 | *4001 | *0702 | *0304 | *0701 | *1501 | *0202 | *0602 |
| 02-10 | *0201 | *1101 | *1801 | *4001 | *0501 | *0304 | *0404 | *1302 | *0302 | *0604 |
| 08-10 | *0101 | *0201 | *0801 | *4402 | *0701 | *0501 | *0301 | *0401 | *0201 | *0302 |

*Table represents a portion of donor pool.

Example 14

Delivery of Peptide Antigens to DCs

A test was performed to confirm that NPs effectively deliver peptide antigens to DCs, as revealed by the presentation of those peptides by MHC on the cell surface. Human DCs were exposed for 1 hr to NPs formulated with varying amounts of test peptide, or were loaded with free peptide by a traditional "pulse" technique. After washing, antigen-loaded DCs were exposed to a CTL line specific for the test peptide, and recognition of peptides by these responders was measured by the specific release of IFN-gamma, as determined by ELISPOT assay.

Human DCs were incubated for 1 hr with polylactic-co-glycolic acid (PLGA) NPs containing Class I-restricted peptides: (A) MART-$1_{27-35}$ (Melan-A antigen) and (B) gp$100_{209-217}$. The DCs were incubated with the relevant peptide (DC+peptide), with empty control nanoparticles (CNP), or with nanoparticles formulated with the same peptides using 300 µg (DC+NP300), or 600 µg (DC+NP600) peptide per batch. Subsequently, the DCs were co-cultured for 20 hours with TIL1235 (recognizing MART-$1_{27-35}$) or TIL1520 (recognizing gp$100_{209-217}$) cells at a ratio of 1:1, and the efficiency of the antigen presentation was evaluated in an IFN-$\gamma$ ELISPOT assay.

In both studies, while DCs loaded with soluble peptide—i.e., peptide alone—could stimulate peptide-specific CTL lines, DCs loaded with a peptide joined to a NP (NP-peptide) produced a more robust response. A comparison of peptides utilized in each case highlights the efficiency of NP delivery: the amount of free peptide used to pulse DCs was approximately six-fold greater than the amount of peptide delivered to the "NP300" group, yet the stimulatory ability of free-peptide-pulsed cells was only about half that of the DC loaded with NP300.

Figure 13:
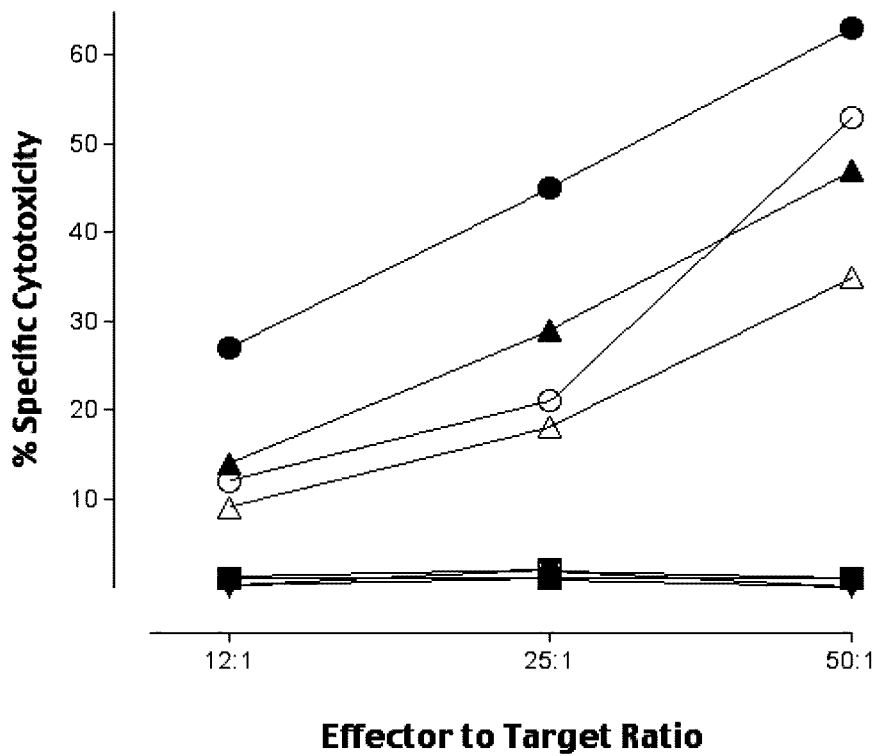
FIG. 13 shows in vitro activation of cytotoxic T lymphocytes (CTL) with peptide-loaded or NP-loaded DCs.

Furthermore, NP-loaded DCs were shown to stimulate de novo CTL induction. Naïve lymphocytes were incubated with DCs loaded with a TAA peptide, delivered either by NPs or in soluble form. After three weekly stimulations in vitro, the two stimulated lymphocyte populations were tested for specific killing ability on several target cells. Please refer to FIG. 13.

Specifically, HLA-A2+ dendritic cells were loaded with the peptide MART-$1_{27-35}$ or with NP containing MART-$1_{27-35}$, and used as APC to induce MART-$1_{27-35}$-specific CTL. CTL activity was evaluated using the following targets: T2 (HLA-A2+; deficient in antigen processing) with or without added peptide; melanoma 624 (MART-1+; HLA-A2+); and melanoma 1351 (MART-1+; HLA-A2−). CTL were incubated with target cells for 4 hr; and cytotoxicity was determined with a standard LDH-release assay (Promega).

On targets susceptible to killing, the CTL activity of the NP-DC-induced CTL (see the filled symbols on the chart and table of FIG. 13) was greater than that of the free-peptide-DC-induced CTL (see the corresponding unfilled symbols). As expected, CTL were HLA-A2 restricted, killing a HLA-A2+ melanoma target, but not a HLA-A2-melanoma. Antigen specificity was demonstrated using the antigen-processing deficient, HLA-A2+ cell line T2.

Final Considerations

While the invention has been described in connection with the above described embodiments, it is not intended to limit the scope of the invention to the particular forms set forth, but on the contrary, it is intended to cover such alternatives, modifications, and equivalents as may be included within the scope of the invention. Further, the scope of the present invention fully encompasses other embodiments that may become obvious to those skilled in the art and the scope of the present invention is limited only by the appended claims.

What is claimed is:

1. A method of preparing alloreactive cytotoxic T cells comprising:
    providing patient cell information, wherein the patient cell information comprises patient cell antigen information that is at least partly determined through one or more of serotyping or a high or intermediate resolution molecular sequencing method of major histocompatibility complex (MHC) information;
    generating stimulator information from donor cell antigen information, wherein the donor cell antigen information is determined at least partly through one or more of serotyping or a high or intermediate resolution molecular sequencing method of MHC information;
    generating responder information from the patient cell antigen information;
    comparing the responder information to stimulator information derived from the donor cell antigen information;
    identifying presence or absence of a partial mismatch between the stimulator information and the responder information among patient cell and donor cell pairs;
    selecting a patient cell and donor cell pair based on the presence of the partial mismatch, wherein the partial mismatch is predictive of an enhanced immune response in the patient; and
    inducing alloreactive cytotoxic T cells endogenous to the patient under conditions sufficient to induce the alloreactive cytotoxic T cells, wherein immune cells endogenous to the patient respond to stimulator antigen derived from the donor to induce the alloreactive cytotoxic T cells based on the patient cell and donor cell pair.

2. The method of claim 1, wherein either or both of the patient cell and the donor cell are derived from peripheral blood mononuclear cells (PBMCs).

3. The method of claim 1, wherein the MHC information is derived from patient lymphocytes.

4. The method of claim 1, wherein the donor and patient cell antigen information is determined at least partly through a high or intermediate resolution molecular sequencing method of MHC information.

5. The method of claim 1, wherein the donor and patient cell antigen information is determined at least partly through a high or intermediate resolution molecular DNA sequencing method.

6. The method of claim 1, wherein the donor and patient cell antigen information is determined at least partly through a high or intermediate resolution molecular RNA sequencing method.

7. The method of claim 1, wherein the donor and patient cell antigen information is determined at least partly through a high or intermediate resolution molecular protein sequencing method.

8. The method of claim 1, wherein the high or intermediate resolution molecular sequencing method comprises one or more of a sequence based typing (SBT), sequence specific primer (SSP), restriction fragment length polymorphism (RFLP), or sequence specific oligonucleotide (SSO) method.

9. The method of claim 1,
    wherein providing patient cell information comprises providing patient cell information derived from human leukocyte antigen (HLA) class I or HLA class II antigen information; and
    wherein the donor cell information is determined at least partly through a high or intermediate resolution molecular sequencing method of HLA class I or HLA class II antigen information of a responder and a stimulator.

10. The method of claim 9, wherein the cell antigen information of the donor and of the patient is derived from amino acid sequences at one or more of HLA class I alpha or beta helices, or within a peptide binding groove.

11. The method of claim 1,
wherein providing patient cell information comprises providing patient cell antigen information derived from HLA II antigen information; and
wherein the donor cell information is determined through a high or intermediate resolution molecular DNA method of HLA class II antigen-type information.

12. The method of claim 1, wherein identifying the presence or absence of a partial mismatch comprises identifying differences in amino acid sequences between patient and donor HLA.

13. The method of claim 1, wherein either or both of the stimulator information or the responder information are generated from one or more of monocytes, antigen presenting cells, dendritic cells, lymphocytes, lymphoblasts, T cells, or tumor cells, or any other cells expressing HLA.

14. The method of claim 1, wherein the stimulator information is tumor associated antigen (TAA) information.

15. The method of claim 14, wherein the TAA is selected from a group consisting of whole tumor cells, DNA/RNA conjugated with liposomal membrane proteins or not, tumor cell lysates or homogenates, established tumor cell lines, and synthetic peptides or fragments therein of TAA.

16. The method of claim 14, wherein the TAA is derived from a tumor cell of the donor.

17. The method of claim 14, wherein the TAA is complexed to a nanoparticle.

18. The method of claim 1, wherein the cells of the patient are combined by contact with stimulator antigen in vivo.

19. The method of claim 1, wherein the immune cells endogenous to the patient are induced to respond to stimulator antigen in vitro.

20. The method of claim 1, wherein the immune cells endogenous to the patient include one or more of T-cells, dendritic cells, or dendritic precursor cells.

21. The method of claim 1, wherein identifying the presence or absence of a partial mismatch between the stimulator information and the responder information among patient cell and donor cell pairs comprises employing an algorithm configured to identify the presence or absence of the partial mismatch.

22. The method of claim 21, wherein the algorithm is a computer algorithm configured to provide sequence-based HLA information to identify acceptable amino acid mismatches.

23. The method of claim 21, further comprising the step of training the algorithm with a training set of data.

24. The method of claim 23, wherein one or more of cytotoxic T cell activation or cytotoxic T cell activity are compiled in the training set.

25. The method of claim 1, wherein the stimulator information is derived from cells of the donor, further comprising the step of inactivating the cells of the donor prior to the inducing step.

26. The method of claim 1, further comprising the step of detecting presence or absence of cytotoxic T cell activation.

27. The method of claim 1, further comprising the step of administering the composition to the patient, wherein administering the alloreactive T cells to the patient comprises administering the cells to a patient having one or more of cancer or cancer stem cells.

28. The method of claim 27, wherein the alloreactive T cells are administered to an immune-privileged site.

29. A method of preparing alloreactive cytotoxic T cells comprising:
providing patient cell information, wherein the patient cell information comprises patient cell antigen information at least partly determined through serotyping or a high or intermediate resolution molecular sequencing method of HLA antigen presenting face or peptide binding groove information;
generating stimulator information from the patient cell antigen information;
comparing the stimulator information to responder information generated from donor cell antigen information, wherein the donor cell antigen information is determined at least partly determined through serotyping or a high or intermediate resolution molecular sequencing method of HLA antigen presenting face or peptide binding groove information;
identifying presence or absence of a partial mismatch between the stimulator information and the responder information among patient cell and donor cell pairs;
selecting a patient cell and donor cell pair based on the presence of the partial mismatch, wherein the partial mismatch is predictive of an enhanced immune response in the patient; and
inducing alloreactive cytotoxic T cells from the donor under conditions sufficient to induce the alloreactive cytotoxic T cells, wherein cells from the donor respond to stimulator antigen derived from the patient to induce the alloreactive cytotoxic T cells based on the patient cell and donor cell pair.

30. The method of claim 29, where the HLA antigen presenting face comprises one or both HLA class I or II alpha or beta helices.

* * * * *